US007728130B2

(12) United States Patent
Allen et al.

(10) Patent No.: US 7,728,130 B2
(45) Date of Patent: Jun. 1, 2010

(54) QUINOLONE BASED COMPOUNDS EXHIBITING PROLYL HYDROXYLASE INHIBITORY ACTIVITY

(75) Inventors: Jennifer R. Allen, Newbury Park, CA (US); Kaustav Biswas, Calabasas, CA (US); Roland Burli, Pasadena, CA (US); Jennifer Dao, Oak Park, CA (US); Michael J. Frohn, Thousand Oaks, CA (US); Jennifer E. Golden, Simi Valley, CA (US); Randall W. Hungate, Camarillo, CA (US); Robert Kurzeja, Newbury Park, CA (US); Stephanie J. Mercede, Woodland Hills, CA (US); Kristine M. Muller, Thousand Oaks, CA (US); Susana C. Neira, Thousand Oaks, CA (US); Tanya A. N. Peterkin, Woodland Hills, CA (US); Christopher M. Tegley, Thousand Oaks, CA (US); Violeta Yu, Moorpark, CA (US)

(73) Assignee: Amgen Inc., Thousand Oaks, CA (US)

( * ) Notice: Subject to any disclaimer, the term of this patent is extended or adjusted under 35 U.S.C. 154(b) by 200 days.

(21) Appl. No.: 11/635,683

(22) Filed: Dec. 8, 2006

(65) Prior Publication Data

US 2007/0249605 A1 Oct. 25, 2007

Related U.S. Application Data

(60) Provisional application No. 60/748,577, filed on Dec. 9, 2005, provisional application No. 60/785,358, filed on Mar. 24, 2006.

(51) Int. Cl.
*C07D 413/00* (2006.01)
(52) U.S. Cl. .................. 544/128; 544/105; 544/238; 544/333; 546/152; 546/157
(58) Field of Classification Search ............. 514/235.2, 514/252.04, 246, 311; 436/501; 544/128, 544/238, 333; 546/152
See application file for complete search history.

(56) References Cited

U.S. PATENT DOCUMENTS

| | | | |
|---|---|---|---|
| 3,954,733 A | | 5/1976 | Tobiki et al. |
| 3,992,371 A | | 11/1976 | Tobiki et al. |
| 4,374,138 A | * | 2/1983 | Haskell et al. ............ 514/196 |
| 4,382,089 A | | 5/1983 | Haskell et al. |
| 4,404,201 A | | 9/1983 | Haskell et al. |
| 4,468,394 A | * | 8/1984 | Machida et al. .......... 514/201 |
| 4,710,473 A | | 12/1987 | Morris |
| 5,502,035 A | | 3/1996 | Haviv et al. |
| 5,798,451 A | | 8/1998 | von Deyn et al. |
| 5,972,841 A | | 10/1999 | von Deyn et al. |
| 6,093,730 A | | 7/2000 | Weidmann et al. |
| 6,593,343 B2 | * | 7/2003 | Bjork et al. ............... 514/312 |
| 6,787,326 B1 | | 9/2004 | Ratcliffe et al. |
| 7,323,475 B2 | | 1/2008 | Arend et al. |

FOREIGN PATENT DOCUMENTS

| | | |
|---|---|---|
| AT | 328085 | 3/1976 |
| EP | 0 500 297 A1 | 8/1992 |
| EP | 0 937 459 A2 | 8/1999 |
| EP | 1 538 160 A1 | 6/2005 |
| GB | 1 449 256 | 9/1976 |
| JP | 4935392 A | 4/1974 |
| JP | 7-224040 | 8/1995 |
| JP | 07224040 | * 8/1995 |
| JP | 7224040 A2 | 8/1995 |
| SU | 1735288 | 5/1992 |
| WO | WO 96/00845 | 1/1996 |
| WO | WO 2004/037853 A2 | 5/2004 |
| WO | WO 2004/103974 | 12/2004 |
| WO | WO 2004/103974 A1 | 12/2004 |
| WO | WO 2004/104000 A1 | 12/2004 |
| WO | WO 2004103974 | * 12/2004 |
| WO | WO 2004104000 | * 12/2004 |
| WO | WO 2006/088246 | 8/2006 |
| WO | WO 2007/038571 | * 4/2007 |
| WO | WO 2007/038571 A2 | 4/2007 |

OTHER PUBLICATIONS

Bohnert et al., Redox reactions with cyclopeptide-like quinoline derivatives as lipophilic, masked NAD model compounds, Zeitschrift fuer Naturforschung, B: Chemical Sciences, (1987), 42(9), 1159-1166.*
Kath et al., Potent small molecule CCR1 antagonists, Bioorganic & Medicinal Chemistry Letters (2004), 14(9), 2169-2173.*
"Oxygen Sensing by HIF Hydroxylases" by Christopher J. Schofield and Peter J. Ratcliffe, Nature Reviews, Molecular Cell Biology, vol. 5, No. 5, May 2004.
"From Peptide to Non-Peptide. 2. The de novo Design of Potent, Non-Peptidal Inhibitors of Platelet Agrregation Based on a Benzodiazepinedione Scaffold" by Robert S. McDowell et al., J. Am. Chem. Soc., vol. 116, No. 12, pp. 5077-5083, 1994.
Ukrainets, I.e., et al., "4-Hydroxy-2-Quinolones. 4. Selection of the Optimum Path for Synthesis of N-R-Substituted 4-Hydroxy-2-Quinolone-3-Carboxylic Acid Amides," Chemistry of heterocyclic Compounds 1992 28(5), 538-540.
He, L., et al., "Probabilistic Neural Network Multiple Classifier System for Predicting the Genotoxicity of Quinolone and Quinoline Derivatives," Chem., Res. Toxicol., 2005, 18, pp. 428-440.

(Continued)

*Primary Examiner*—Karl J Puttlitz
*Assistant Examiner*—Chukwuma O Nwaonicha
(74) *Attorney, Agent, or Firm*—Jones Day

(57) ABSTRACT

This invention relates to new quinolone based compounds that exhibit prolyl hydroxylase inhibitory activity. This invention also relates to methods of increasing HIF levels or activity in a subject or treating a condition associated with HIF levels or activity in a subject by administering to the subject at least one quinolone based compound. This invention further involves assays for the detection of a hydroxyproline residue in a HIF molecule.

6 Claims, 4 Drawing Sheets

OTHER PUBLICATIONS

Figure 1:
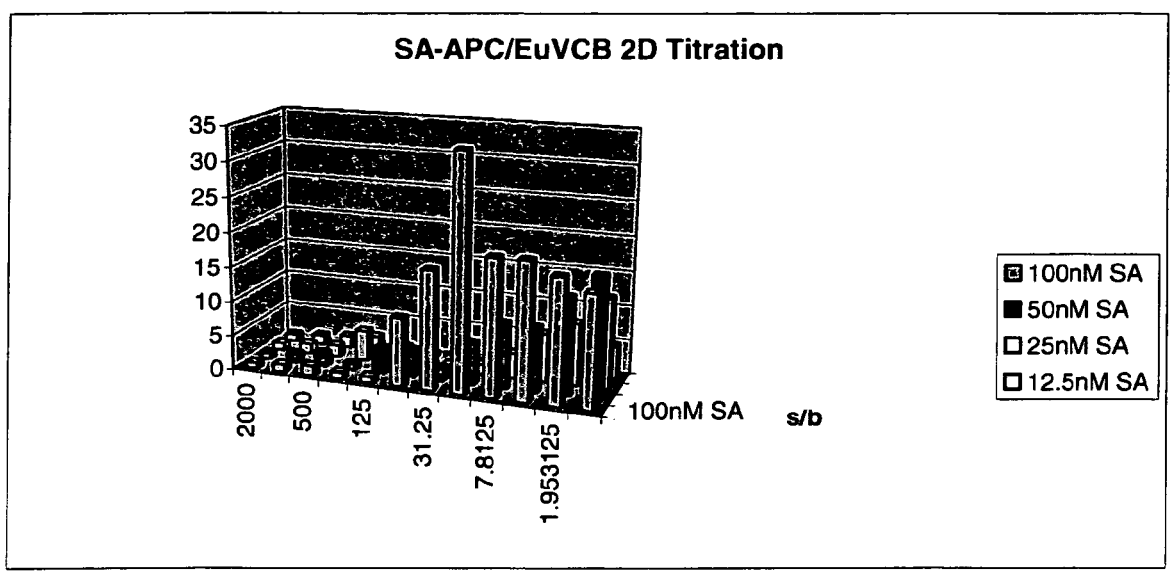

Ukrajinets, I.V., et al., "4-Hydroxy-2-Quinolines. XXI. 1H-2-oxo-4-hydroxyquinoline-3-carboxylic Alkylamides As a Novel Group of Antithyroid Drugs," Farmatsevtichnii Zhurnal (Kiev), 1995, (6) pp. 54-55.

Bezuglyi, P.A., "Amides of 4-Hydroxyquinoline-2-oxo-3-carboxylic Acid: Synthesis and Anticoagulant Activity," Khimiko-Farmatsevtischeskii Zhurnal, 1990, 24(4) pp. 31-32.

* cited by examiner

Determining linear range of HIF-OH detection
(biotHIF-OH binding curve, 1xHTRF buffer, 1.56nM RuVCB, 0.033ug/mL SAbeads)

Linear range (070204)
(1xHTRF buffer, 1.56nM RuVCB, 0.033ug/mL SAbeads)

SEQUENCE LISTING

<160> NUMBER OF SEQ ID NOS: 7

<210> SEQ ID NO 1
<211> LENGTH: 166
<212> TYPE: PRT
<213> ORGANISM: Homo sapiens

<400> SEQUENCE: 1

```
Met His His His His His His Glu Ala Gly Arg Pro Arg Pro Val Leu
  1               5                  10                  15

Arg Ser Val Asn Ser Arg Glu Pro Ser Gln Val Ile Phe Cys Asn Arg
             20                  25                  30

Ser Pro Arg Val Val Leu Pro Val Trp Leu Asn Phe Asp Gly Glu Pro
         35                  40                  45

Gln Pro Tyr Pro Thr Leu Pro Pro Gly Thr Gly Arg Arg Ile His Ser
     50                  55                  60

Tyr Arg Gly His Leu Trp Leu Phe Arg Asp Ala Gly Thr His Asp Gly
 65                  70                  75                  80

Leu Leu Val Asn Gln Thr Glu Leu Phe Val Pro Ser Leu Asn Val Asp
                 85                  90                  95

Gly Gln Pro Ile Phe Ala Asn Ile Thr Leu Pro Val Tyr Thr Leu Lys
            100                 105                 110

Glu Arg Cys Leu Gln Val Val Arg Ser Leu Val Lys Pro Glu Asn Tyr
        115                 120                 125

Arg Arg Leu Asp Ile Val Arg Ser Leu Tyr Glu Asp Leu Glu Asp His
    130                 135                 140

Pro Asn Val Gln Lys Asp Leu Glu Arg Leu Thr Gln Glu Arg Ile Ala
145                 150                 155                 160

His Gln Arg Met Gly Asp
                165
```

<210> SEQ ID NO 2

```
<211> LENGTH: 118
<212> TYPE: PRT
<213> ORGANISM: Homo sapiens

<400> SEQUENCE: 2

Met Asp Val Phe Leu Met Ile Arg Arg His Lys Thr Thr Ile Phe Thr
 1               5                  10                  15

Asp Ala Lys Glu Ser Ser Thr Val Phe Glu Leu Lys Arg Ile Val Glu
            20                  25                  30

Gly Ile Leu Lys Arg Pro Pro Asp Glu Gln Arg Leu Tyr Lys Asp Asp
        35                  40                  45

Gln Leu Leu Asp Asp Gly Lys Thr Leu Gly Glu Cys Gly Phe Thr Ser
    50                  55                  60

Gln Thr Ala Arg Pro Gln Ala Pro Ala Thr Val Gly Leu Ala Phe Arg
65                  70                  75                  80

Ala Asp Asp Thr Phe Glu Ala Leu Cys Ile Glu Pro Phe Ser Ser Pro
                85                  90                  95

Pro Glu Leu Pro Asp Val Met Lys Pro Gln Asp Ser Gly Ser Ser Ala
            100                 105                 110

Asn Glu Gln Ala Val Gln
        115

<210> SEQ ID NO 3
<211> LENGTH: 96
<212> TYPE: PRT
<213> ORGANISM: Homo sapiens

<400> SEQUENCE: 3

Met Tyr Val Lys Leu Ile Ser Ser Asp Gly His Glu Phe Ile Val Lys
 1               5                  10                  15

Arg Glu His Ala Leu Thr Ser Gly Thr Ile Lys Ala Met Leu Ser Gly
            20                  25                  30

Pro Gly Gln Phe Ala Glu Asn Glu Thr Asn Glu Val Asn Phe Arg Glu
        35                  40                  45

Ile Pro Ser His Val Leu Ser Lys Val Cys Met Tyr Phe Thr Tyr Lys
    50                  55                  60

Val Arg Tyr Thr Asn Ser Ser Thr Glu Ile Pro Glu Phe Pro Ile Ala
65                  70                  75                  80

Pro Glu Ile Ala Leu Glu Leu Leu Met Ala Ala Asn Phe Leu Asp Cys
                85                  90                  95

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Leu Asp Leu Glu Ala Leu Ala Pro Tyr Ile Pro Ala Asp Asp
 1               5                  10                  15

Phe Gln Leu Arg
        20

<210> SEQ ID NO 5
<211> LENGTH: 20
<212> TYPE: PRT
<213> ORGANISM: Artificial Sequence
<220> FEATURE:
```

-continued

```
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: hy-Pro

<400> SEQUENCE: 5

Asp Leu Asp Leu Glu Ala Leu Ala Pro Tyr Ile Pro Ala Asp Asp
 1               5                  10                  15

Phe Gln Leu Arg
            20

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Leu Glu Met Leu Ala Pro Tyr Ile Pro Met Asp Asp Asp Phe Gln
 1               5                  10                  15

Leu

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: hy-Pro

<400> SEQUENCE: 7

Asp Leu Glu Met Leu Ala Pro Tyr Ile Pro Met Asp Asp Asp Phe Gln
 1               5                  10                  15

Leu
```

QUINOLONE BASED COMPOUNDS EXHIBITING PROLYL HYDROXYLASE INHIBITORY ACTIVITY

This application claims the benefit of priority of U.S. Provisional Patent Application No. 60/748,577, filed Dec. 9, 2005, and U.S. Provisional Patent Application No. 60/785,358, filed Mar. 24, 2006.

The cellular transcription factor HIF (Hypoxia Inducible Factor) occupies a central position in oxygen homeostasis in a wide range of organisms and is a key regulator of responses to hypoxia. The genes regulated by HIF transcriptional activity can play critical roles in angiogenesis, erythropoiesis, hemoglobin F production, energy metabolism, inflammation, vasomotor function, apoptosis and cellular proliferation. HIF can also play a role in cancer, in which it is commonly upregulated, and in the pathophysiological responses to ischemia and hypoxia.

The HIF transcriptional complex comprises an αβ heterodimer: HIF-β is a constitutive nuclear protein that dimerizes with oxygen-regulated HIF-α subunits. Oxygen regulation occurs through hydroxylation of the HIF-α subunits, which are then rapidly destroyed by the proteasome. In oxygenated cells, the von Hippel-Lindau tumor suppressor protein (pVHL) binds to hydroxylated HIF-α subunits, thereby promoting their ubiquitin dependent proteolysis. This process is suppressed under hypoxic conditions, stabilizing HIF-α and promoting transcriptional activation by the HIF αβ complex. See, e.g., U.S. Pat. No. 6,787,326.

Hydroxylation of HIF-α subunits can occur on proline and asparagine residues and can be mediated by a family of 2-oxoglutarate dependent enzymes. This family includes the HIF prolyl hydroxylase isozymes (PHDs), which hydroxylate Pro 402 and Pro 564 of human HIF1α, as well as Factor Inhibiting HIF (FIH), which hydroxylates Asn 803 of human HIF1α. Inhibition of FIH or the PHDs leads to HIF stabilization and transcriptional activation. See, e.g., Schofield and Ratcliffe, Nature Rev. Mol. Cell Biol., Vol 5, pages 343-354 (2004).

Provided herein is at least one compound chosen from compounds of Formula I:

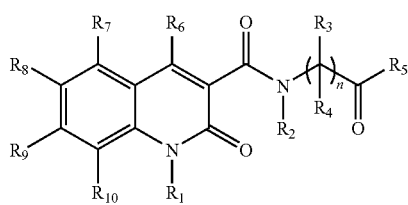

I a pharmaceutically acceptable salt thereof, a solvate thereof, a chelate thereof, a non-covalent complex thereof, a prodrug thereof, and mixtures of any of the foregoing, wherein:

n is 1 to 6;

$R_1$ is chosen from H, lower alkyl and substituted lower alkyl;

$R_2$ is chosen from H, lower alkyl and substituted lower alkyl;

$R_3$ and $R_4$ are independently chosen from H, lower alkyl, substituted lower alkyl, lower haloalkyl, substituted lower haloalkyl, or $R_3$ and $R_4$ can join together to form a 3 to 6 membered ring or a substituted 3 to 6 membered ring;

$R_5$ is chosen from OH, SH, $NH_2$, lower alkyl, substituted lower alkyl, lower alkoxy, substituted lower alkoxy, and sulfanyl;

$R_6$ is chosen from H, OH, SH, $NH_2$, $NHSO_2R_1$, and sulfonyl;

each of $R_7$, $R_8$, $R_9$ and $R_{10}$ is independently chosen from H, alkyl, substituted alkyl, alkenyl, substituted alkenyl, alkynyl, substituted alkynyl, alkoxy, substituted alkoxy, $NR_3R_4$, C(O)OH, $OR_{13}$, $SR_{13}$, $SO_2R_{13}$, CN, $NO_2$, halo, aryl, substituted aryl, heteroaryl, substituted heteroaryl, heteroarylalkyl, substituted heteroarylalkyl, heterocycloalkyl, substituted heterocycloalkyl, alkylsilyl, substituted alkylsilyl, alkynylsilyl, substituted alkynylsilyl, alkoxy, substituted alkoxy, alkoxycarbonyl, substituted alkoxycarbonyl, and $—X—R_{12}$, wherein:

$R_3$ and $R_4$ are defined above;

X is chosen from $—N(R_{11})—Y—$ and $—Y—N(R_{11})—$;

Y is chosen from C(O), $SO_2$, alkylene, substituted alkylene, alkenylene, substituted alkenylene, alkynylene, and substituted alkynylene;

$R_{11}$ is chosen from H, lower alkyl, and substituted lower alkyl, $R_{12}$ is chosen from H, heterocycloalkyl, substituted heterocycloalkyl, aryl, substituted aryl, heteroaryl, and substituted heteroaryl; and $R_{13}$ is chosen from H, alkyl, substituted alkyl, alkenyl, substituted alkenyl, alkynyl, substituted alkynyl and $NR_3R_4$;

wherein at least one of adjacent pairs $R_6$ and $R_7$, $R_7$ and $R_8$, $R_8$ and $R_9$, $R_9$ and $R_{10}$, and $R_{10}$ and $R_1$, can join together to form a 4 to 7 membered ring or a substituted 4 to 7 membered ring.

Also provided herein is a pharmaceutical composition comprising at least one pharmaceutically acceptable carrier, and a therapeutically effective amount of at least one compound described herein.

Further provided are pharmaceutical compositions comprising at least one pharmaceutically acceptable carrier, and a therapeutically effective amount of at least one compound described herein in combination with at least one additional compound such as an erythropoiesis stimulating agent or chemotherapeutic agent.

Additionally provided herein is a method of increasing HIF levels or activity in a subject by administering to the subject at least one compound described herein.

Further provided is a method of treating a condition where it is desired to modulate HIF activity comprising administering to a subject at least one compound described herein.

Also provided is a method of treating a hypoxic or ischemic related disorder in a subject comprising administering to a subject at least one compound described herein.

Also provided is a method of treating anemia in a subject comprising administering to a subject at least one compound described herein.

Further provided is a method of modulating the amount of HIF in a cell comprising contacting the cell with at least one compound described herein.

Additionally provided is a method of increasing the amount of hemoglobin F in a subject comprising administering to the subject at least one compound described herein.

Also provided is a method of modulating angiogenesis in a subject comprising administering to the subject at least one compound described herein.

Additionally provided is a method of treating at least one disease in a patient in need of such treatment comprising administering to the patient a therapeutically effective amount of at least one compound described herein.

Also provided is a method of inhibiting HIF hydroxylation in a subject comprising administering to the subject at least one compound described herein.

Further provided is an assay for the detection of HIF1α hydroxyproline residues comprising incubating a fluorochrome-labeled HIF1α polypeptide or fragment thereof with a VCB complex labeled with a rare earth element and detecting the binding of the VCB complex to HIF1α by homogeneous time-resolved FRET.

Also provided is an assay for the detection of HIF1α hydroxyproline residues comprising incubating a HIF1α polypeptide or fragment thereof with a VCB complex labeled with ruthenium and detecting the binding of the VCB complex to HIF1α by electrochemiluminescence.

Additional embodiments of the invention are set forth in the description which follows, or may be learned by practice of the invention.

FIG. 1 illustrates the ratio of fluorescence signal to background generated by the interaction of Eu-VCB with streptavidin-APC-hydroxyprolyl HIF1α peptide.

Figure 2:
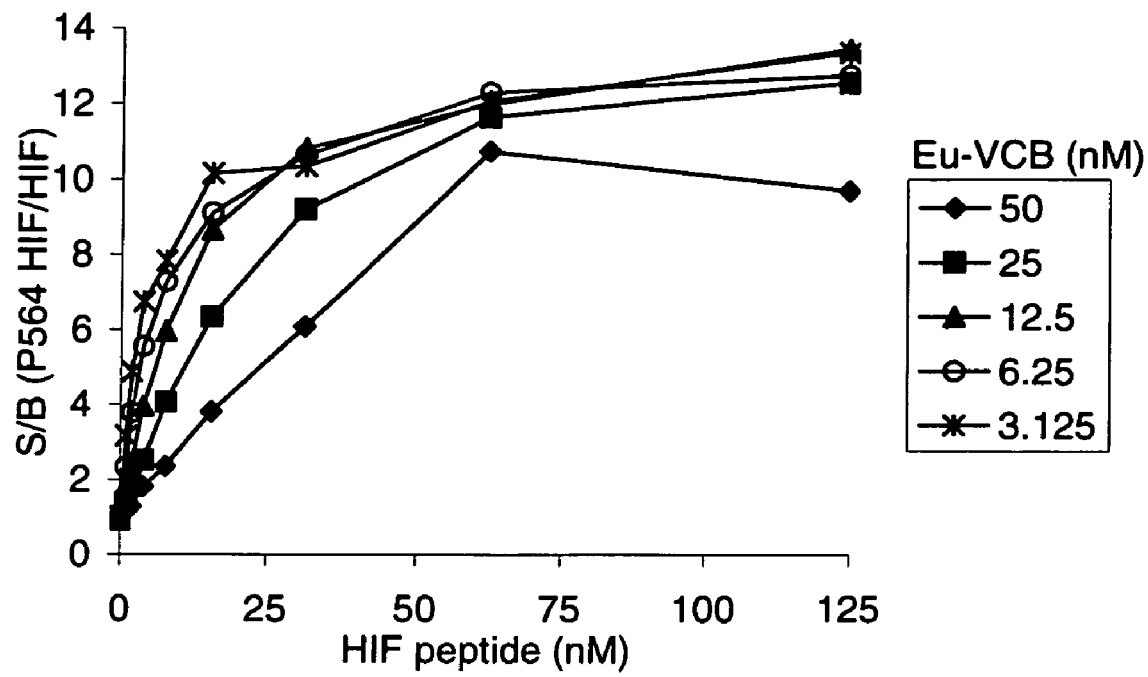
Figure 2:
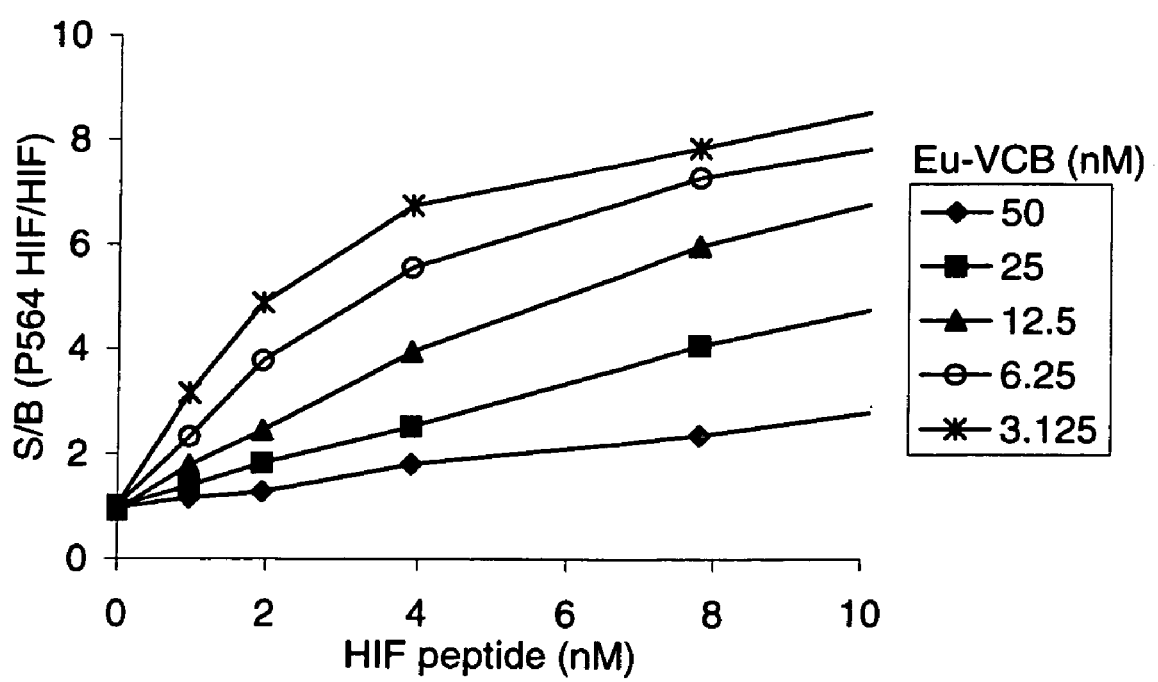

FIG. 2 illustrates the ratio of HTRF signal generated by the interaction of Eu-VCB with streptavidin-APC-hydroxyprolyl HIF1α peptide over background signal generated by the interaction of Eu-VCB with streptavidin-APC-HIF1α peptide (nonhydroxylated). Panel A illustrates a 0-125 nM peptide range. Panel B illustrates a 0-10 nM peptide range.

Figure 3:
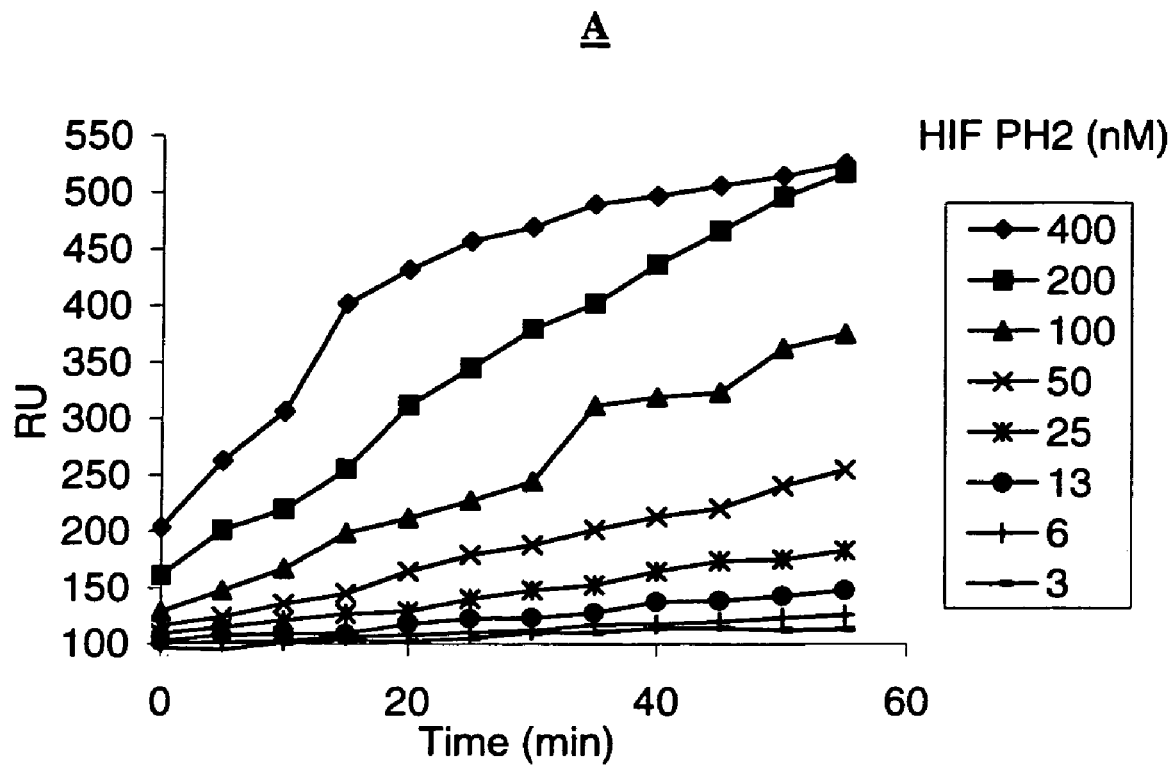
Figure 3:
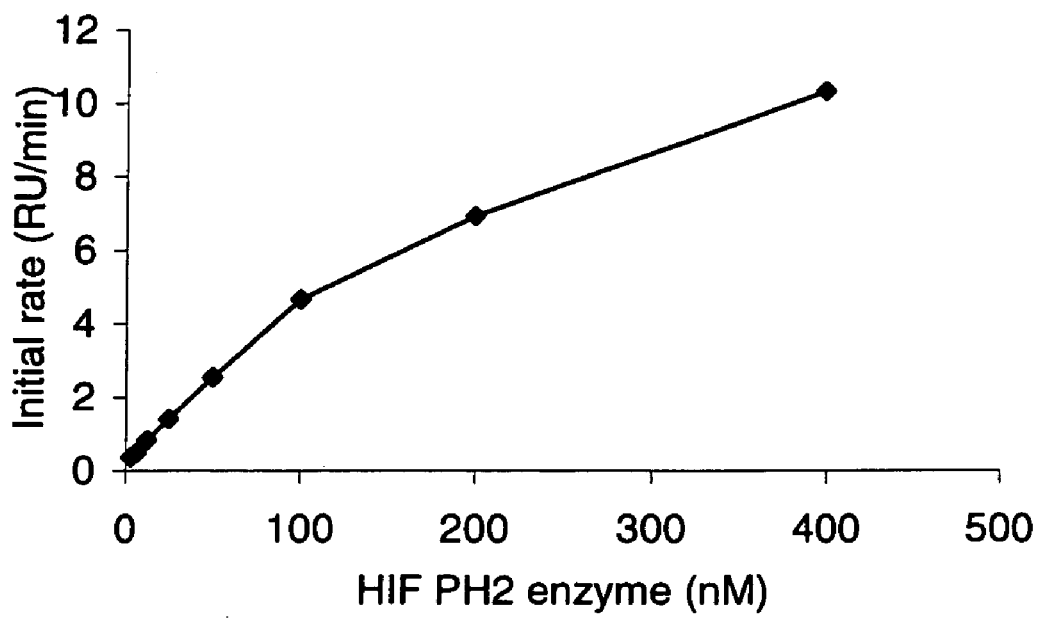

FIG. 3 illustrates VCB binding and HTRF detection for determining HIF PHD2 hydroxylation of a HIF1α peptide. Panel A illustrates a time course for the hydroxylation of the HIF1α peptide with increasing amounts of HIF PHD2 enzyme. Panel B illustrates initial rates with increasing enzyme concentrations.

Figure 4:
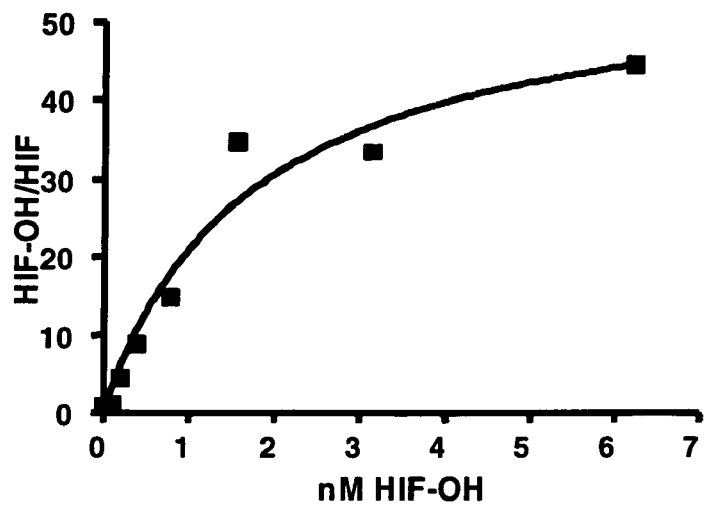
Figure 4:
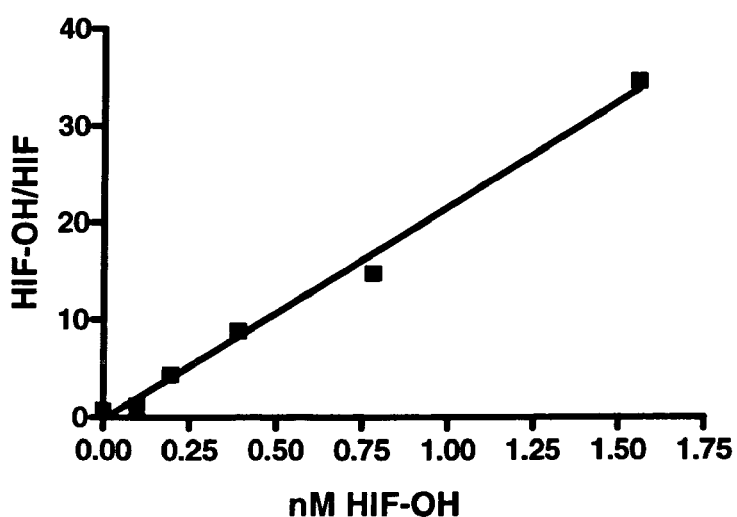

FIG. 4 illustrates the Ru-VCB/biotin-HIF-OH binding curve and linear range determination by ECL detection.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, when any variable occurs more than one time in a chemical formula, its definition on each occurrence is independent of its definition at every other occurrence. When the chemical structure and chemical name conflict, the chemical structure is determinative of the identity of the compound. The compounds of the present disclosure may contain one or more chiral centers and/or double bonds and therefore, may exist as stereoisomers, such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into the component enantiomers or stereoisomers using separation techniques or chiral synthesis techniques well known to the skilled artisan.

Compounds of Formula I include, but are not limited to optical isomers of compounds of Formula I, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds of Formula I include Z- and E-forms (or cis- and trans-forms) of compounds with double bonds. Where compounds of Formula I exists in various tautomeric forms, chemical entities of the present invention include all tautomeric forms of the compound.

Compounds of the present disclosure include, but are not limited to compounds of Formula I and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. As used henceforth, the term "compound" encompasses not only the compound itself, but also a pharmaceutically acceptable salt thereof, a solvate thereof, a chelate thereof, a non-covalent complex thereof, a prodrug thereof, and mixtures of any of the foregoing.

As noted above, prodrugs also fall within the scope of chemical entities, for example, ester or amide derivatives of the compounds of Formula I. The term "prodrugs" includes any compounds that become compounds of Formula I when administered to a patient, e.g., upon metabolic processing of the prodrug. Examples of prodrugs include, but are not limited to, acetate, formate, and benzoate and like derivatives of functional groups (such as alcohol or amine groups) in the compounds of Formula I.

The term "solvate" refers to the compound formed by the interaction of a solvent and a compound. Suitable solvates are pharmaceutically acceptable solvates, such as hydrates, including monohydrates and hemi-hydrates.

"Alkenyl" refers to an unsaturated branched, straight-chain or cyclic alkyl group having at least one carbon-carbon double bond derived by the removal of one hydrogen atom from a single carbon atom of a parent alkene. The group may be in either the Z- and E-forms (or cis or trans conformation) about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. In certain embodiments, an alkenyl group has from 2 to 20 carbon atoms and in other embodiments, from 2 to 6 carbon atoms, i.e. "lower alkenyl."

"Alkynyl" refers to an unsaturated branched or straight-chain having at least one carbon-carbon triple bond derived by the removal of one hydrogen atom from a single carbon atom of a parent alkyne. Typical alkynyl groups include, but are not limited to, ethynyl; propynyl; butenyl, 2-pentynyl, 3-pentynyl, 2-hexynyl, 3-hexynyl and the like. In certain embodiments, an alkynyl group has from 2 to 20 carbon atoms and in other embodiments, from 2 to 6 carbon atoms, i.e. "lower alkynyl."

"Alkoxy" refers to a radical —OR where R represents an alkyl, substituted alkyl, substituted cycloalkyl, substituted heterocycloalkyl, substituted aryl, or substituted heteroaryl group as defined herein. Representative examples include, but are not limited to, methoxy, ethoxy, propoxy, butoxy, cyclohexyloxy, and the like.

"Alkoxycarbonyl" refers to a radical —C(O)OR where R is as defined herein.

"Alkyl" refers to a saturated, branched or straight-chain monovalent hydrocarbon group derived by the removal of one hydrogen atom from a single carbon atom of a parent alkane. Typical alkyl groups include, but are not limited to, methyl, ethyl, propyls such as propan-1-yl, propan-2-yl, and cyclopropan-1-yl, butyls such as butan-1-yl, butan-2-yl, 2-methyl-propan-1-yl, 2-methyl-propan-2-yl, cyclobutan-1-yl, tert-butyl, and the like. In certain embodiments, an alkyl group comprises from 1 to 20 carbon atoms. As used herein the term "lower alkyl" refers to an alkyl group comprising from 1 to 6 carbon atoms.

"Aryl" refers to a monovalent aromatic hydrocarbon group derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. For example, aryl includes 5- and 6-membered carbocyclic aromatic rings fused to a 5- to 7-membered heterocycloalkyl ring containing 1 or more heteroatoms chosen from N, O, and S. In certain embodiments, an aryl group can comprise from 6 to 10 carbon atoms. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

"Arylalkyl" or "aralkyl" refers to an acyclic alkyl group in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkyl, arylalkenyl, and/or arylalkynyl is used. In certain embodiments, an arylalkyl group can be $(C_{6-30})$ arylalkyl, e.g., the alkyl group of the arylalkyl group can be $(C_{1-10})$ and the aryl moiety can be $(C_{5-20})$.

"Carbonyl" refers to a radical —C(O) group.

"Carboxy" refers to the radical —C(O)OH.

"Cyano" refers to the radical —CN.

"Cycloalkyl" refers to a saturated or unsaturated cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In certain embodiments, the cycloalkyl group can be $C_{3-10}$ cycloalkyl, such as, for example, $C_{3-6}$ cycloalkyl.

"Heterocycloalkyl" refers to a saturated or unsaturated, but non-aromatic, cyclic alkyl group in which one or more carbon atoms (and any associated hydrogen atoms) are independently replaced with the same or different heteroatom and its associated hydrogen atoms, where appropriate. Typical heteroatoms to replace the carbon atom(s) include, but are not limited to, N, P, O, S, and Si. Where a specific level of saturation is intended, the nomenclature "heterocycloalkanyl" or "heterocycloalkenyl" is used. Typical heterocycloalkyl groups include, but are not limited to, groups derived from epoxides, imidazolidine, morpholine, piperazine, piperidine, pyrazolidine, pyrrolidine, quinuclidine, tetrahydrofuran, tetrahydropyran and the like. Substituted heterocycloalkyl also includes ring systems substituted with one or more oxo (=O) or oxide (—O⁻) substituents, such as piperidinyl N-oxide, morpholinyl-N-oxide, 1-oxo-1-thiomorpholinyl and 1,1-dioxo-1-thiomorpholinyl.

"Disease" refers to any disease, disorder, condition, symptom, or indication.

"Halo" refers to a fluoro, chloro, bromo, or iodo group.

"Heteroaryl" refers to a monovalent heteroaromatic group derived by the removal of one hydrogen atom from a single atom of a parent heteroaromatic ring system. Heteroaryl encompasses:

5- to 7-membered aromatic, monocyclic rings containing one or more, for example, from 1 to 4, or in certain embodiments, from 1 to 3, heteroatoms chosen from N, O, and S, with the remaining ring atoms being carbon; and polycyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring.

For example, heteroaryl includes a 5- to 7-membered heteroaromatic ring fused to a 5- to 7-membered cycloalkyl ring and a 5- to 7-membered heteroaromatic ring fused to a 5- to 7-membered heterocycloalkyl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Heteroaryl does not encompass or overlap with aryl as defined above. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, the heteroaryl group can be between 5 to 20 membered heteroaryl, such as, for example, a 5 to 10 membered heteroaryl. In certain embodiments, heteroaryl groups can be those derived from thiophene, pyrrole, benzothiophene, benzofuran, indole, pyridine, quinoline, imidazole, oxazole, and pyrazine.

"Heteroarylalkyl" or "heteroaralkyl" refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl, and/or heteroarylalkynyl is used. In certain embodiments, the heteroarylalkyl group can be a 6 to 30 membered heteroarylalkyl, e.g., the alkanyl, alkenyl or alkynyl moiety of the heteroarylalkyl can be 1 to 10 membered and the heteroaryl moiety can be a 5 to 20-membered heteroaryl.

"Sulfonyl" refers to a radical —S(O)₂R where R is an alkyl, substituted alkyl, substituted cycloalkyl, substituted heterocycloalkyl, substituted aryl, or substituted heteroaryl group as defined herein. Representative examples include, but are not limited to methylsulfonyl, ethylsulfonyl, propylsulfonyl, butylsulfonyl, and the like.

"Sulfanyl" refers to a radical —SR where R is an alkyl, substituted alkyl, substituted cycloalkyl, substituted heterocycloalkyl, substituted aryl, or substituted heteroaryl group as defined herein that may be optionally substituted as defined herein. Representative examples include, but are not limited to, methylthio, ethylthio, propylthio, butylthio, and the like.

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient," "pharmaceutically acceptable carrier," or "pharmaceutically acceptable adjuvant" refer, respectively, to an excipient, carrier or adjuvant with which at least one compound of the present disclosure is administered. "Pharmaceutically acceptable vehicle" refers to any of a diluent, adjuvant, excipient or carrier with which at least one compound of the present disclosure is administered.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereoisomers."

"Subject" includes mammals and humans. The terms "human" and "subject" are used interchangeably herein.

"Substituted" refers to a group in which one or more hydrogen atoms are each independently replaced with the same or different substituent(s). Typical substituents include, but are not limited to, —X, —$R_{33}$, —OH, =O, $OR_{33}$, $CR_{33}$, —SH, =S, —$NR_{33}R_{34}$, =$NR_{33}$, $CX_3$, —$CF_3$, —CN, —$NO_2$, —$S(O)_2R_{33}$, —$OS(O_2)OH$, —$OS(O)_2R_{33}$, —$OP(O)(OR_{33})(OR_{34})$, —$C(O)R_{33}$, —$C(S)R_{33}$, —$C(O)OR_{33}$, —$C(O)NR_{33}R_{34}$, —C(O)OH, —$C(S)OR_{33}$, —$NR_{35}C(O)NR_{33}R_{34}$, —$NR_{35}C(S)NR_{33}R_{34}$, —$NR_{35}C(NR_{33})NR_{33}R_{34}$, —$C(NR_{33})NR_{33}R_{34}$, —$S(O)_2NR_{33}R_{34}$, —$NR_{35}S(O)_2R_{33}$, —$NR_{35}C(O)R_{33}$, and —$S(O)R_{33}$ where each X is independently a halo; each $R_{33}$ and $R_{34}$ are independently hydrogen, alkyl, substituted alkyl, aryl, substituted aryl, arylalkyl, substituted arylalkyl, cycloalkyl, substituted cycloalkyl, heterocycloalkyl, substituted heterocycloalkyl, heteroaryl, substituted heteroaryl, heteroarylalkyl, substituted heteroarylalkyl, —$NR_{35}R_{36}$, —$C(O)R_{35}$ or —$S(O)_2R_{35}$ or optionally $R_{33}$ and $R_{34}$ together with the atom to which $R_{33}$ and $R_{34}$ are attached form one or more heterocycloalkyl, substituted heterocycloalkyl, heteroaryl, or substituted heteroaryl rings; and $R_{35}$ and $R_{36}$ are independently hydrogen, alkyl substituted alkyl, aryl, substituted aryl, arylalkyl, substituted arylalkyl, cycloalkyl, substituted cycloalkyl, heterocycloalkyl, substituted heterocycloalkyl, heteroaryl, substituted heteroaryl, heteroarylalkyl or substituted heteroarylalkyl, or optionally $R_{35}$ and $R_{36}$ together with the nitrogen atom to which $R_{35}$ and $R_{36}$ are attached form one or more heterocycloalkyl, substituted heterocycloalkyl, heteroaryl, or substituted heteroaryl rings. In certain embodiments, a tertiary amine or aromatic nitrogen may be substituted with on or more oxygen atoms to form the corresponding nitrogen oxide.

"Therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

Embodiments of the present invention are directed to at least one compound of Formula I:

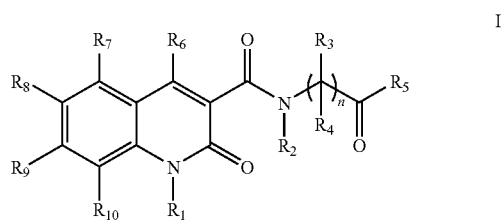

a pharmaceutically acceptable salt thereof, a solvate thereof, a chelate thereof, a non-covalent complex thereof, a prodrug thereof, and mixtures of any of the foregoing, wherein:

n is 1 to 6;

$R_1$ is chosen from H, lower alkyl and substituted lower alkyl;

$R_2$ is chosen from H, lower alkyl and substituted lower alkyl;

$R_3$ and $R_4$ are independently chosen from H, lower alkyl, substituted lower alkyl, lower haloalkyl, substituted lower haloalkyl, or $R_3$ and $R_4$ can join together to form a 3 to 6 membered ring or a substituted 3 to 6 membered ring;

$R_5$ is chosen from OH, SH, $NH_2$, lower alkyl, substituted lower alkyl, lower alkoxy, substituted lower alkoxy, and sulfanyl;

$R_6$ is chosen from H, OH, SH $NH_2$, $NHSO_2R_1$ and sulfonyl;

each of $R_7$, $R_8$, $R_9$ and $R_{10}$ is independently chosen from H, alkyl, substituted alkyl, alkenyl, substituted alkenyl, alkynyl, substituted alkynyl, alkoxy, substituted alkoxy, $NR_3R_4$, C(O)OH, $OR_{13}$, $SR_{13}$, $SO_2R_{13}$, CN, $NO_2$, halo, aryl, substituted aryl, heteroaryl, substituted heteroaryl, heteroarylalkyl, substituted heteroarylalkyl, heterocycloalkyl, substituted heterocycloalkyl, alkylsilyl, substituted alkylsilyl, alkynylsilyl, substituted alkynylsilyl, alkoxy, substituted alkoxy, alkoxycarbonyl, substituted alkoxycarbonyl, and —X—$R_{12}$, wherein:

$R_3$ and $R_4$ are defined above;

X is chosen from —N($R_{11}$)—Y— and —Y—N($R_{11}$)—;

Y is chosen from C(O), $SO_2$, alkylene, substituted alkylene, alkenylene, substituted alkenylene, alkynylene, and substituted alkynylene;

$R_{11}$ is chosen from H, lower alkyl, and substituted lower alkyl, $R_{12}$ is chosen from H, heterocycloalkyl, substituted heterocycloalkyl, aryl, substituted aryl, heteroaryl, and substituted heteroaryl; and $R_{13}$ is chosen from H, alkyl, substituted alkyl, alkenyl, substituted alkenyl, alkynyl, substituted alkynyl and $NR_3R_4$;

wherein at least one of adjacent pairs $R_6$ and $R_7$, $R_7$ and $R_8$, $R_8$ and $R_9$, $R_9$ and $R_{10}$, and $R_{10}$ and $R_1$ can join together to form a 4 to 7 membered ring or a substituted 4 to 7 membered ring.

In certain embodiments of compounds of Formula I, $R_1$ is chosen from a lower alkyl such as methyl or ethyl.

In certain embodiments of compounds of Formula I, $R_2$ is chosen from H.

In certain embodiments of compounds of Formula I, $R_3$ and $R_4$ are independently chosen from H, lower alkyl such as methyl or ethyl, substituted lower alkyl and substituted hydroxyalkyl such as hydroxymethyl.

In certain embodiments of compounds of Formula I, $R_5$ is chosen from OH, a lower alkoxy such as methoxy, ethoxy and propoxy, a substituted lower alkoxy and a primary amide.

In certain embodiments of compounds of Formula I, $R_6$ is chosen from H, OH and alkoxy.

In certain embodiments of compounds of Formula I, $R_3$ and $R_4$ join together to form a 3 to 6 membered ring or a substituted 3 to 6 membered ring. The 3 to 6 membered rings can comprise at least one heteroatom, such as at least two heteroatoms.

In certain embodiments of compounds of Formula I, $R_6$ and $R_7$ can join together to form a 4 to 7 membered ring or a substituted 4 to 7 membered ring. The 4 to 7 membered rings can comprise at least one heteroatom, such as at least two heteroatoms, and at least three heteroatoms.

In certain embodiments of compounds of Formula I, at least one of $R_7$, $R_8$, $R_9$ and $R_{10}$ is independently chosen from halo and a moiety substituted with at least one halo, such as trifluoromethyl.

In certain embodiments of compounds of Formula I, at least one of $R_7$, $R_8$, $R_9$ and $R_{10}$ is independently chosen from alkoxy or substituted alkoxy.

In certain embodiments of compounds of Formula I, at least one of $R_7$, $R_8$, $R_9$ and $R_{10}$ is independently chosen from alkylsilyl, substituted alkylsilyl, alkynylsilyl, and substituted alkynylsilyl.

In certain embodiments of compounds of Formula I, at least one of $R_7$, $R_8$, $R_9$ and $R_{10}$ is independently chosen from aryl, substituted aryl, heteroaryl, substituted heteroaryl, heterocycloalkyl, and substituted heterocycloalkyl, such as substituted pyridines, substituted pyrimidines, substituted pyrazines, substituted pyridazines, substituted tetrahydrofurans and substituted piperidines In certain embodiments of compounds of Formula I, at least one of $R_7$, $R_8$, $R_9$ and $R_{10}$ is independently chosen from H, alkyl, substituted alkyl, alkenyl, substituted alkenyl, alkynyl, and substituted alkynyl, such as isopropyl, cyclohexane, cyclopentane, cyclohexene and cyclopentene.

Examples of individual representative compounds of the present disclosure, and compounds comprised in compositions of the present disclosure, and used in methods of the present disclosure are listed in Table 1, which is included as FIG. 1 of this disclosure. Each compound listed in Table 1, i.e., Compounds 1-175, contains information directed to its structure, name, molecular weight, hydrogen NMR data and at least one method of synthesis.

In certain embodiments, compounds of the present disclosure inhibit prolyl hydroxylases such as HIF prolyl hydroxylases. The assays of the present disclosure may be used to determine the prolyl hydroxylase inhibitory activity of a compound.

In certain embodiments, compounds of the present disclosure modulate HIF levels or activity, for example, by stabilizing HIF.

Furthermore, compounds of the present disclosure can contain one or more chiral centers. Such compounds can be prepared or isolated as pure stereoisomers, i.e., as individual enantiomers or diastereomers, or as stereoisomer-enriched mixtures. All such stereoisomers, and enriched mixtures thereof, are included within the scope of the present disclosure. Pure stereoisomers, and enriched mixtures thereof, can be prepared using, for example, optically active starting materials or stereoselective reagents well-known in the art. Alternatively, racemic mixtures of such compounds can be separated using, for example, chiral column chromatography, chiral resolving agents and the like.

Certain embodiments of the present disclosure are directed to a pharmaceutical composition comprising at least one pharmaceutically acceptable excipient, and a therapeutically effective amount of at least one compound described herein. The at least one compound can be present in an amount effective for the treatment of at least one disease chosen from ischemia, anemia, wound healing, auto-transplantation, allo-transplantation, xeno-transplantation, systemic high blood pressure, thalassemia, diabetes, cancer and an inflammatory disorder.

Other embodiments of the present disclosure are directed to a method of treating a condition where it is desired to modulate HIF activity comprising administering to a subject at least one compound described herein. The condition can be chosen from at least one of ischemia, anemia, wound healing, auto-transplantation, allo-transplantation, xeno-transplantation, systemic high blood pressure, thalassemnia, diabetes, cancer and an inflammatory disorder.

A further embodiment is directed to a method of treating at least one disease in a patient in need of such treatment comprising administering to the patient a therapeutically effective amount of at least one compound described herein. The at least one disease can be chosen from ischemia, anemia, wound healing, auto-transplantation, allo-transplantation, xeno-transplantation, systemic high blood pressure, thalassemia, diabetes, cancer and an inflammatory disorder.

Other embodiments of the present disclosure are directed to assays for the detection of hydroxyprolyl HIF1α proteins or fragments thereof comprising incubating a fluorochrome-labeled HIF1α polypeptide or fragment thereof with a VCB complex labeled with a rare earth element and detecting the binding of the VCB complex to HIF1α by homogeneous time-resolved FRET. In certain embodiments, the fluorochrome may be allophycocyanin. In other embodiments, the rare earth element may be europium.

Additional embodiments are directed to assays for the detection of hydroxyprolyl HIF1α proteins or fragments thereof comprising incubating a HIF1α polypeptide or fragment thereof with a VCB complex labeled with ruthenium and detecting the binding of the VCB complex to HIF1α by electrochemiluminescence. In certain embodiments, the HIF1α polypeptide or fragment thereof may be bound to a solid support.

The assays of the present disclosure may also be used to detect the hydroxylation of HIF1α proteins or fragments thereof by HIF prolyl hydroxylases.

Further embodiments of the present disclosure are directed to assays for inhibitors of HIF prolyl hydroxylases.

The compounds of the present invention can be produced by one or more of the following general reaction schemes.

General Scheme I

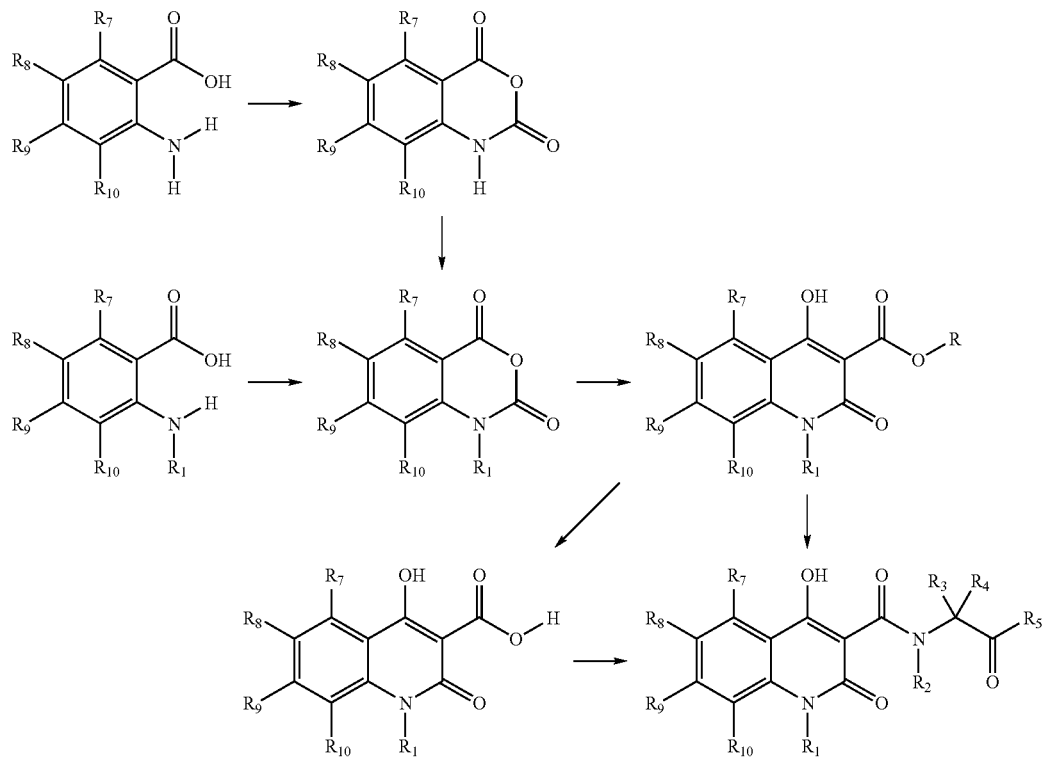

General Scheme II

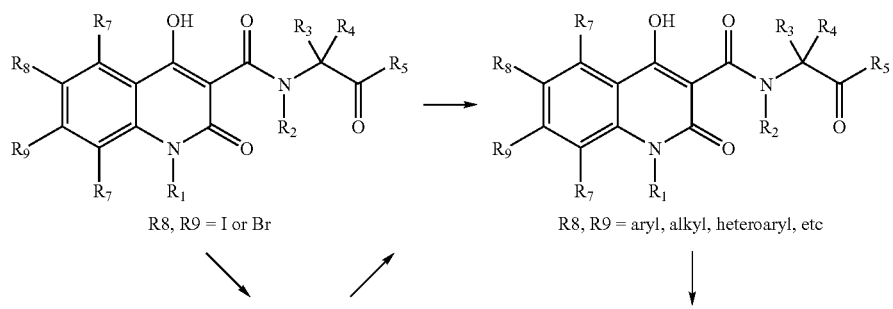

-continued

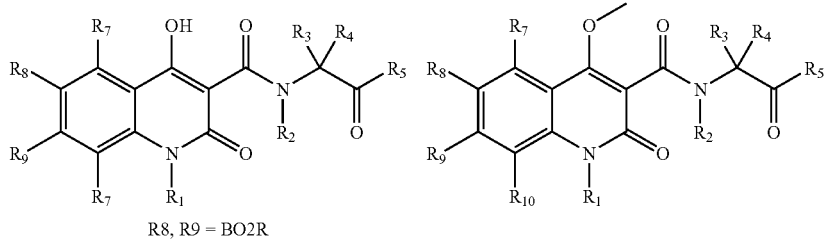

R8, R9 = BO2R

General Scheme III

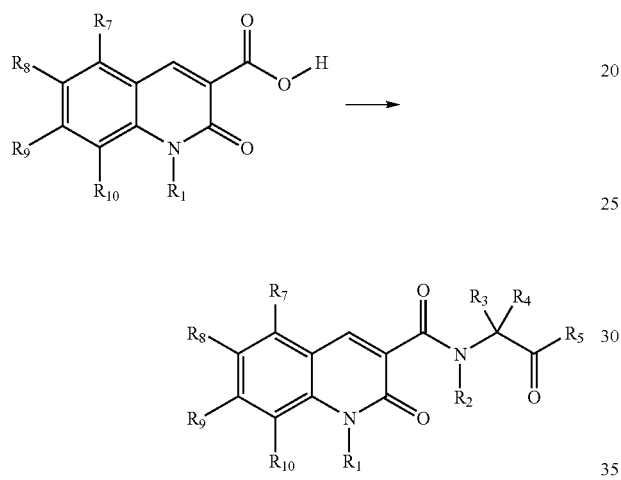

The following are examples of methods that can be used to produce intermediates to and compounds of the present invention.

Method 1:
5-Iodo-2-(methylamino)benzoic acid

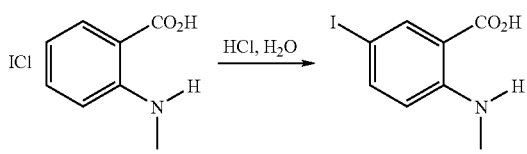

In a 1 L 3-neck flask was added 2-(methylamino)benzoic acid (40 g, 265 mmol), water (300 ml), and Hydrochloric acid (26.7 ml, 871 mmol). A solution of iodine monochloride was prepared by adding iodine monochloride (43 g, 265 mmol) to a cooled solution (0° C.) of Hydrochloric acid (45 ml, 1469 mmol) and water (167 ml, 9272 mmol). The iodine monochloride solution was added rapidly to the stirred solution of the 2-(methylamino)benzoic acid. The mixture was allowed to stir for 2 hrs, filtered on a medium frit funnel and the solids washed with water and dried under vacuum to give a quantitative yield of the product as a light-green powder. Ref. McDowell, R. S. et al, JACS, 1994, 116, 5077-5083

Method 2:
6-Iodo-1-methyl-1H-benzo[d][1,3]oxazine-2,4-dione

To a stirred solution of 5-iodo-2-(methylamino)benzoic acid (10 g, 36 mmol), sodium carbonate (4 g, 36 mmol) and water (130 ml, 7218 mmol), cooled to 0° C., was slowly added, via addition funnel, a 2M phosgene (18 ml, 36 mmol) solution in toluene. After 2 hrs, the precipitated product was isolated by filtration. The solids were washed with 100 ml of water, 150 ml of a 1:1 mixture ethanol and ether, 100 ml of ether, and dried under vacuum to give the desired product. Yield=7.15 g.

Method 3:
5-chloro-1H-benzo[d][1,3]oxazine-2,4-dione

In a 250 mL round-bottom flask under $N_2$ was dissolved 2-amino-6-chlorobenzoic acid (11.69 g, 68 mmol) in 100 mL of 1,4-dioxane. The solution was cooled to 0° C. and to this solution was added phosgene (36 ml, 68 mmol) via a dropping funnel. The reaction mixture was stirred for 24 hours allowing to warm to 23° C. (rt). The resulting white solid was filtered off and washed with 1,4-dioxane and $Et_2O$. Yield=12.5 g, 93%

Method 4:
6-Bromo-1-methyl-1H-benzo[d][1,3]oxazine-2,4-dione

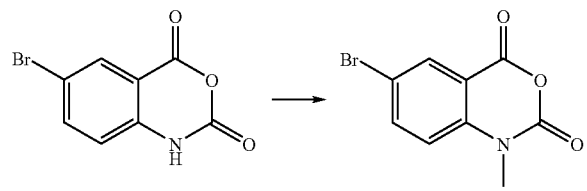

5-bromoisatoic anhydride (3 g, 12 mmol) was stirred in 50 mL of DMF at 0° C. and sodium hydride (60% dispersion in mineral oil) (0.4 g, 15 mmol) was added in portions, with stirring for 1 hour at room temperature. Iodomethane (0.8 mL, 12 mmol) was added drop wise and the reaction mixture was allowed to stir for 4 hours. Water (50 mL) was added slowly and 50 mL of Dichloromethane (DCM) was also added. A white solid precipitated out and was filtered off. The layers were separated layers. Aqueous layer extracted with DCM (2×25 ml). The combined organic layers were extracted with water (4×25 ml) and once with brine (25 ml). The organic layer was dried with MgSO4 and the solvent removed. The residue was purified by flash chromatography (0-3% MeOH/DCM) to afford 1.57 g of product. Yield 49%

Method 5:
7-Bromo-1-methyl-1H-benzo[d][1,3]oxazine-2,4-dione

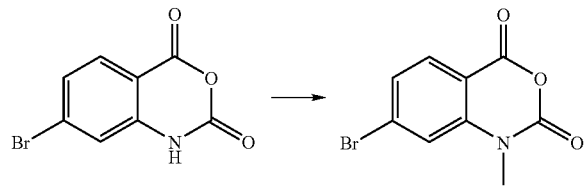

Sodium hydride (0.47 g, 12 mmol) was added to a 3 neck 250 mL RBF under nitrogen and then washed with hexanes. Once the hexanes were decanted, N,N-dimethylformamide (20.0 mL, 11 mmol) was added. The resulting mixture was cooled to 0° C. using an ice-water bath, and then 7-bromo-1H-benzo[d][1,3]oxazine-2,4-dione (2.7 g, 11 mmol) was added in one batch. After stirring at room temperature for 1 hour, iodomethane (0.70 mL, 11 mmol) was added dropwise to the yellow solution, and the reaction mixture was stirred for 16 hours. Water (50 mL) was added, and the resulting precipitate that formed was collected via filtration. The solid washed with additional water (100 mL), followed by ether (100 mL). Drying in a vacuum oven overnight at 50° C. afforded the desired product as an off-white solid (2.1 g, 74% yield).

Method 6:
methyl 1-methyl-2,4-dioxo-2,4-dihydro-1H-benzo[d][1,3]oxazine-7-carboxylate

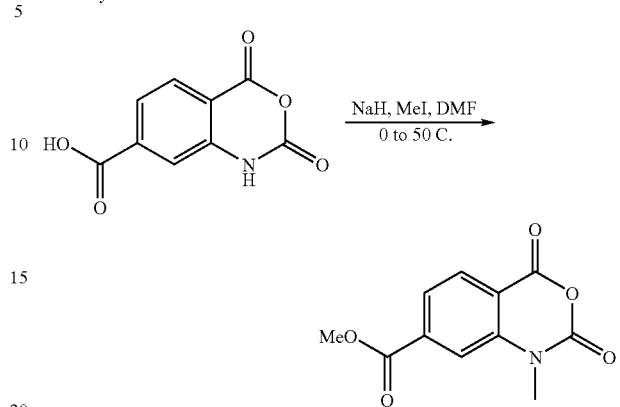

Sodium hydride (0.51 g, 21 mmol) was added to chilled (0° C.) DMF (40 ml). The 2,4-dioxo-2,4-dihydro-1H-benzo[d][1,3]oxazine-7-carboxylic acid (2.0 g, 9.7 mmol) was added to this mixture and stirred at 0° C. until hydrogen gas evolution (vigorous) ceased. A yellow suspension resulted. To this mixture, iodomethane (1.2 ml, 19 mmol) was then added and the mixture was warmed to room temperature, followed by heating to 50° C. for 30 min. The mixture was cooled to 0° C. and water was added slowly followed by dichloromethane. The layers were separated and the aqueous layer was extracted with dichloromethane 3×. The combined organic layers were washed sat. NaHCO3 (10 ml) 2× with H2O, and sat. NaCl (15 ml). The organic layer was dried over MgSO4, filtered and concentrated to give a yellow solution in DMF which was used without purification.

Method 7:
Ethyl 4-hydroxy-6-iodo-1-methyl-2-oxo-1,2-dihydroquinoline-3-carboxylate

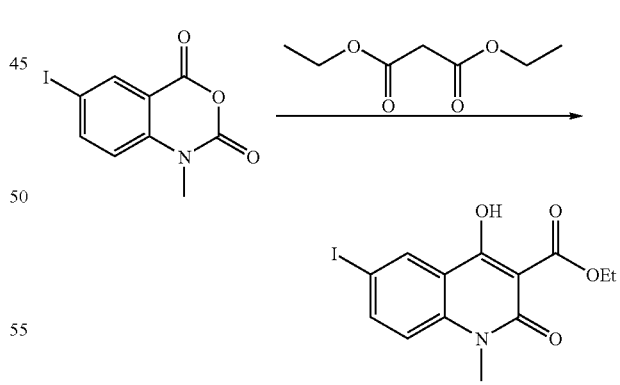

60% sodium hydride (1.2 ml, 28 mmol) was added portionwise to a mixture of diethyl ester malonic acid (17 ml, 110 mmol) and N,N-Dimethylformamide (75 ml) with stirring at room temperature. A mixture of 6-iodo-1-methyl-1H-benzo[d][1,3]oxazine-2,4-dione (7.12 g, 23 mmol) and N,N-Dimethylformamide (75 ml) was added to this solution followed by stirring at 120° C. for 2.5 hours. The precipitate that formed was collected by filtration and dissolved in water and 30% HCl was added to the mixture. The precipitated crystals were collected by filtration and dried to give the desired product. Yield=3.3 g.

Method 8:
tert-Butyl 4-hydroxy-6-iodo-1-methyl-2-oxo-1,2-dihydroquinoline-3-carboxylate

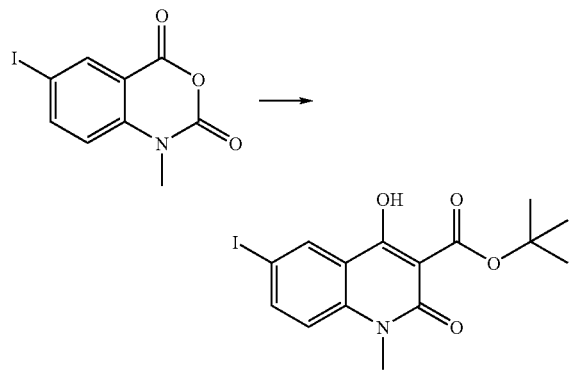

To a solution of tert-butyl malonate (5 ml, 20 mmol) in 1,4-Dioxane (70 ml) was added 60% Sodium hydride (0.8 g, 35 mmol) in portions. The mixture was stirred at room temperature for 45 min. then a solution of 6-iodo-1-methyl-1H-benzo[d][1,3]oxazine-2,4-dione (6.1 g, 20 mmol) in 1,4-Dioxane (40 ml) was added. The mixture was placed in an oil bath at 60° C. and the bath temp was raised to 120° C. over a period of 20 min after which stirring was continued for 90 min. The solvent was removed on a roto-evaporator and cold water (300 ml) was added to the residue. The mixture washed with DCM (100 ml) then the aqueous phase was acidified with 2N HCl. The organic layer was extracted into DCM (2×100 ml) and after drying over MgSO4 the solvent was removed on a roto-evaporator. Yield=4.1 g.

Method 9:
Methyl 7-bromo-4-hydroxy-1-methyl-2-oxo-1,2-dihydroquinoline-3-carboxylate

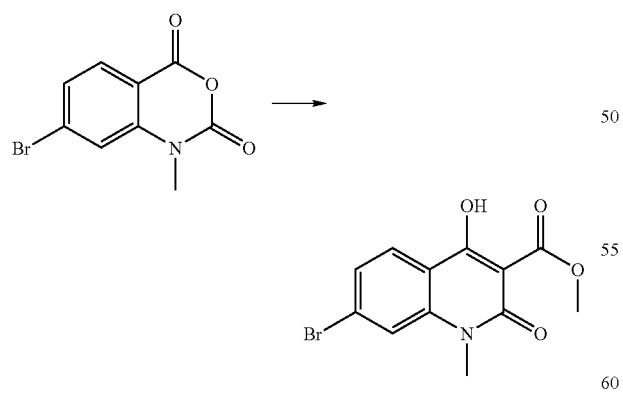

To a 50 mL RBF was added sodium hydride (0.15 g, 3.7 mmol) and N,N-dimethylformamide (50 mL, 3.1 mmol) under nitrogen. The mixture was cooled with an ice-water bath for 10 min, and then dimethyl malonate (6.4 mL, 56 mmol) was added over 3 min. A mixture of 7-bromo-1-methyl-1H-benzo[d][1,3]oxazine-2,4-dione (0.80 g, 3.1 mmol) in DMF (5.0 mL) was added, and then the reaction was placed in oil bath at 120° C. for 3 hours. The reaction was cooled to room temperature, and water (25 mL) was added to the mixture. A white solid was collected by filtration and washed with water (100 mL), followed by ether (100 mL). The white solid was placed in vacuum oven at 50° C. for 6 h to afford the desired product as a white solid (0.65 g, 67%).

Method 10:
3-benzyl 7-methyl 4-hydroxy-1-methyl-2-oxo-1,2-dihydroquinoline-3,7-dicarboxylate

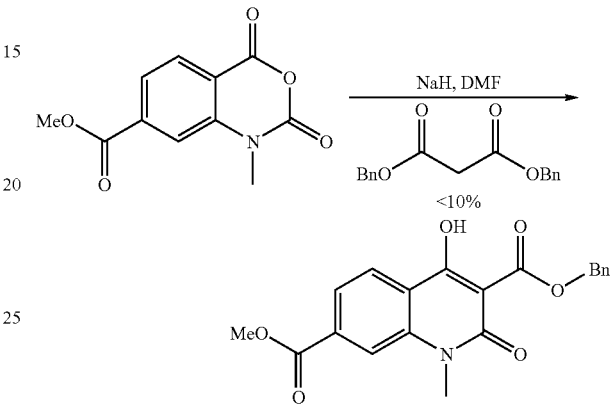

To a solution of dibenzyl malonate (2.99 ml, 11.9 mmol) in DMF (41 ml) was added sodium hydride in portions. The cloudy grey mixture was stirred at room temperature for 20 min after which time a clear solution resulted. The solution was further stirred at 120° C. for 20 min before adding a solution of methyl 1-methyl-2,4-dioxo-2,4-dihydro-1H-benzo[d][1,3]oxazine-7-carboxylate (2.82 g, 11.9 mmol) in DMF (41 ml). The resulting yellow solution was stirred at 120° C. for 3 hrs. The reaction mixture was cooled to room temperature, 2N HCl and EtOAc were added and the layers were separated. The aqueous layer was extracted with EtOAc 3×, the combined organics were washed with H2O (1×) followed by sat. NaCl (2×). The organic phase was then dried over MgSO4, filtered and concentrated to give a yellow solid. Purification was performed by ISCO using 10% to 50% Hex/EtOAc gradient, 40 g column to give 300 mg of a yellow solid.

Method 11:
4-Hydroxy-6-iodo-1-methyl-2-oxo-1,2-dihydroquinoline-3-carboxylic acid

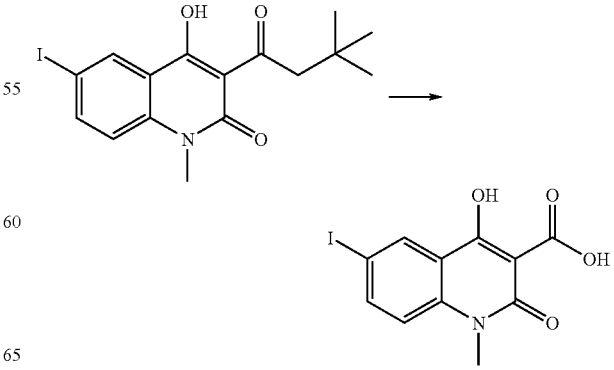

To a solution of tert-butyl 4-hydroxy-6-iodo-1-methyl-2-oxo-1,2-dihydroquinoline-3-carboxylate (4.1 g, 10 mmol) and Acetonitrile (20 ml), cooled in an ice bath, was added 70% perchloric acid (0.2 ml) and the mixture was stirred 30 sec. A yellow solid was filtered. Yield=0.5 g.

Method 12:
4-hydroxy-7-(methoxycarbonyl)-1-methyl-2-oxo-1,2-dihydroquinoline-3-carboxylic acid

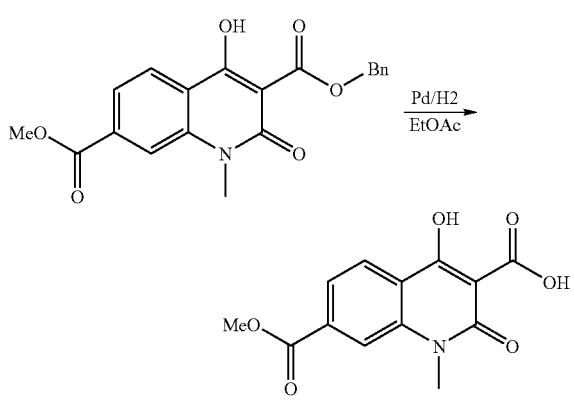

Palladium, 10 wt. % on activated carbon, (5.1 mg, 48 µmol) was added to a solution of 3-benzyl 7-methyl 4-hydroxy-1-methyl-2-oxo-1,2-dihydroquinoline-3,7-dicarboxylate (88 mg, 240 µmol) in ethyl acetate (19 ml) and brought under an atmosphere of $H_2$ while stirring vigorously. After the reaction was complete, the mixture was filtered through a Celite pad, rinsing with EtOAc/DCM to give an off-white powder (59 mg, 89%) which was used without further purification.

Method 13:
methyl 3-((2-(benzyloxy)-2-oxoethyl)carbamoyl)-4-hydroxy-1-methyl-2-oxo-1,2-dihydroquinoline-7-carboxylate

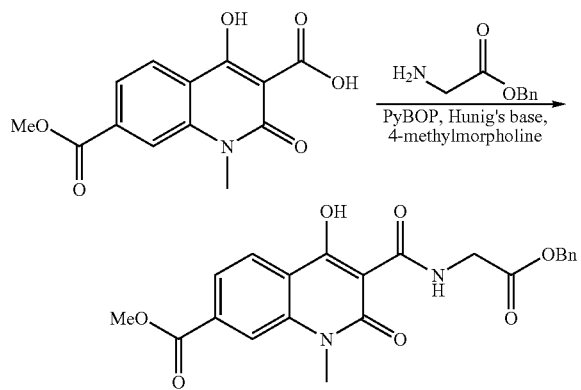

4-hydroxy-7-(methoxycarbonyl)-1-methyl-2-oxo-1,2-dihydroquinoline-3-carboxylic acid (107 mg, 386 µmol), glycine benzyl ester hydrochloride (117 mg, 579 µmol), pybop (603 mg, 1158 µmol), and diisopropylethylamine (403 µl, 2316 µmol) were dissolved in DMF and stirred at room temperature for 24 hours. The reaction mixture was diluted with $H_2O$ and DCM, the layers were separated and the aqueous layer was extracted with DCM (3×), the organics were washed with $H_2O$ (2×) and dried over $MgSO_4$, filtered and concentrated to yield a yellow solid. Flash column chromatography was performed using 2:1 Hex/EtOAc to give 45 mg of desired product.

Method 14:
Ethyl 2-(4-hydroxy-6-iodo-1-methyl-2-oxo-1,2-dihydroquinoline-3-carboxamido)acetate (glycine methyl ester or glycine t-butyl ester can also be used)

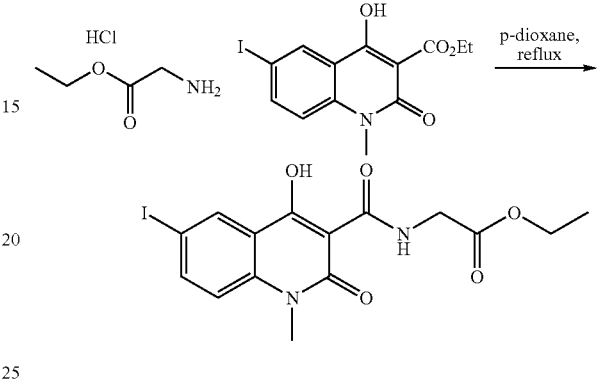

A solution of ethyl 4-hydroxy-6-iodo-1-methyl-2-oxo-1,2-dihydroquinoline-3-carboxylate (0.5 g, 1 mmol), glycine ethyl ester hydrochloride (0.2 g, 1 mmol) and 1,4-Dioxane (30 ml) in a 100 ml round-bottom flask, equipped with a short-path distillation head, was heated to 120° C. After 7 hrs, reaction was complete. The solvent was completely distilled over. A tan solid residue washed with EtOAc and concentrated on a roto-evaporator, then on high vacuum, for 15 hrs. A tan solid washed with DCM and a white solid was filtered off. The filtrate was concentrated on a roto-evaporator to give a light tan solid. Yield=0.4 g.

Method 15:
Methyl 2-(4-hydroxy-6-iodo-1-methyl-2-oxo-1,2-dihydroquinoline-3-carboxamido)acetate (glycine methyl ester or glycine t-butyl ester can also be used)

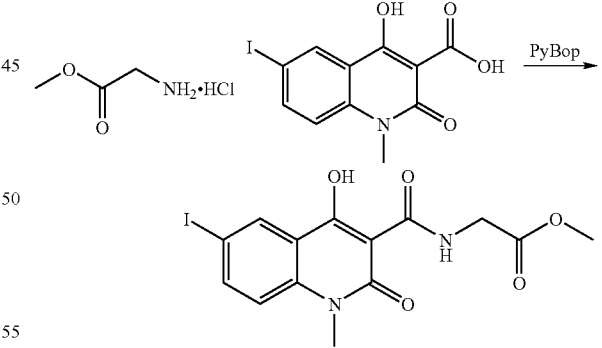

To a 100 ml rb flask was added 4-hydroxy-6-iodo-1-methyl-2-oxo-1,2-dihydroquinoline-3-carboxylic acid (0.5 g, 1 mmol), glycine methyl ester hydrochloride (0.3 g, 2 mmol), Pybop (1 g, 2 mmol), N,N-Dimethylformamide (10 ml) and Triethylamine (0.6 ml, 4 mmol), and the mixture was stirred at room temperature. After 4 hrs, additional glycine methyl ester hydrochloride (0.3 g, 2 mmol) and Triethylamine (0.6 ml, 4 mmol) were added. After 1 hour, more Pybop (1 g, 2 mmol) was added. The mixture was stirred for 3 days, and then a white solid was filtered. Yield=0.28 g.

Method 16:
(S)-methyl 2-(4-hydroxy-8-methoxy-1-methyl-2-oxo-1,2-dihydroquinoline-3-carboxamido)propanoate

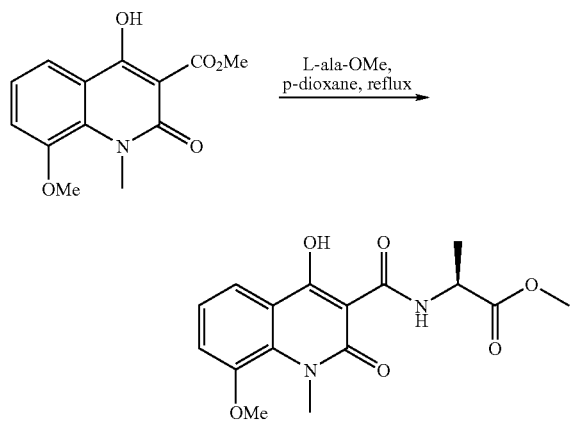

In a 35 mL sealed vial under $N_2$ was suspended methyl 4-hydroxy-8-methoxy-1-methyl-2-oxo-1,2-dihydroquinoline-3-carboxylate (0.50 g, 1.9 mmol) in 1,4-dioxane (15 mL). To this solution was added L-alanine methyl ester hydrochloride (0.29 g, 2.1 mmol) and the reaction mixture was stirred at 120° C. overnight (18 h). The solution was removed from the heat and filtered over a fine frit funnel to remove any undissolved starting material. The filtrate was concentrated in vacuo and the remaining precipitate was suspended in $Et_2O$, filtered and washed with $Et_2O$ and dried to provide a light yellow solid. Yield=0.40 g, 63%.

Method 17:
Methyl 2-(1-ethyl-4-hydroxy-2-oxo-1,2-dihydroquinoline-3-carboxamido)acetate

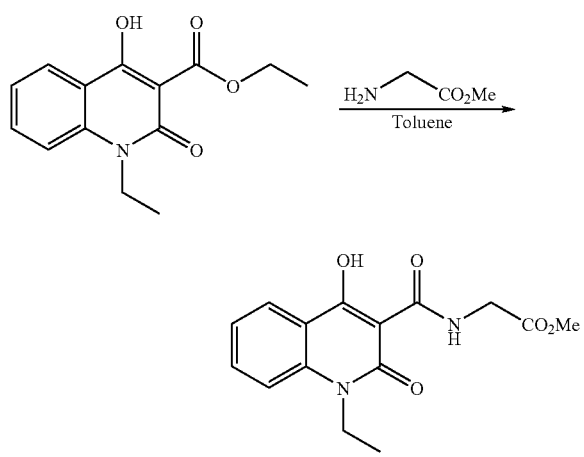

In 4 mL of toluene in a microwave vial, ethyl 1-ethyl-4-hydroxy-2-oxo-1,2-dihydroquinoline-3-carboxylate (0.380 g, 1 mmol), glycine methyl ester hydrochloride (0.5 g, 4 mmol) was microwaved at 180° C. for 3 minutes and then purified by silica flash chromatography with a 1-5% MeOH/DCM gradient to afford 0.050 g. Yield: 11%

Method 18:
Ethyl 2-(4-hydroxy-1-methyl-2-oxo-6-(4,4,5,5-tetramethyl-1,3,2-dioxaborolan-2-yl)-1,2-dihydroquinoline-3-carboxamido)acetate

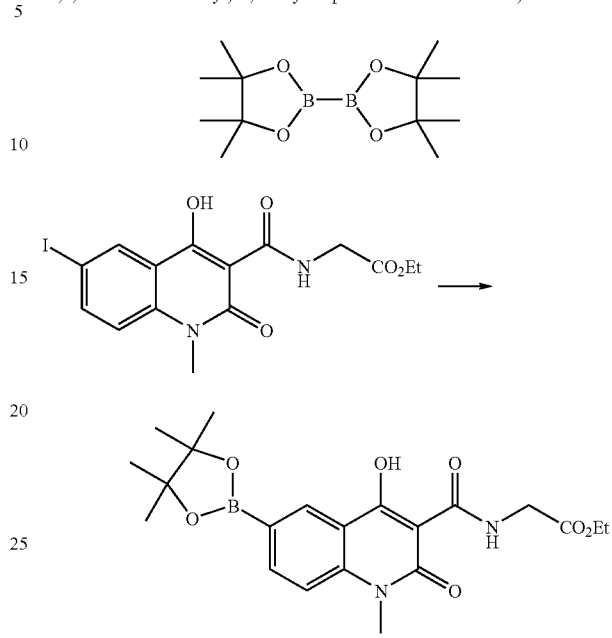

A mixture of ethyl 2-(4-hydroxy-6-iodo-1-methyl-2-oxo-1,2-dihydroquinoline-3-carboxamido)acetate (5 g, 12 mmol), bis(pinacolato)diboron (3 g, 13 mmol), 1,1'-bis(diphenylphosphino)ferrocene-palladium dichloride (0.3 g, 0.5 mmol), acetic acid, potassium salt (1 ml, 23 mmol), and 1,4-Dioxane (100 ml) was heated to 85-95° C. under an atmosphere of nitrogen. After 44 hrs, cooled reaction mixture and filtered off purplish-beige solid. The filtrate was concentrated on a roto-evaporator and treated with EtOH. A tan solid was filtered off and washed with ether. A second crop was obtained from the filtrate mixture. Yield=2.5 g.

Method 19:
Ethyl 2-(4-hydroxy-1-methyl-2-oxo-6-phenyl-1,2-dihydroquinoline-3-carboxamido)acetate

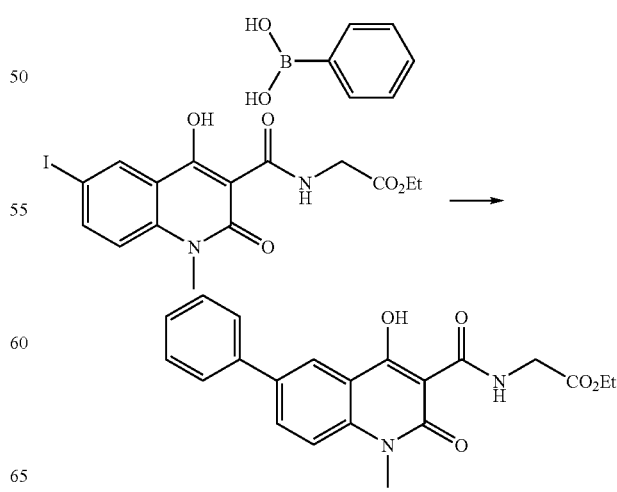

A solution of ethyl 2-(4-hydroxy-6-iodo-1-methyl-2-oxo-1,2-dihydroquinoline-3-carboxamido)acetate (200 mg, 465 μmol), phenylboronic acid (85 mg, 697 μmol), 2M Sodium carbonate (0.7 ml, 1395 μmol), Tetrakis(triphenylphosphine) palladium(0) (5 mg, 5 μmol) and N,N-Dimethylformamide (10 ml) was stirred at 100° C. After 8 hrs, an additional equivalent of the phenyl boronic acid was added, and the mixture was stirred for 15 hrs. The reaction mixture was concentrated on a roto-evaporator and extracted with EtOAc. This product was then washed with water and brine, then dried with MgSO4 and concentrated on a roto-evaporator to give the crude product as a red-orange oil. The crude product was purified by silica flash chromatography (10-75% EtOAc: Hex step gradient) to give the desired product as a white solid. Yield=120 mg. In some cases, ester hydrolysis was observed and the carboxylic acid was isolated.

Method 20:
Ethyl 2-(6-(6-chloropyrimidin-4-yl)-4-hydroxy-1-methyl-2-oxo-1,2-dihydroquinoline-3-carboxamido)acetate

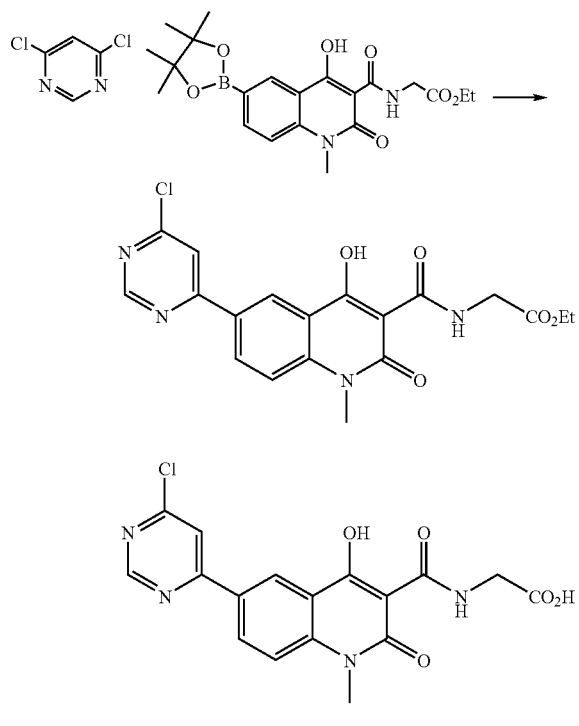

To a 10 ml reaction vial was charged ethyl 2-(4-hydroxy-1-methyl-2-oxo-6-(4,4,5,5-tetramethyl-1,3,2-dioxaborolan-2-yl)-1,2-dihydroquinoline-3-carboxamido)acetate (200 mg, 465 μmol) in 1,4-dioxane (5 ml), 4,6-dichloropyrimidine (69 mg, 465 μmol), tetrakis(triphenylphosphine) palladium(0) (27 mg, 23 μmol) and sodium carbonate (0.7 ml, 1395 μmol), and the reaction vial was heated to 70° C. After reaction was complete, the reaction mixture was concentrated on a roto-evaporator, extracted with EtOAc, washed with water and brine (3× ea.) then dried with MgSO4 and concentrated on a roto-evaporator. The yellow solid washed with EtOH and filtered and the solid washed with ether. Yield=55 mg.

Method 21:
Methyl 2-(7-(3,5-dimethylisoxazol-4-yl)-4-hydroxy-1-methyl-2-oxo-1,2-dihydroquinoline-3-carboxamido)acetate

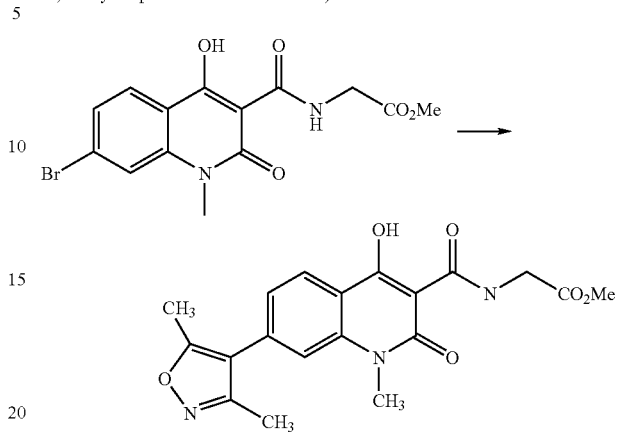

A mixture of methyl 2-(7-bromo-4-hydroxy-1-methyl-2-oxo-1,2-dihydroquinoline-3-carboxamido)acetate (400 mg, 1084 μmol), 3,5-dimethylisoxazol-4-ylboronic acid (305 mg, 2167 μmol) and Pd(PPh3)4 (125 mg, 108 μmol) in 8 ml 1,2-dimethoxyethane (or DMF) and 1.6 ml 2M aqueous Na2CO3 was heated to 75° C. and stirred for 12 hours. The mixture was cooled to 24° C., treated with 1M aqueous HCl and CHCl3, after which solids precipitated. The organic layer was separated and the solids were collected by filtration, and washed with MeOH.

Method 22:
2-(4-Hydroxy-1-methyl-2-oxo-6-(piperidin-1-yl)-1,2-dihydroquinoline-3-carboxamido)acetic acid

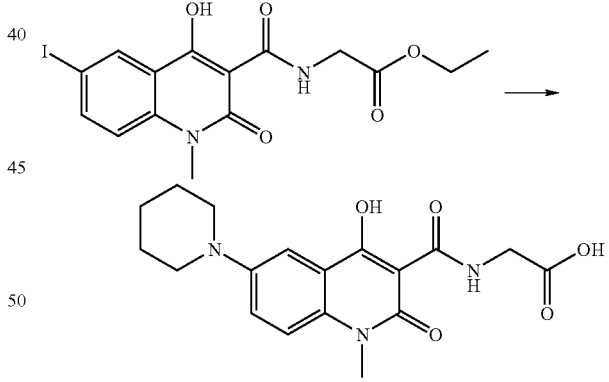

A solution of ethyl 2-(4-hydroxy-6-iodo-1-methyl-2-oxo-1,2-dihydroquinoline-3-carboxamido)acetate (250 mg, 581 μmol), Pd2dba3.CHCl3 (60 mg, 58 μmol), X-Phos (55 mg, 116 μmol) and sodium t-butoxide (279 mg, 2906 μmol) in 1,4-dioxane (5 ml) was treated with piperidine (287 μl, 2906 μmol). The reaction was stirred at 80° C. in a sealed tube. After 22 hours, the solution was cooled to 23° C., filtered through celite (washing with MeOH), concentrated, diluted with methanol/DMSO and purified by RP HPLC (0-100% MeCN/water+1% TFA, 10 min), affording 17 mg (8%) of 2-(4-hydroxy-1-methyl-2-oxo-6-(piperidin-1-yl)-1,2-dihydroquinoline-3-carboxamido)acetic acid as an off-white solid.

Method 23:
2-(4-Hydroxy-1-methyl-6-morpholino-2-oxo-1,2-dihydroquinoline-3-carboxamido)acetic acid

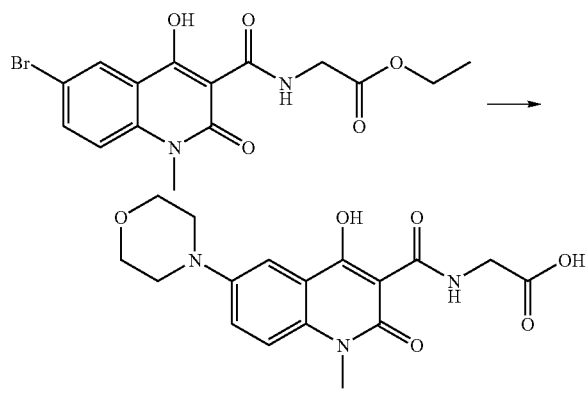

A solution of ethyl 2-(6-bromo-4-hydroxy-1-methyl-2-oxo-1,2-dihydroquinoline-3-carboxamido)acetate (202 mg, 527 μmol), Pd$_2$ dba$_3$.CHCl3 (55 mg, 53 μmol), X-Phos (50 mg, 105 μmol) and morpholine (115 μl, 1318 μmol) in 1,4-dioxane (3 ml) was treated with sodium tert-butoxide (203 mg, 2109 μmol). The reaction was stirred at 80° C. in a sealed tube. After 21 hours, the solution was adsorbed onto silica gel, concentrated in vacuo and purified by silica gel chromatography (eluant: 4% methanol/dichloromethane, followed by/dichloromethane+1% AcOH) and subsequently by RP HPLC (0-100% MeCN/water+1% TFA, 10 min) affording 21 mg (11%) of 2-(4-hydroxy-1-methyl-6-morpholino-2-oxo-1,2-dihydroquinoline-3-carboxamido)acetic acid as an yellow solid.

Method 24:
2-(4-Hydroxy-1-methyl-7-morpholino-2-oxo-1,2-dihydroquinoline-3-carboxamido)acetic acid

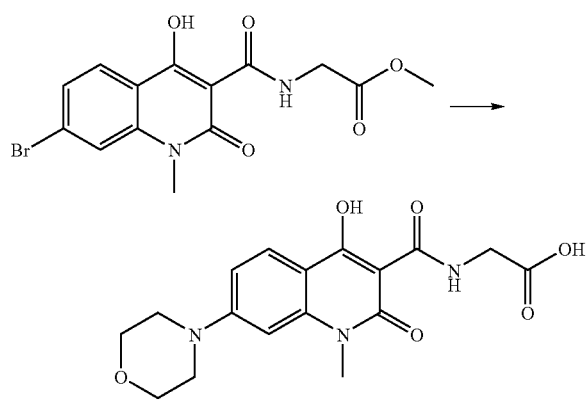

A solution of methyl 2-(7-bromo-4-hydroxy-1-methyl-2-oxo-1,2-dihydroquinoline-3-carboxamido)acetate (100 mg, 271 μmol), Pd$_2$ dba$_3$.CHCl3 (28 mg, 27 μmol), X-Phos (26 mg, 54 μmol) and morpholine (71 μl, 813 μmol) in 1,4-dioxane (3 ml) was treated with sodium tert-butoxide (104 mg, 1084 μmol). The reaction was stirred at 80° C. in a sealed tube. After 24 hours, the suspension was cooled to 23° C., filtered through celite (extensively washing with methanol), the filtrate concentrated in vacuo and purified by silica gel chromatography after adsorption onto silica (eluant: 10% methanol/dichloromethane+1% AcOH), affording 18 mg (18%) of 2-(4-Hydroxy-1-methyl-7-morpholino-2-oxo-1,2-dihydroquinoline-3-carboxamido)acetic acid as a greenish-white solid.

Method 25:
2-(4-Hydroxy-1-methyl-2-oxo-7-(piperidin-1-yl)-1,2-dihydroquinoline-3-carboxamido)acetic acid

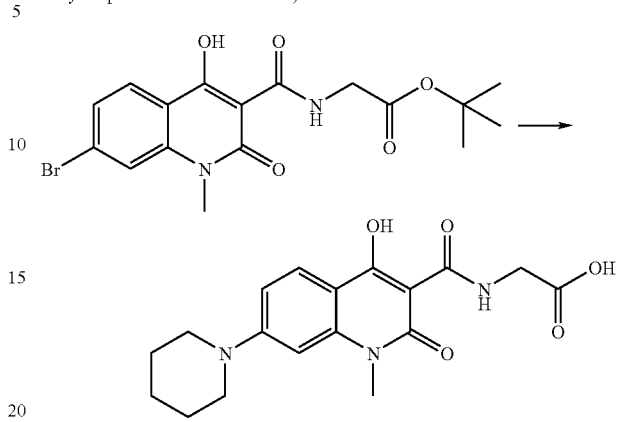

A solution of tert-butyl 2-(7-bromo-4-hydroxy-1-methyl-2-oxo-1,2-dihydroquinoline-3-carboxamido)acetate (205 mg, 498 μmol), Pd$_2$ dba$_3$.CHCl3 (52 mg, 50 μmol), X-Phos (48 mg, 100 μmol) and piperidine (123 μl, 1246 μmol) in 1,4-dioxane (5 ml) was treated with sodium tert-butoxide (192 mg, 1994 μmol). The reaction was stirred at 80° C. in a sealed tube. After 15 hours, the solution was cooled to 23° C., adsorbed onto silica gel, concentrated in vacuo and purified by silica gel chromatography (eluant: 5% methanol/dichloromethane, followed by 5% methanol/dichloromethane+1% AcOH), affording an yellow solid which was 83% pure. The impure solid was purified by RP HPLC (0-100% MeCN/water+1% TFA, 10 min), affording 83 mg (46%) of the product as an yellow solid.

Method 26:
Methyl-2-(4-hydroxy-1-methyl-2-oxo-7-(2-(trimethilsilyl)ethynyl)-1,2-dihydroquinoline-3-carboxamido)acetate

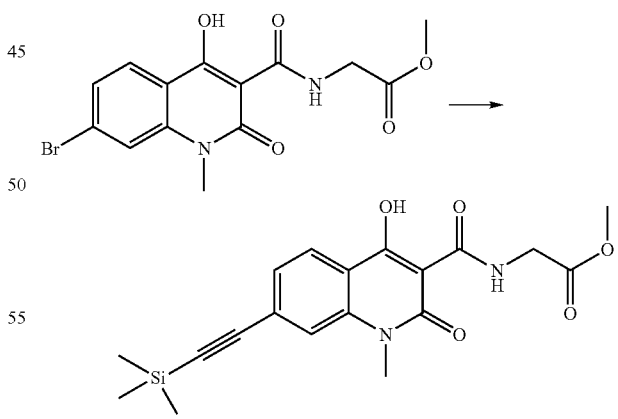

In a sealed tube was combined methyl 2-(7-bromo-4-hydroxy-1-methyl-2-oxo-1,2-dihydroquinoline-3-carboxamido)acetate (0.75 g, 2.0 mmol), Dichlorobis(triphenylphosphine) palladium(II) (0.14 g, 0.20 mmol), copper(I) iodide (0.077 g, 0.41 mmol), ethynyltrimethylsilane (1.4 ml, 10 mmol), and N-ethyl-N-isopropylpropan-2-amine (2.8 ml, 16 mmol) in tetrahydrofuran (20.0 ml, 2.0 mmol). The tube was flushed with Ar, sealed, and placed in an oil bath at 100° C. for 5 hours. The dark mixture was cooled to rt, filtered and washed with ethyl acetate (2×30 mL). The crude mixture was concentrated, adsorbed onto silica and purified by flash chromatography (15% to 40% EtOAc:Hex gradient) to afford the product as a solid (0.59 g, 75% yield).

Method 27:
2-(7-Cyano-4-hydroxy-1-methyl-2-oxo-1,2-dihydroquinoline-3-carboxamido)acetic acid

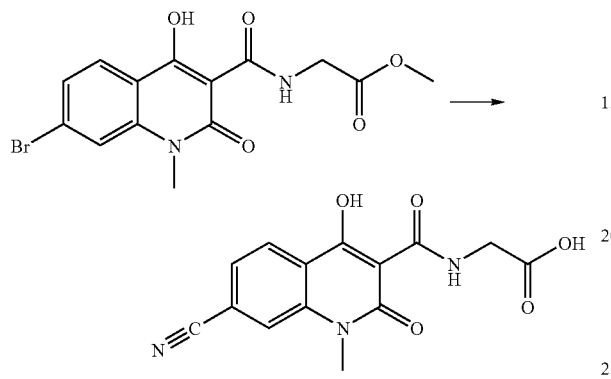

In a sealed flask was combined methyl 2-(7-bromo-4-hydroxy-1-methyl-2-oxo-1,2-dihydroquinoline-3-carboxamido)acetate (2.0 g, 5.4 mmol), 1,1'-bis(diphenylphosphino)ferrocene (0.48 g, 0.87 mmol), copper cyamide (1.9 g, 22 mmol), $Pd_2(dba)_3$ (0.20 g, 0.22 mmol) and 1,4-dioxane (50.0 mL, 5.4 mmol). The flask was flushed with argon, and then tetraethylammonium cyamide (0.85 g, 5.4 mmol) was added. After sealing the tube and heating at 75° C. for 4 hours, the reaction was cooled to rt and then adsorbed onto silica. The crude reaction mixture was purified using flash chromatography (15-70% EtOAc:Hex gradient) to afford the ester intermediate. The methyl ester was hydrolyzed by mixing the solid with 5 N aqueous NaOH (5 mL) in THF (4 mL) for 4 hours. The mixture was acidified to pH 1 with 5 N HCl and the solid was collected by filtration, washed with water (5×15 mL) and then with ether (2×5 mL). The solid was dried in a vacuum oven overnight at 50° C. to afford the desired material (0.92 g, 56% yield).

Method 28:
2-(7-Ethyl-4-hydroxy-1-methyl-2-oxo-1,2-dihydroquinoline-3-carboxamido)acetic acid

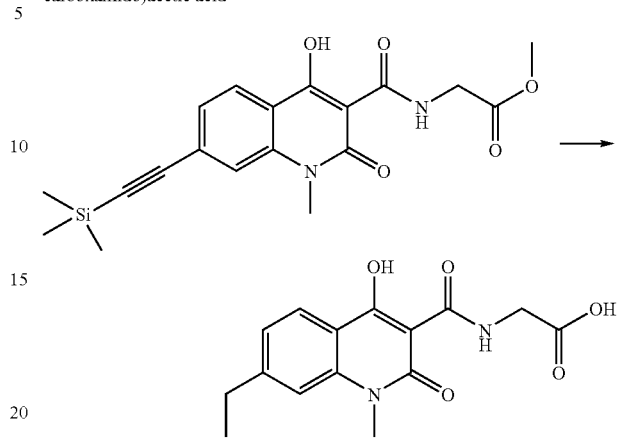

To a stirred solution of methyl 2-(4-hydroxy-1-methyl-2-oxo-7-(2-(trimethylsilyl)ethynyl)-1,2-dihydroquinoline-3-carboxamido)acetate (0.59 g, 1.5 mmol) in N,N-dimethylformamide (5.0 mL, 1.5 mmol) and methanol (1.0 mL, 1.5 mmol) was added cesium fluoride (0.23 g, 1.5 mmol) under nitrogen. After stirring at room temperature for 1 hour, the mixture was concentrated to remove solvents. The resulting solid was adsorbed onto silica and purified using flash chromatography (15-80% EtOAc:Hex gradient) to afford a yellow solid. The solid was suspended in methanol (10 mL) with Pd/C (20 mol %) and exposed to hydrogen from a balloon for 16 h. The crude reaction mixture was filtered through Celite, and the filter pad washed with dichloromethane (5×10 mL) under argon. The filtrate was concentrated to give a white solid that was further purified on silica by flash chromatography (100% chloroform). The solid was then treated with 5 N aqueous NaOH (3 mL) in THF (3 mL) for 5 hours. The mixture was acidified to pH 1 using 5 N aqueous HCl, and the resulting precipitate was collected by filtration. After washing the solid with water (5×10 mL0 and ether (2×10 ml), the desired material was obtained after drying in a vacuum oven overnight at 50° C. (0.21 g, 38% yield, 3 steps).

Method 29:
Ethyl 2-(6-cyano-4-hydroxy-1-methyl-2-oxo-1,2-dihydroquinoline-3-carboxamido)acetate

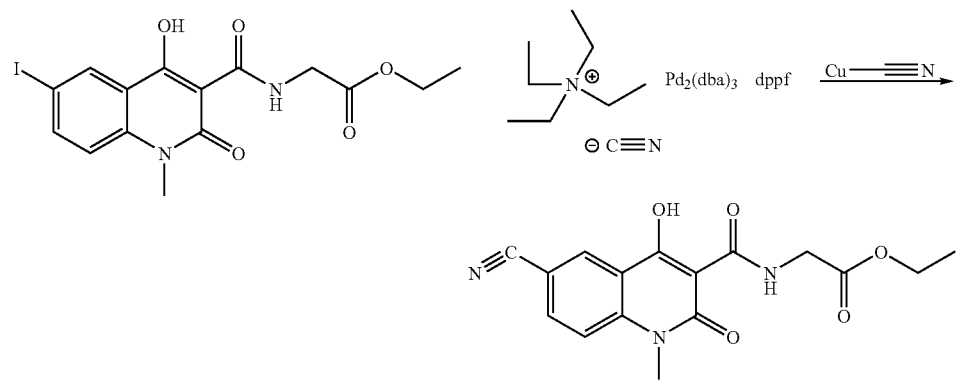

Ethyl 2-(4-hydroxy-6-iodo-1-methyl-2-oxo-1,2-dihydroquinoline-3-carboxamido)acetate (0.200 g, 0.46 mmol), 1,1'-bis(diphenylphosphino)ferrocene (0.048 g, 0.087 mmol), Copper cyamide (0.194 g, 2.2 mmol) and Tris(dibenzylideneacetone)dipalladium (0.020 g, 0.022 mmol) in 1,4-dioxane (2 ml) were combined in a 10 ml tube. Tetraethylammonium cyamide (0.085 g, 0.54 mmol) and 1,4-dioxane (1 ml) were added and the tube was sealed and heated to 145° C. for 15 min under Argon in a microwave (Personal Chemistry 300 W). After cooling, the mixture was filtered and washed with methylene chloride (50 ml). The filtrate was washed with deionized water (3×50 ml), then with brine (50 ml), dried over magnesium sulfate then concentrated and dried in vacuo. Flash column chromatography (Silica gel, 0-100% methylene chloride in hexane) gave a solid which washed with diethyl ether, filtered and dried in vacuo to give ethyl 2-(6-cyano-4-hydroxy-1-methyl-2-oxo-1,2-dihydroquinoline-3-carboxamido)acetate (0.135 g, 90% yield).

Method 31:
2-(4-Hydroxy-1-methyl-2-oxo-6-phenyl-1,2-dihydroquinoline-3-carboxamido)acetic acid (can also be used for methyl ester)

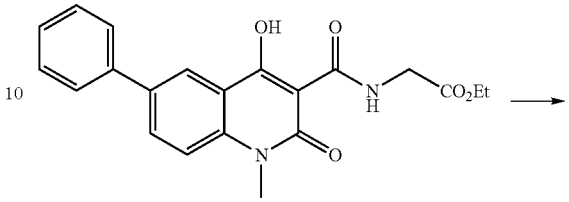

Method 30:
Ethyl 2-(6-(2,4-dimethylthiazol-5-yl)-4-hydroxy-1-methyl-2-oxo-1,2-dihydroquinoline-3-carboxamido)acetate

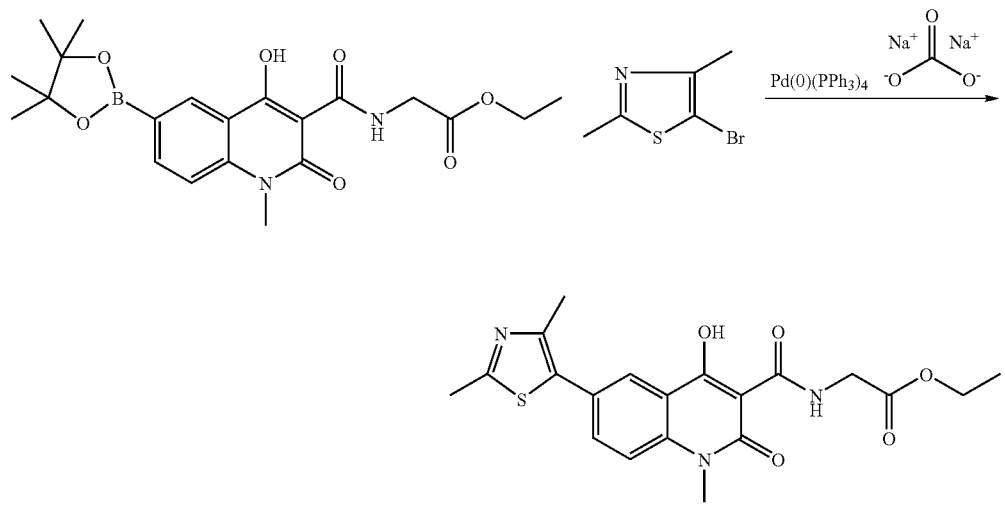

To a solution of ethyl 2-(4-hydroxy-1-methyl-2-oxo-6-(4,4,5,5-tetramethyl-1,3,2-dioxaborolan-2-yl)-1,2-dihydroquinoline-3-carboxamido)acetate (0.200 g, 0.465 mmol) in 1,4-dioxane/dimethylformamide (4:1, 5 ml) was added 5-bromo-2,4-dimethyl-1,3-thiazole (0.134 g, 0.697 mmol), tetrakis(triphenylphosphine)palladium(0) (0.0537 g, 0.0465 mmol) and sodium carbonate (0.349 ml, 0.697 mmol). The mixture was heated to 145° C. in a sealed tube under argon for 15 min in a microwave (Personal Chemistry 300 W). By LC/MS the ratio of ethyl ester to acid to starting material was 9:3:1. After cooling the mixture was diluted with deionized water (50 ml) and extracted with ethyl acetate (2×25 ml). The organic colution washed with deionized water (2×50 ml), then with brine (30 ml), dried over Magnesium sulfate, concentrated and dried in vacuo to give 241 mg crude product. Flash column chromatography (silica gel, 0-25% ethyl acetate in methylene chloride) yielded 86 mg of yellow solid which washed with ether, filtered and dried in vacuo to give ethyl 2-(6-(2,4-dimethylthiazol-5-yl)-4-hydroxy-1-methyl-2-oxo-1,2-dihydroquinoline-3-carboxamido)acetate (0.0330 g, 17.1% yield) as a white solid.

-continued

To a solution of ethyl 2-(4-hydroxy-1-methyl-2-oxo-6-phenyl-1,2-dihydroquinoline-3-carboxamido)acetate (120 mg, 315 μmol) and Tetrahydrofuran (15 ml) was added 5N Sodium hydroxide (1.3 ml), and the mixture was stirred at room temperature. After 2.5 hours, reaction was complete. The reaction mixture was acidified with 5N HCL (2 ml) and concentrated on a roto-evaporator until solid appeared, then water was added and filtered to give the desired compound as a light peach colored solid. Yield=77 mg.

Method 32:
2-(7-(3,5-dimethylisoxazol-4-yl)-4-hydroxy-1-methyl-2-oxo-1,2-dihydroquinoline-3-carboxamido)acetic acid

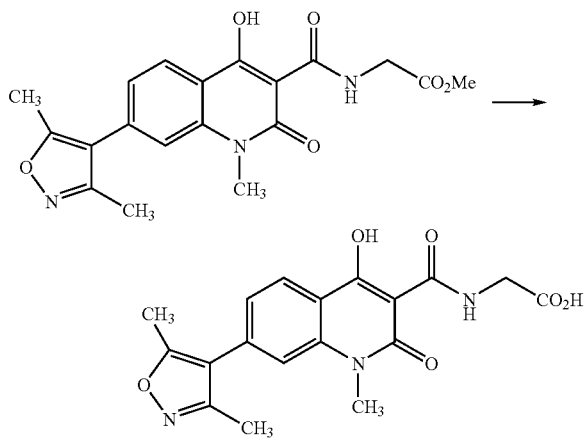

Suspended Methyl 2-(7-(3,5-dimethylisoxazol-4-yl)-4-hydroxy-1-methyl-2-oxo-1,2-dihydroquinoline-3-carboxamido)acetate in 3 ml MeOH, 1 ml THF, and 2 ml 1M aqueous NaOH and stirred at 24° C. for 4 hours. The mixture was acidified to pH=1 using 2M aqueous HCl and the solids collected by filtration, washed with H₂O and dried in vacuo: 50 mg white solids.

Method 33:
2-(7-(4-dimethylamino)phenyl)-4-hydroxy-1-methyl-2-oxo-1,2-dihydroquinoline-3-carboxamido)acetic acid

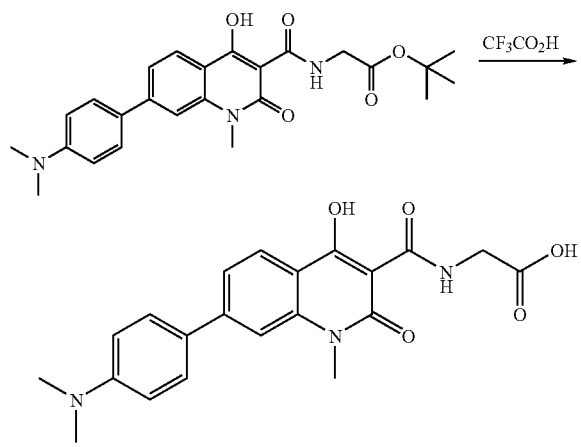

Trifluoroacetic acid (4.00 ml, 54 mmol) was added to a suspension of tert-butyl 2-(7-(4-(dimethylamino)phenyl)-4-hydroxy-1-methyl-2-oxo-1,2-dihydroquinoline-3-carboxamido)acetate (0.057 g, 0.13 mmol) in dichloromethane (2.00 ml). After stirring at room temperature for 10 min water was added and the solution loaded in SCX MEGA BE column. The column was flushed with methanol extensible followed by 2M ammonia in methanol. The fractions obtained from the ammonia in methanol were collected and the solvent removed in vacuo. The residue was treated with 5N NaOH (2 ml) in THF (1 ml) and stirred at room temperature for 1 hour. The suspension was acidified with 5N HCl and the solids collected by filtration. The solids were washed with water, ether, dried in a vacuum oven at 50° C. to afford green solids (10 mg).

Method 34:
2-(7-(3-cyanophenyl)-4-hydroxy-1-methyl-2-oxo-1,2-dihydroquinoline-3-carboxamido)acetic acid

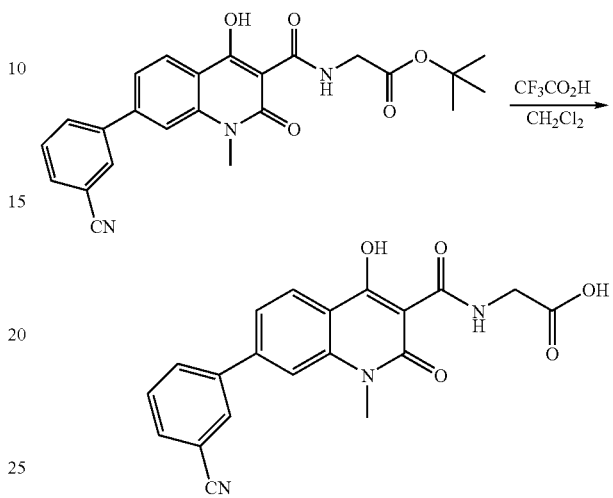

Trifluoroacetic acid (4.00 ml, 54 mmol) was added to a suspension of tert-butyl 2-(7-(3-cyanophenyl)-4-hydroxy-1-methyl-2-oxo-1,2-dihydroquinoline-3-carboxamido)acetate (0.162 g, 0.37 mmol) in dichloromethane (2.00 ml). After stirring for one hour at room temperature water was added and the solids formed were collected by filtration. The solids were washed with water, ether, dried in a vacuum oven at 50° C. to afford off-white solids in 74% yield.

Method 35:
3-((carboxymethyl)carbomoyl)-4-hydroxy-1-methyl-2-oxo-1,2-dihydroquinoline-7-carboxylic acid

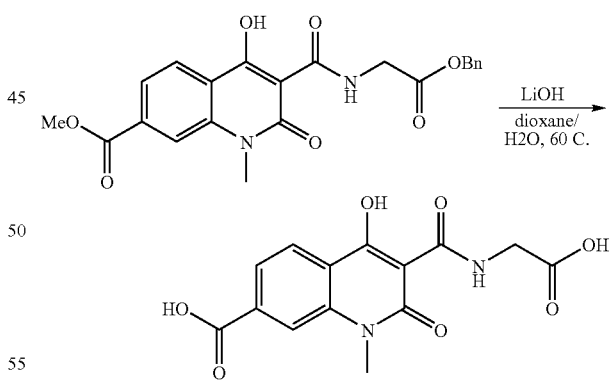

Methyl 3-((2-(benzyloxy)-2-oxoethyl)carbamoyl)-4-hydroxy-1-methyl-2-oxo-1,2-dihydroquinoline-7-carboxylate (26 mg, 61 µmol) (65689-17-3) was dissolved in 12 ml dioxane/H₂O (5:1) and to this was added lithium hydroxide monohydrate (613 µl, 613 µmol) as a 1M aqueous solution. The resultant mixture was heated to 60 C for 4 hrs. The solvent was removed in vacuo and the aqueous layer was acidified with 2N HCl to pH2. Following dilution with EtOAc, the layers were separated and the aqueous layer was extracted with EtOAc (3×). The organic layer washed with H₂O and Method 36:
2-(1-methyl-2-oxo-1,2-dihydroquinoline-3-carboxamido)acetic acid

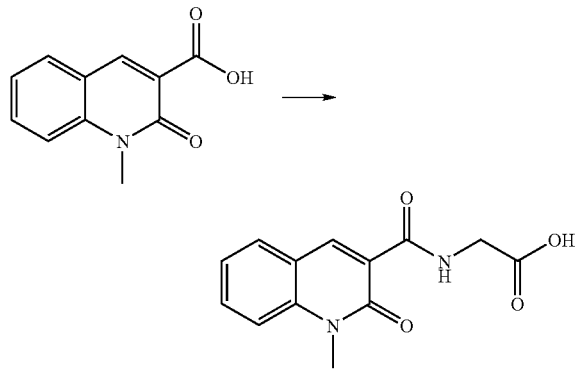

1-methyl-2-oxo-1,2-dihydroquinoline-3-carbonyl chloride, prepared from 1-methyl-2-oxo-1,2-dihydroquinoline-3-carboxylic acid (Archiv der Pharmazie (1990), 323(2), 67-72) and oxalyl chloride, was added dropwise to a solution of tert-butyl 2-aminoacetate hydrochloride (0.041 g, 0.25 mmol), diisopropylethyl amine (0.086 ml, 0.49 mmol), in dichloromethane (1.00 ml), stirred at room temperature for 1 hr. The reaction mixture was diluted with dichloromethane, washed with water and dried over MgSO4 to afford tert-butyl 2-(1-methyl-2-oxo-1,2-dihydroquinoline-3-carboxamido) acetate in a 27% yield.

Trifluoroacetic acid (1.00 ml, 13 mmol) was added to tert-butyl 2-(1-methyl-2-oxo-1,2-dihydroquinoline-3-carboxamido)acetate (0.021 g, 0.07 mmol) and stirred at room temperature for 15 minutes. Trifluoroacetic acid was removed under vacuum and the resulting solids were washed with water (3×), ether (3×) and dried in a vacuum oven at 50° C. to afford 2-(1-methyl-2-oxo-1,2-dihydroquinoline-3-carboxamido)acetic acid in 29% yield.

Method 37:
2-(4-Methoxy-1-methyl-2-oxo-1,2-dihydroquinoline-3-carboxamido)acetic acid

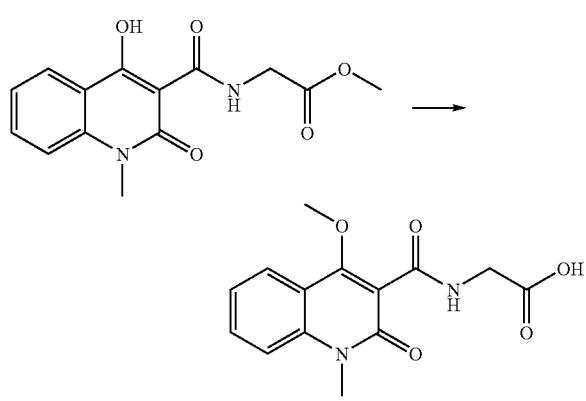

Methyl 2-(4-hydroxy-1-methyl-2-oxo-1,2-dihydroquinoline-3-carboxamido)acetate (0.394 g, 1.4 mmol), methanol (0.33 ml, 8.1 mmol) and triphenyl phosphine (0.94 ml, 4.1 mmol) were placed in a 50 mL round bottomed flask with 25 mL of THF. The flask was placed in an ice bath. Diethyl azodicarboxylate (0.64 ml, 4.1 mmol) was added dropwise. A white solid was filtered and this solid was purified by silica flash chromatography (0-3% MeOH/DCM) to give the desired product.

Methyl 2-(4-methoxy-1-methyl-2-oxo-1,2-dihydroquinoline-3-carboxamido)acetate (0.150 g, 0.5 mmol) was dissolved in THF in a 25 mL round bottom flask. NaOH was added and the mixture was stirred for 1.5 hours. Dichloromethane and water were added to the reaction and the layers were separated. The aqueous layer washed two more times with dichloromethane. To the aqueous phase, 1N HCL was added until the pH was approximately 1. The aqueous phase was then extracted with 25% IPA/CHCl3, dried with MgSO4 and concentrated on a roto-evaporator. The compound was then purified by HPLC to give the desired product as a white solid.

The following are examples of methods that may be used to quantitate HIF PHD activity and the inhibition of HIF PHD activity by compounds of the present invention.

Expression, Purification and Europium Labeling of VCB and Design of an Eu-VCB Based HTRF Assay for the Detection of Hydroxyprolyl HIF1α Peptides The VCB complex is defined as the Von Hippel-Lindau protein (pVHL), elongin B and elongin C heterotrimeric complex. VCB specifically binds to hydroxyproline residues of HIF1α, initiating polyubiquitinylation of HIF1α and its subsequent proteolytic destruction. In the absence of prolyl hydroxylase activity, VCB does not bind unmodified HIF1α. The VCB complex was expressed in E. coli and purified from the soluble fraction. The amino acid sequences of the three protein components are as follows:

```
VHL (Amino Acids 54-213)
                                     (SEQ ID NO: 1)
MHHHHHHEAGRPRPVLRSVNSREPSQVIFCNRSPRVVLPVWLNFDGEPQP
YPTLPPGTGRRIHSYRGHLWLFRDAGTHDGLLVNQTELFVPSLNVDGQPI
FANITLPVYTLKERCLQVVRSLVKPENYRRLDIVRSLYEDLEDHPNVQKD
LERLTQERIAHQRMGD ElonginB
                                     (SEQ ID NO: 2)
MDVFLMIRRHKTTIFTDAKESSTVFELKRIVEGILKRPPDEQRLYKDDQL
LDDGKTLGECGFTSQTARPQAPATVGLAFRADDTFEALCIEPFSSPPELP
DVMKPQDSGSSANEQAVQ*

ElonginC (Amino Acids 17-112)
                                     (SEQ ID NO: 3)
MYVKLISSDGHEFIVKREHALTSGTIKAMLSGPGQFAENETNEVNFREIP
SHVLSKVCMYFTYKVRYTNSSTEIPEFPIAPEIALELLMAANFLDC
```

The N-terminus of VHL contains a six histidine affinity tag for purification purposes.

A VCB-based assay allows a highly sensitive and direct measurement of enzymatic product formation (HIF1α protein or fragments thereof containing a hydroxylated proline residue) and is suitable for high throughput screening.

For expression in E. coli, VHL 54-213 was cloned into pAMG21 (Plux promoter) between the NdeI-XhoI site. Immediately downstream of this is the ElonginC gene cloned into the XhoI site to SacII. There is a 13 bp spacer between the stop codon of VHL and the initiating codon of ElonginC. The expression plasmid pAMG21 is a 6118 base pair plasmid that was derived from the expression vector pCFM1656 (ATCC #69576), which in turn can be derived from the expression vector system described in U.S. Pat. No. 4,710,473. This design allows for chemical rather than thermal induction of protein expression by substitution of the promoter region, replacing a synthetic bacteriophage lambda pl promoter with a DNA segment containing the LuxR gene and the LuxPR promoter, and affords regulation of expression by the plasmid-encoded LuxR protein, thereby allowing any *E. coli* strain to serve as host.

ElonginB was cloned into pTA2 (pACYC184.1 based vector) under the control of a Lac promoter. Competent *E. coli* cells were transformed with the pAMG21-VHL-ElonginC construct. These *E. coli* cells were rendered competent again prior to transformation with the pTA2-elonginB construct to produce the final *E. coli* strain containing both plasmid constructs. Induction of protein expression was initiated by the addition of IPTG and N-(3-oxo-hexanoyl)-homoserine lactone (HSL) at 30° C.

Bacterial cells were lysed by a microfluidizer in aqueous buffer of pH 8.0 and the soluble fraction was separated by centrifugation. The soluble *E. coli* fraction was subjected to Nickel-NTA chelating chromatography to utilize the six histidine affinity tag located on the pVHL construct. The pooled fractions from the nickel column were applied to a Superdex 200 size exclusion chromatography (SEC) column. The protein eluted as a monomer on SEC, indicating that the three protein components formed a complex in solution. The fractions from the SEC column were pooled and applied to a Q Sepharose anion exchange column for final purification. The purified complex was visualized by SDS-PAGE and the identities of the three protein components were confirmed by N-terminal amino acid sequencing.

Purified VCB was exchanged into 50 mM sodium carbonate buffer pH 9.2 and labeled with a europium chelate overnight. LANCE™ europium chelate (PerkinElmer, Inc; Eu-W1024 ITC chelate; catalog number is AD0013) was used to label the lysine residues of the VCB complex. The chelate contains an isothiocyanate reactive group that specifically labels proteins on lysine residues (there are fifteen lysine residues in the VCB protein complex). The resulting europylated VCB was purified by desalting columns and quantitated by standard means. The labeling yield was determined to be 6.6 europium groups per one VCB complex.

Two peptides were produced by SynPep, Inc: a hydroxyproline modified peptide and an unmodified control peptide. VCB was expected to specifically bind to the hydroxyproline modified peptide (a mimic of enzymatic hydroxylation by prolyl hydroxylase). VCB was not expected to bind to the unmodified peptide. Both peptides were produced with a biotin group at the N-terminus to allow for binding by the streptavidin-labeled fluorescent acceptor allophycocyanin (streptavidin APC; Prozyme, Inc.).

The sequence of the custom synthesized HIF1α peptides (amino acids 556-575, with methionine residues replaced with alanine residues to prevent oxidation) were as follows:

```
                                             (SEQ ID NO: 4)
(unmodified)   Biotin-DLDLEALAPYIPADDDFQLR-CONH2

(SEQ ID NO: 5)
(modified)     Biotin-DLDLEALA[hyP]YIPADDDFQLR-CONH2
```

The peptides were purchased from SynPep as lyophilized solids and were suspended in DMSO for experimental use. The peptides were quantitated according to their absorbance at 280 nm.

Experiments were conducted in 96 well Costar polystyrene plates. Biotinylated peptides and europylated VCB were suspended in the following buffer: 100 mM HEPES 7.5, 0.1 M NaCl, 0.1% BSA and 0.05% Tween 20. The reagents were allowed to reach equilibrium by shaking for 1 hour before the plates were read on the Discovery Instrument (Packard). The data output is the ratio of the 665 nm and 620 nm emission signal resulting from the 320 nm excitation.

As shown in FIG. 1, the specific interaction of europylated VCB with the hydroxyproline modified HIF1α peptide coupled to streptavidin APC generated a fluorescence signal detectable over the background signal. These results demonstrate a fluorescence signal generated by the specific interaction of Eu-VCB with hyp-HIF1α peptide. Each bar represents the data from a single well of a 96 well assay plate. The signal to background ratio was calculated from data from a control plate (unmodified peptide). Eu-VCB concentration was titrated across rows (nM) and streptavidin APC concentrations were titrated down columns. The peptide concentration was fixed at 100 nM.

Detection of Enzymatically Converted
Hydroxyprolyl HIF-1α by HIF PHD2 and Inhibition
of HIF PHD2 Activity Binding of the P564-HIF1α peptide to VCB was validated utilizing the homogeneous time-resolved FRET (HTRF) technology. A 17 amino acid (17 aa) peptide with an N-terminally labeled biotin molecule corresponding to amino acid sequences 558 to 574 of the HIF1α protein was synthesized in-house (DLEMLAPYIPMDDDFQL) (SEQ ID NO: 6). A second 17 aa peptide containing a hydroxylated proline at position 564 was chemically generated to mimic the PHD enzyme converted product form of the protein that is recognized by VCB. The assay was performed in a final volume of 100 µl in buffer containing 50 mM Tris-HCl (pH 8), 100 mM NaCl, 0.05% heat inactivated FBS, 0.05% Tween-20, and 0.5% NaN$_3$. The optimal signal over background and the linear range of detection was determined by titrating the hydroxylated or unhydroxylated peptide at varied concentrations between 0 and 1 µM with a titration of VCB-Eu at varying concentrations between 0 and 50 nM with 50 nM of streptavidin APC. The binding reagents were allowed to reach equilibrium by shaking for 1 hour before it was read on the Discovery Instrument (Packard). The data output is the ratio of the 665 nm and 620 nm emission signal resulting from the 320 nm excitation.

HIF PHD2 activity was detected by P564-HIF1α peptide and VCB binding in the HTRF format. HIF PHD2 was assayed at various concentrations between 0 and 400 nM with 3 µM HIF1α peptide in buffer containing 50 mM Tris-HCl (pH 7.5), 100 mM NaCl, 0.05% Tween 20, 2 mM 2-oxoglutarate (2-OG), 2 mM ascorbic acid and 100 µM FeCl$_2$ in a final volume of 100 µL. The time-course was determined by periodically transferring 2.5 µL of the reaction into 250 µl of 10×HTRF buffer containing 500 mM HEPES (pH 7.5), 1M NaCl, 1% BSA, and 0.5% Tween-20 to terminate the enzyme reaction. 15 nM HIF-1α peptide from the terminated reaction was added to 35 nM streptavidin-APC and 10 nM VCB-Eu to a final volume of 100 µl in 10×HTRF buffer. The HTRF reagents were placed on a shaker for 1 hour before detection on the Discovery platform.

As demonstrated in FIG. 2, there was a dose dependent increase in HTRF signal resulting from binding of the hydroxylated-P564-HIF1α peptide to VCB-Eu compared to the unhydroxylated form of the peptide resulting in a 14 fold signal over noise ratio at 125 nM HIF1α peptide. VCB binding to the APC bound peptide permits a FRET transfer between the Eu and APC. The signal was linear to 2 nM peptide with 3.125 nM VCB, but increases to 62.5 nM peptide with 50 nM VCB resulting in a larger linear range.

HTRF detection utilizing Eu-labeled VCB is a practical system for determining HIF PHD2 catalytic activity. HIF PHD2 hydroxylation of the HIF1α peptide results in the increase affinity of VCB to the peptide and hence and increased FRET signal. As shown in FIG. 3, activity was verified with a fairly linear and an increasing HTRF signal over time. There was a dose dependant increase in initial rates with increasing HIF PHD2 enzyme concentration up to 400 nM. The initial rates were linear to 100 nM enzyme.

Inhibition of HIF PHD2 activity was quantified utilizing the HTRF technology. HIF PHD2 catalyzes a hydroxyl modification on the proline residue of the P564-HIF1α peptide substrate (Biotin-DLEMLAPYIPMDDDFQL) (SEQ ID NO: 6) resulting in recognition and binding of the europylated Von Hippel-Lindau protein (pVHL), elongin B and elongin C heterotrimeric (VCB-Eu) complex.

The PHD2 inhibition assay was executed by addition of freshly dissolved $FeCl_2$ to 178.57 μM (100 μM final concentration) in PHD2 Reaction Buffer containing 30 mM MES, pH 6, 10 mM NaCl, 0.25% Brij-35, 0.01% BSA, and 1% DMSO. 28 μL of the iron solution and 2 μl of inhibitor compounds serially diluted in 100% DMSO (5% DMSO final) were added to black polypropylene 96-well microtiter plates. To that, 10 μL of 10 nM PHD2 (2 nM final) was added to all wells of the plate except for the 8 wells of column 12 (LO control), and allowed to incubate at room temperature on the shaker for one hour. Column 6 was the HI control containing PHD2 enzyme and 5% DMSO vehicle, but no inhibitor compound. To initiate the PHD2 enzymatic reaction, 10 μL of a solution containing 500 nM P564-HIF1α peptide (100 nM final), 10 mM ascorbic acid (2 mM final), and 1.25 μM 2-oxoglutarate (α-ketoglutarate; 0.25 μM final) in PHD2 Reaction Buffer was added to all wells of the plate and allowed to incubate on the shaker at room temperature for one hour.

The reaction was terminated by addition of 25 μL HTRF Buffer (50 mM TRIS-HCl, pH 9, 100 mM NaCl, 0.05% BSA, and 0.5% Tween-20) containing 150 mM succinate (product inhibitor; 50 mM final), 75 nM streptavidin-APC (25 nM final), and 7.5 nM VCB-Eu (2.5 nM final). The HTRF detection reagents were placed on a shaker for 1 hour to reach binding equilibrium before reading on the Discovery platform (PerkinElmer). Europium is excited at 315 nm and phosphoresces at 615 nm with a large Stoke's shift. APC, in turn, emits at 655 nm upon excitation at 615 nm. The HTRF signal is measured as the ratio of the APC 655 nm signal divided by the internal europium reference 615 nm emission signal.

The POC (percentage of control) was determined by comparing the signal from hydroxylated peptide substrate in the enzyme reaction containing inhibitor compound with that from PHD2 enzyme with DMSO vehicle alone (HI control), and no enzyme (LO control). POC was calculated using the formula: % control (POC)=(cpd−average LO)/(average HI−average LO)*100. Data (consisting of POC and inhibitor concentration in μM) was fitted to a 4-parameter equation $(y=A+((B-A)/(1+((x/C)^D)))$, where A is the minimum y (POC) value, B is the maximum y (POC), C is the x (cpd concentration) at the point of inflection and D is the slope factor) using a Levenburg-Marquardt non-linear regression algorithm.

In certain embodiments, compounds of the present invention exhibit a HIF PHD inhibitory activity $IC_{50}$ value of 40 μM or less. In additional embodiments, compounds of the present invention exhibit a HIF PHD inhibitory activity $IC_{50}$ value of 10 μM or less.

Ruthenylation and Application of His-Tagged VCB in Electrochemiluminescence (ECL) Detection Assay Ruthenylated VCB (Ru-VCB) was produced that retained HIF binding activity and was used to develop a bead-based electrochemiluminescence assay for the detection of hydroxylated HIF peptides.

The following HIF1α peptides were synthesized (amino acids 558-574):

```
                                    (SEQ ID NO: 6)
    Biotin-HIF:     DLEMLAPYIPMDDDFQL (SEQ ID NO: 7)
    Biotin-HIF-OH:  DLEMLA[hyP]YIPMDDDFQL
```

VCB, produced as described above, was ruthenylated (covalently through lysine residues) by mixing 500 μL of VCB (1 mg/mL in 50 mM carbonate buffer, pH 9.0) with 50 μL of ORI-TAG™-NHS ester (Bio Veris Corporation, Gaithersburg, Md.; 3 mg/mL in 100% DMSO) for a 12:1 Ru:VCB molar challenge ratio. The sample was wrapped in foil to protect it from light and the chemical conjugation was allowed to occur for one hour at room temperature. The reaction was stopped by adding 20 μL 2M glycine and incubating for 10 minutes. Ru-VCB was purified from unconjugated Ru-tag by dialysis into storage buffer (20 mM Tris pH 7.5, 150 mM NaCl).

To evaluate the use of Ru-VCB as an ECL detection reagent for biotin-HIF-OH (as well as to explore sensitivity and linear range), both biotin-HIF and biotin-HIF-OH were serially diluted and mixed with varying concentrations of Ru-VCB and 0.33 ug/uL streptavidin M280 Dynabeads (Invitrogen) in assay buffer (50 mM Tris-Hcl, pH 8.0, 100 mM NaCl, 0.05% Tween 20, 0.5% $NaN_3$). After a two-hour incubation at room temperature with shaking, the reaction was read on the M-SERIES™ analyzer (Bio Veris Corporation, Gaithersburg, Md.). A low voltage was applied to the Ru-VCB/biotin-HIF-OH binding complexes, which in the presence of Tripropylamine (TPA, the active component in the ECL reaction buffer, BV-GLOW™, Bio Veris Corporation, Gaithersburg, Md.), resulted in a cyclical redox reaction generating light at 620 nm. The signal was detected on the Discovery platform.

FIG. 4 illustrates the Ru-VCB/biotin-HIF-OH binding curve and linear range determination. Results are expressed as luminescence at 620 nm for Ru-VCB plus biotin-HIF-OH divided by the signal from Ru-VCB plus biotin-HIF. The assay can detect as little as 0.097 nM of hydroxylated biotin-HIF peptide standard (limit of detection=2×s/b) and is linear up to 1.56 nM.

Other embodiments of the present disclosure will be apparent to those skilled in the art from consideration of the specification and practice of the present disclosure disclosed herein. It is intended that the specification and examples be considered as exemplary only, with a true scope and spirit of the present disclosure being indicated by the following claims.

TABLE 1

| Cmpd | Structure | Name | Calc'd M.W. |
|---|---|---|---|
| 1 | 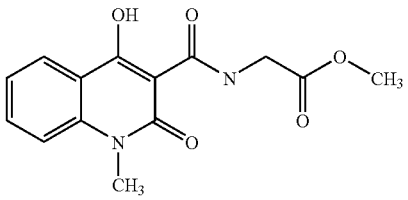 | Methyl 2-(4-hydroxy-1-methyl-2-oxo-1,2-dihydroquinoline-3-carboxamido)acetate | 290.27 |
| 2 | 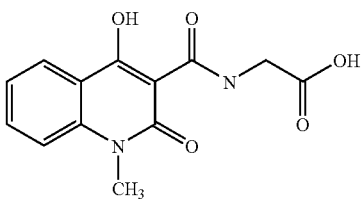 | 2-(4-hydroxy-1-methyl-2-oxo-1,2-dihydroquinoline-3-carboxamido)acetic acid | 276.24 |
| 3 | 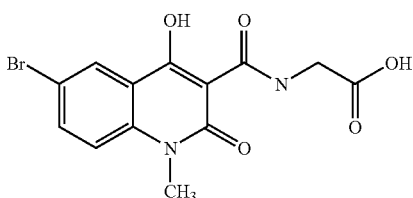 | 2-(6-bromo-4-hydroxy-1-methyl-2-oxo-1,2-dihydroquinoline-3-carboxamido)acetic acid | 355.14 |
| 4 | 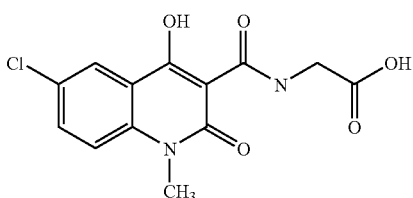 | 2-(6-chloro-4-hydroxy-1-methyl-2-oxo-1,2-dihydroquinoline-3-carboxamido)acetic acid | 310.69 |
| 5 | 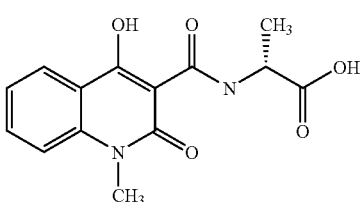 | (R)-2-(4-hydroxy-1-methyl-2-oxo-1,2-dihydroquinoline-3-carboxamido)propanoic acid | 290.27 |
| 6 | 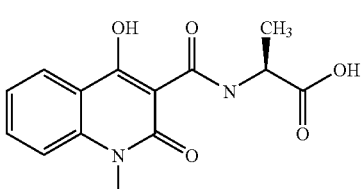 | (S)-2-(4-hydroxy-1-methyl-2-oxo-1,2-dihydroquinoline-3-carboxamido)propanoic acid | 290.27 |
| 7 | 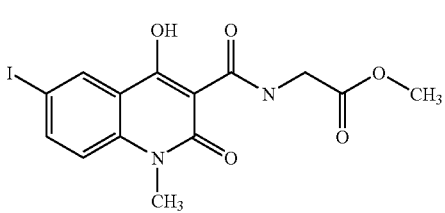 | Methyl 2-(4-hydroxy-6-iodo-1-methyl-2-oxo-1,2-dihydroquinoline-3-carboxamido)acetate | 416.17 |

TABLE 1-continued

| | | | |
|---|---|---|---|
| 8 | | 2-(4-hydroxy-6-iodo-1-methyl-2-oxo-1,2-dihydroquinoline-3-carboxamido)acetic acid | 402.14 |
| 9 | | 2-(4-hydroxy-1-methyl-2-oxo-6-phenyl-1,2-dihydroquinoline-3-carboxamido)acetic acid | 352.34 |
| 10 | | 2-(6-(4-tert-butylphenyl)-4-hydroxy-1-methyl-2-oxo-1,2-dihydroquinoline-3-carboxamido)acetic acid | 408.45 |
| 11 | | 2-(4-hydroxy-1-methyl-2-oxo-1,2-dihydroquinoline-3-carboxamido)-2-methylpropanoic acid | 304.3 |
| 12 | | (R)-2-(4-hydroxy-1-methyl-2-oxo-1,2-dihydroquinoline-3-carboxamido)-3-methylbutanoic acid | 318.12 |
| 13 | | methyl 2-(7-chloro-4-hydroxy-1-methyl-2-oxo-1,2-dihydroquinoline-3-carboxamido)acetate | 324.72 |
| 14 | | 1-(4-hydroxy-1-methyl-2-oxo-1,2-dihydroquinoline-3-carboxamido)cyclopropanecarboxylic acid | 302.28 |

TABLE 1-continued

| | | | |
|---|---|---|---|
| 15 | 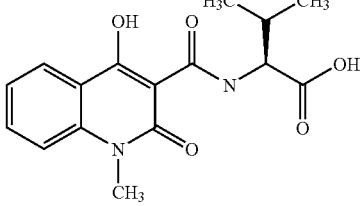 | (S)-2-(4-hydroxy-1-methyl-2-oxo-1,2-dihydroquinoline-3-carboxamido)-3-methylbutanoic acid | 318.32 |
| 16 | 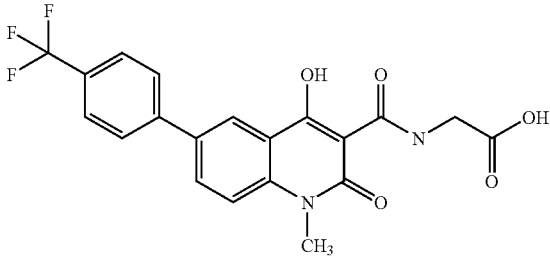 | 2-(4-hydorxy-1-methyl-2-oxo-6-(4-(trifluoromethyl)phenyl)-1,2-dihydroquinoline-3-carboxamido)acetic acid | 420.34 |
| 17 | 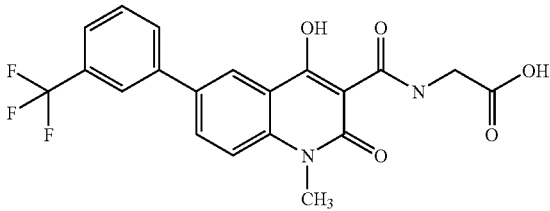 | 2-(4-hydroxy-1-methyl-2-oxo-6-(3-(trifluoromethyl)phenyl)-1,2-dihydroquinoline-3-carboxamido)acetic acid | 420.34 |
| 18 | 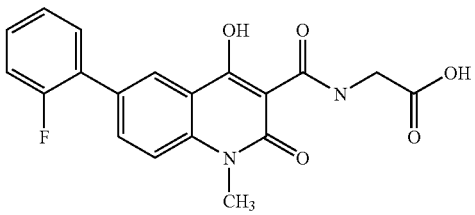 | 2-(6-(2-fluorophenyl)-4-hydroxy-1-methyl-2-oxo-1,2-dihydroquinoline-3-carboxamido)acetic acid | 370.33 |
| 19 | 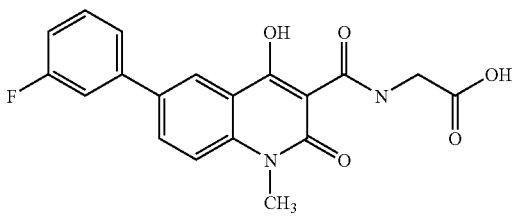 | 2-(6-(3-fluorophenyl)-4-hydroxy-1-methyl-2-oxo-1,2-dihydroquinoline-3-carboxamido)acetic acid | 370.33 |
| 20 | 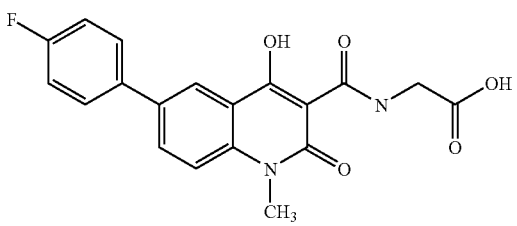 | 2-(6-(4-fluorophenyl)-4-hydroxy-1-methyl-2-oxo-1,2-dihydroquinoline-3-carboxamido)acetic acid | 370.33 |
| 21 | 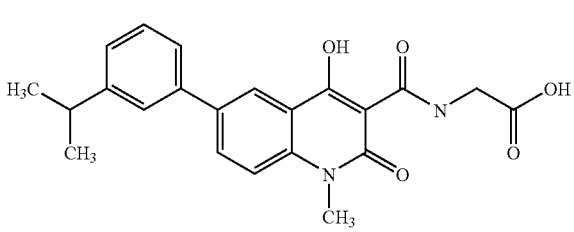 | 2-(4-hydroxy-6-(3-isopropylphenyl)-1-methyl-2-oxo-1,2-dihydroquinoline-3-carboxamido)acetic acid | 394.42 |

TABLE 1-continued

| # | Structure | Name | MW |
|---|---|---|---|
| 22 | 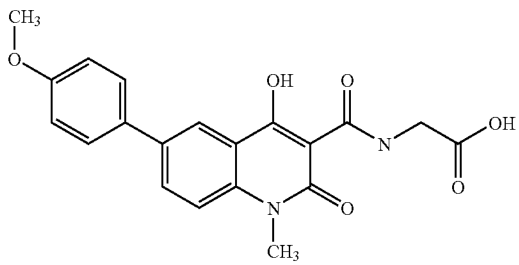 | 2-(4-hydroxy-6-(4-methoxyphenyl)-1-methyl-2-oxo-1,2-dihydroquinoline-3-carboxamido)acetic acid | 382.37 |
| 23 | 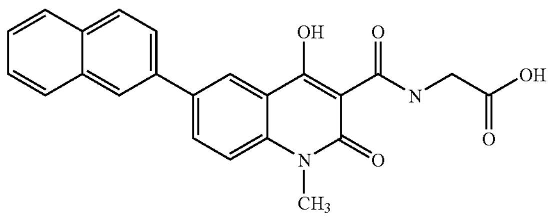 | 2-(4-hydroxy-1-methyl-6-(naphthalen-2-yl)-2-oxo-1,2-dihydroquinoline-3-carboxamido)acetic acid | 402.4 |
| 24 | 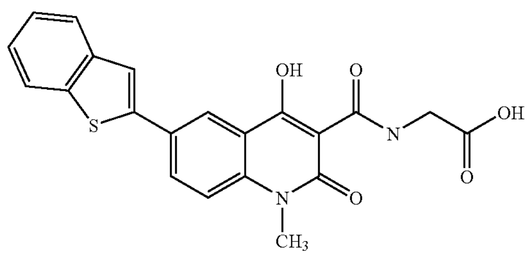 | 2-(6-(benzo[b]thiophen-2-yl)-4-hydroxy-1-methyl-2-oxo-1,2-dihydroquinoline-3-carboxamido)acetic acid | 408.43 |
| 25 | 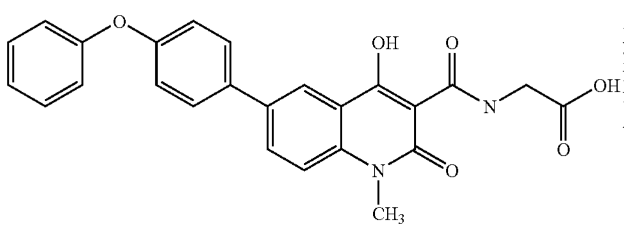 | 2-(4-hydroxy-1-methyl-2-oxo-6-(4-phenoxyphenyl)-1,2-dihydroquinoline-3-carboxamido)acetic acid | 444.44 |
| 26 | 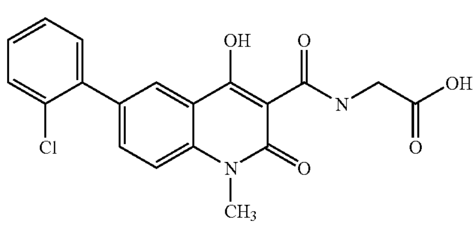 | 2-(6-(2-chlorophenyl)-4-hydroxy-1-methyl-2-oxo-1,2-dihydroquinoline-3-carboxamido)acetic acid | 386.79 |
| 27 | 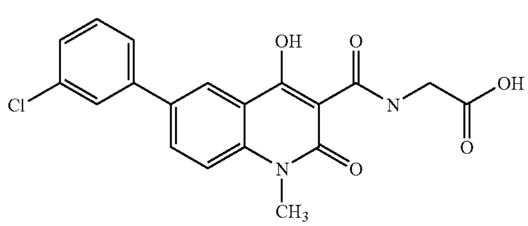 | 2-(6-(3-chlorophenyl)-4-hydroxy-1-methyl-2-oxo-1,2-dihydroquinoline-3-carboxamido)acetic acid | 386.79 |

TABLE 1-continued

| # | Structure | Name | MW |
|---|---|---|---|
| 28 | 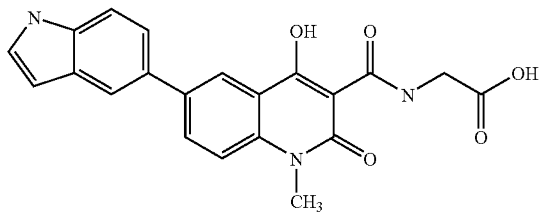 | 2-(4-hydroxy-6-(1H-indol-5-yl)-1-methyl-2-oxo-1,2-dihydroquinoline-3-carboxamido)acetic acid | 391.38 |
| 29 | 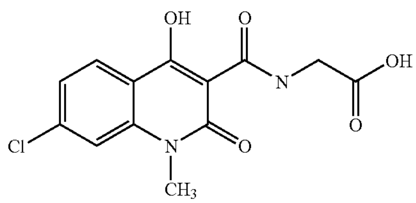 | 2-(7-chloro-4-hydroxy-1-methyl-2-oxo-1,2-dihydroquinoline-3-carboxamido)acetic acid | 310.69 |
| 30 | 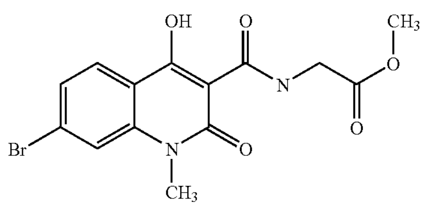 | methyl 2-(7-bromo-4-hydroxy-1-methyl-2-oxo-1,2-dihydroquinoline-3-carboxamido)acetate | 369.17 |
| 31 | 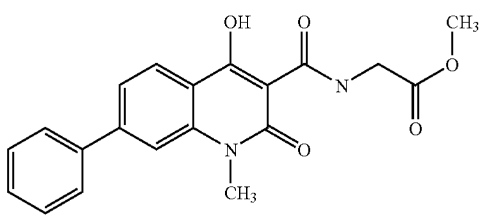 | methyl 2-(4-hydroxy-1-methyl-2-oxo-7-phenyl-1,2-dihydroquinoline-3-carboxamido)acetate | 366.37 |
| 32 | 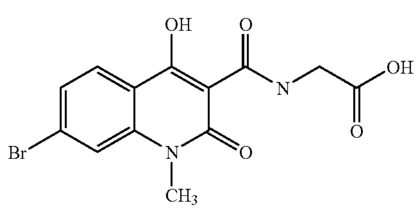 | 2-(7-bromo-4-hydroxy-1-methyl-2-oxo-1,2-dihydroquinoline-3-carboxamido)acetic acid | 355.14 |
| 33 | 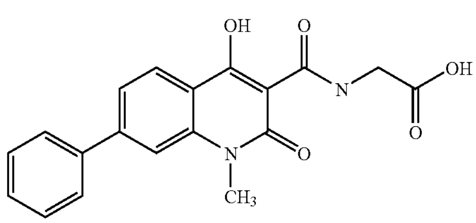 | 2-(4-hydroxy-1-methyl-2-oxo-7-phenyl-1,2-dihydroquinoline-3-carboxamido)acetic acid | 352.34 |
| 34 | 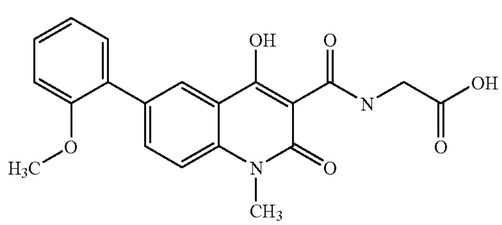 | 2-(4-hydroxy-6-(2-methoxyphenyl)-1-methyl-2-oxo-1,2-dihydroquinoline-3-carboxamido)acetic acid | 382.37 |

TABLE 1-continued

| | Structure | Name | MW |
|---|---|---|---|
| 35 | 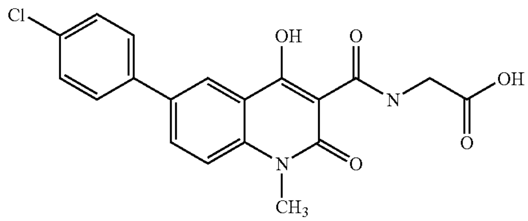 | 2-(6-(4-chlorophenyl)-4-hydroxy-1-methyl-2-oxo-1,2-dihydroquinoline-3-carboxamido)acetic acid | 386.79 |
| 36 | 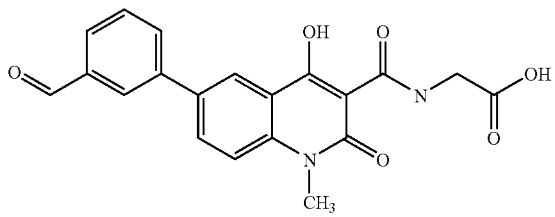 | 2-(6-(3-formylphenyl)-4-hydroxy-1-methyl-2-oxo-1,2-dihydroquinoline-3-carboxamido)acetic acid | 380.35 |
| 37 | 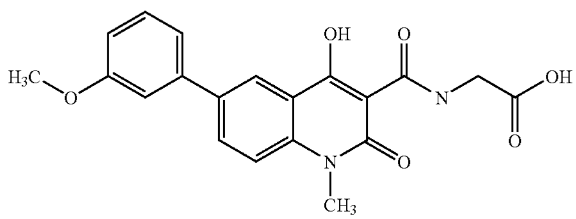 | 2-(4-hydroxy-6-(3-methoxyphenyl)-1-methyl-2-oxo-1,2-dihydroquinoline-3-carboxamido)acetic acid | 382.37 |
| 38 | 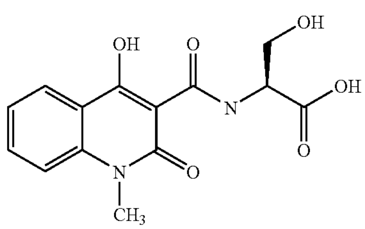 | (S)-3-hydroxy-2-(4-hydroxy-1-methyl-2-oxo-1,2-dihydroquinoline-3-carboxamido)propanoic acid | 306.27 |
| 39 | 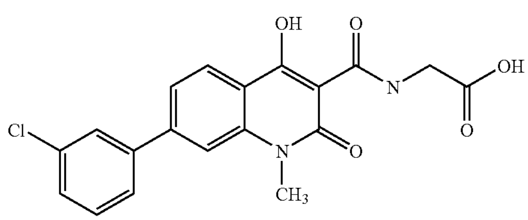 | 2-(7-(3-chlorophenyl)-4-hydroxy-1-methyl-2-oxo-1,2-dihydroquinoline-3-carboxamido)acetic acid | 386.79 |
| 40 | 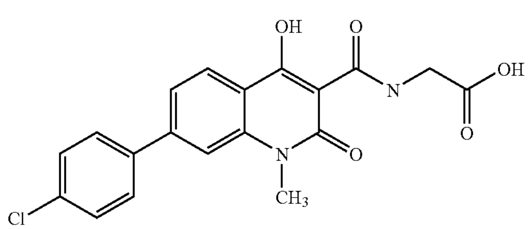 | 2-(7-(4-chlorophenyl)-4-hydroxy-1-methyl-2-oxo-1,2-dihydroquinoline-3-carboxamido)acetic acid | 386.79 |
| 41 | 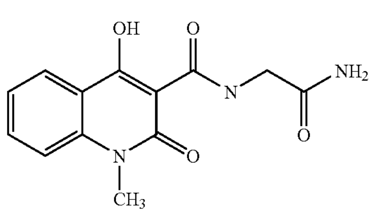 | N-(2-amino-2-oxoethyl)-4-hydroxy-1-methyl-2-oxo-1,2-dihydroquinoline-3-carboxamide | 275.26 |

TABLE 1-continued

| | | | |
|---|---|---|---|
| 42 | 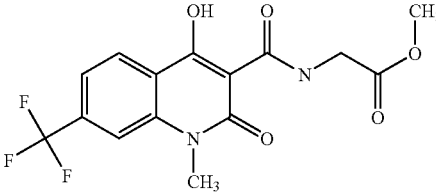 | methyl 2-(4-hydroxy-1-methyl-2-oxo-7-(trifluoromethyl)-1,2-dihydroquinoline-3-carboxamido)acetate | 358.27 |
| 43 | 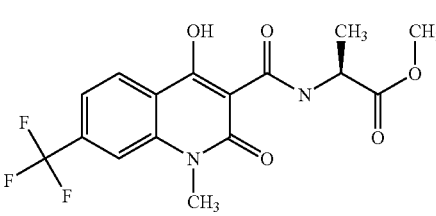 | (S)-methyl 2-(4-hydroxy-1-methyl-2-oxo-7-(trifluoromethyl)-1,2-dihydroquinoline-3-carboxamido)propanoate | 372.3 |
| 44 | 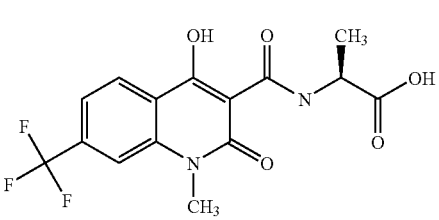 | (S)-2-(4-hydroxy-1-methyl-2-oxo-7-(trifluoromethyl)-1,2-dihydroquinoline-3-carboxamido)propanoic acid | 358.27 |
| 45 | 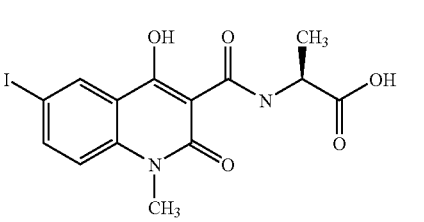 | (S)-2-(4-hydroxy-6-iodo-1-methyl-2-oxo-1,2-dihydroquinoline-3-carboxamido)propanoic acid | 416.17 |
| 46 | 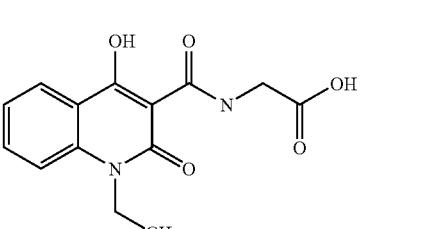 | 2-(1-ethyl-4-hydroxy-2-oxo-1,2-dihydroquinoline-3-carboxamido)acetic acid | 290.27 |
| 47 | 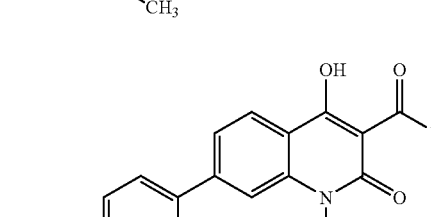 | 2-(4-hydroxy-7-(4-methoxyphenyl)-1-methyl-2-oxo-1,2-dihydroquinoline-3-carboxamido)acetic acid | 382.37 |
| 48 | 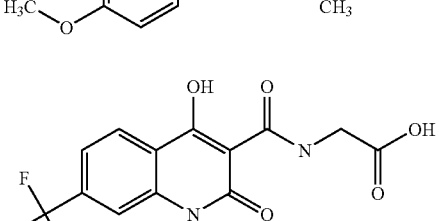 | 2-(4-hydroxy-1-methyl-2-oxo-7-(trifluoromethyl)-1,2-dihydroquinoline-3-carboxamido)acetic acid | 344.24 |

TABLE 1-continued

| | | | |
|---|---|---|---|
| 49 | 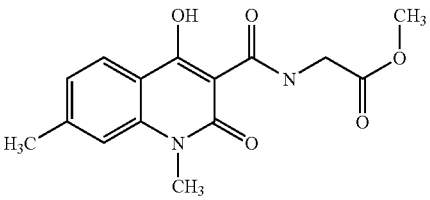 | methyl 2-(4-hydroxy-1,7-dimethyl-2-oxo-1,2-dihydroquinoline-3-carboxamido)acetate | 304.3 |
| 50 | 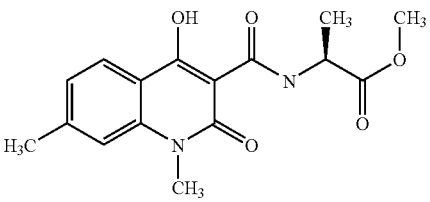 | (S)-methyl 2-(4-hydroxy-1,7-dimethyl-2-oxo-1,2-dihydroquinoline-3-carboxamido)propanoate | 318.32 |
| 51 | 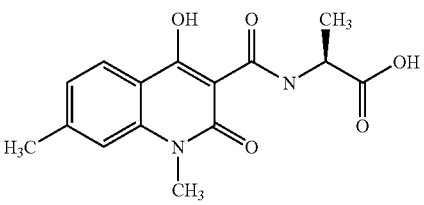 | (S)-2-(4-hydroxy-1,7-dimethyl-2-oxo-1,2-dihydroquinoline-3-carboxamido)propanoic acid | 304.3 |
| 52 | 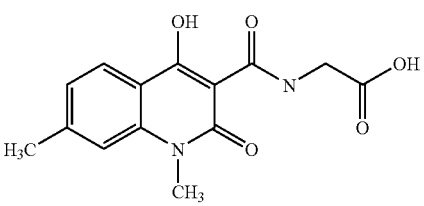 | 2-(4-hydroxy-1,7-dimethyl-2-oxo-1,2-dihydroquinoline-3-carboxamido)acetic acid | 290.27 |
| 53 | 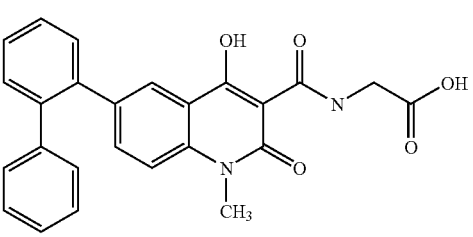 | 2-(4-hydroxy-1-methyl-2-oxo-6-(2-phenyl)-phenyl-1,2-dihydroquinoline-3-carboxamido)acetic acid | 428.44 |
| 54 | 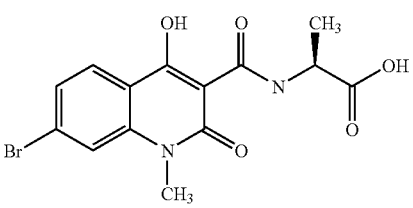 | (S)-2-(7-bromo-4-hydroxy-1-methyl-2-oxo-1,2-dihydroquinoline-3-carboxamido)propanoic acid | 369.17 |
| 55 | 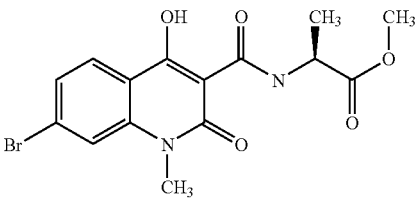 | (S)-methyl 2-(7-bromo-4-hydroxy-1-methyl-2-oxo-1,2-dihydroquinoline-3-carboxamido)propanoate | 383.19 |

TABLE 1-continued

| | | | |
|---|---|---|---|
| 56 | | (S)-2-(4-hydroxy-1-methyl-2-oxo-6-phenyl-1,2-dihydroquinoline-3-carboxamido)propanoic acid | 366.37 |
| 57 | | 2-(4-hydroxy-1-methyl-2-oxo-6-(pyridin-3-yl)-1,2-dihydroquinoline-3-carboxamido)acetic acid | 353.33 |
| 58 | | 2-(6-(2-chloro-5-methylpyrimidin-4-yl)-4-hydroxy-1-methyl-2-oxo-1,2-dihydroquinoline-3-carboxamido)acetic acid | 402.79 |
| 59 | | (S)-methyl 2-(4-hydroxy-8-methoxy-1-methyl-2-oxo-1,2-dihydroquinoline-3-carboxamido)propanoate | 334.32 |
| 60 | | methyl 2-(4-hydroxy-8-methoxy-1-methyl-2-oxo-1,2-dihydroquinoline-3-carboxamido)acetate | 320.3 |
| 61 | | 2-(4-hydroxy-1-methyl-2-oxo-6-(3-piperidin-1-yl)phenyl)-1,2-dihydroquinoline-3-carboxamido)acetic acid | 435.47 |

TABLE 1-continued

| | | | |
|---|---|---|---|
| 62 | | 2-(4-hydroxy-1-methyl-2-oxo-6-(3-(pyrrolidin-1-yl)phenyl)-1,2-dihydroquinoline-3-carboxamido)acetic acid | 421.45 |
| 63 | | ethyl 2-(4-hydroxy-6-iodo-1-methyl-2-oxo-1,2-dihydroquinoline-3-carboxamido)acetate | 430.19 |
| 64 | | (S)-2-(4-hydroxy-8-methoxy-1-methyl-2-oxo-1,2-dihydroquinoline-3-carboxamido)propanoic acid | 320.1 |
| 65 | | (S)-methyl 2-(5-fluoro-4-hydroxy-1-methyl-2-oxo-1,2-dihydroquinoline-3-carboxamido)propanoate | 322.1 |
| 66 | | methyl 2-(5-fluoro-4-hydroxy-1-methyl-2-oxo-1,2-dihydroquinoline-3-carboxamido)acetate | 308.08 |
| 67 | | 2-(4-hydroxy-8-methoxy-1-methyl-2-oxo-1,2-dihydroquinoline-3-carboxamido)acetic acid | 306.09 |
| 68 | | methyl 2-(6-fluoro-4-hydroxy-1-methyl-2-oxo-1,2-dihydroquinoline-3-carboxamido)acetate | 308.08 |

TABLE 1-continued

| | Structure | Name | MW |
|---|---|---|---|
| 69 | 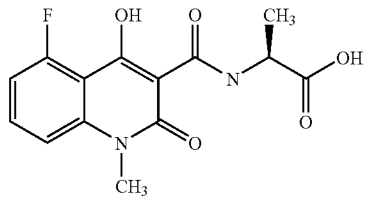 | (S)-2-(5-fluoro-4-hydroxy-1-methyl-2-oxo-1,2-dihydroquinoline-3-carboxamido)propanoic acid | 308.08 |
| 70 | 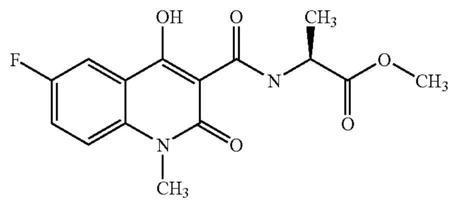 | (S)-methyl 2-(6-fluoro-4-hydroxy-1-methyl-2-oxo-1,2-dihydroquinoline-3-carboxamido)propanoate | 322.1 |
| 71 | 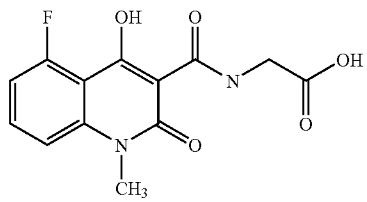 | 2-(5-fluoro-4-hydroxy-1-methyl-2-oxo-1,2-dihydroquinoline-3-carboxamido)acetic acid | 294.07 |
| 72 | 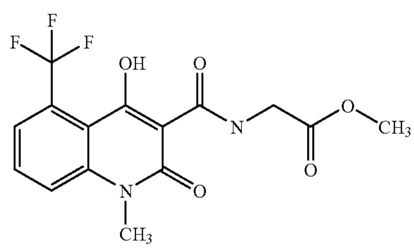 | methyl 2-(4-hydroxy-1-methyl-2-oxo-5-(trifluoromethyl)-1,2-dihydroquinoline-3-carboxamido)acetate | 358.27 |
| 73 | 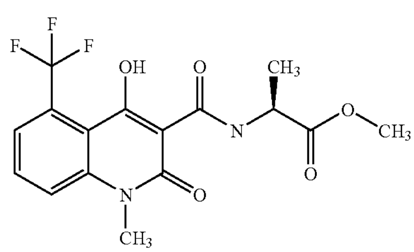 | (S)-methyl 2-(4-hydroxy-1-methyl-2-oxo-5-(trifluoromethyl)-1,2-dihydroquinoline-3-carboxamido)propanoate | 372.3 |
| 74 | 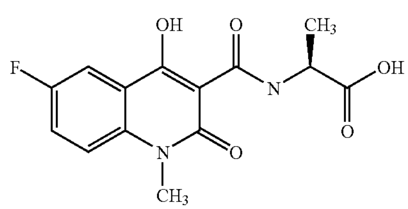 | (S)-2-(6-fluoro-4-hydroxy-1-methyl-2-oxo-1,2-dihydroquinoline-3-carboxamido)propanoic acid | 308.26 |
| 75 | 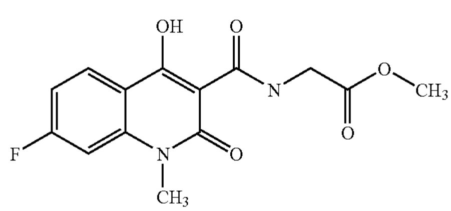 | methyl 2-(7-fluoro-4-hydroxy-1-methyl-2-oxo-1,2-dihydroquinoline-3-carboxamido)acetate | 308.26 |

TABLE 1-continued

| Cmpd | (M + H)+ | 1HNMR | Method(s) |
|---|---|---|---|
| 1 | 291 | 1H NMR(300 MHz, DMSO-d6) δ ppm 8.11(1H, d, J=7.7 Hz), 7.83(1H, t, J=7.8 Hz), 7.64(1H, d, J=8.2 Hz), 7.39(1H, t, J=7.67 Hz), 4.24(2H, d, J=5.7 Hz), 3.69(3H, s), 3.65(3H, s) | 7(with tert-butyl ester); 11, 15 |
| 2 | 277 | 1H NMR(300 MHz, DMSO-d6) δ ppm 10.57(1H, t, J=4.6 Hz), 8.09(1H, d, J=7.7 Hz), 7.82(1H, t, J=7.3 Hz), 7.63(1H, d, J=8.5 Hz), 7.38(1H, t, J=7.5 Hz), 4.14(2H, d, J=5.4 Hz), 3.64(3H, s) | 31 |
| 3 | 355 | 1H NMR(300 MHz, DMSO-d6) δ ppm 10.50 (1H, t, J=5.48 Hz), 8.14(1H, d, J=2.3 Hz), 7.96(1H, dd, J=9.1, 2.3 Hz), 7.61(1H, d, J=9.1 Hz), 4.14(2H, d, J=5.6 Hz), 3.62(3H, s) | 4, 8, 11, 15, 31 |
| 4 | 311 | 1H NMR(300 MHz, DMSO-d6) δ ppm 10.52(1H, t, J=4.8 Hz), 8.02(1H, s), 7.86(1H, d, J=9.1 Hz), 7.68(1H, d, J=8.5 Hz), 4.15(2H, d, J=5.4 Hz), 3.63(3H, s) | 4, 8, 11, 15, 31 |
| 5 | 291 | 1H NMR(400 MHz, DMSO-d6): δ ppm 10.75(1H, d, J=7.0 Hz), 8.07-8.16(1H, m), 7.80-7.87(1H, m), 7.65(1H, d, J=8.6 Hz), 7.40(1H, t, J=7.6 Hz), 4.46-4.60(1H, m, J=7.1, 7.1, 7.1 Hz), 3.65(3H, s), 1.46(3H, d, J=7.2 Hz) | 15, 31 |
| 6 | 291 | 1H NMR(400 MHz, DMSO-d6): δ ppm 10.75(1H, d, J=7.0 Hz), 8.07-8.16(1H, m), 7.80-7.87(1H, m), 7.65(1H, d, J=8.6 Hz), 7.40(1H, t, J=7.6 Hz), 4.46-4.60(1H, m, J=7.1, 7.1, 7.1 Hz), 3.65(3H, s), 1.46(3H, d, J=7.2 Hz) | 15, 31 |
| 7 | 417 | NMR 300(D6-DMSO): δ ppm 10.53(1H, t, J=3.0 Hz), 8.30(1H, d, J=2.0 Hz), 8.08(1H, dd, J=3.0 Hz, 9.0 Hz), 7.45(1H, d, J=9.0 Hz), 4.23(2H, d, J=6.0 Hz), 3.69(3H, s), 3.60(3H, s). | 15 |
| 8 | 403 | NMR 300(D6-DMSO): δ ppm 12.98(1H, br s), 10.50(1H, br t), 8.31(1H, d, J=3.0 Hz), 8.08(1H, dd, J=3 Hz, | 31 |

TABLE 1-continued

| | | | |
|---|---|---|---|
| | | J=9.0 Hz), 7.45(1H, d, J=9 Hz), 4.13(2H, d, J=6.0 Hz), 3.60(3H, s). | |
| 9 | 353 | NMR 300(D6-DMSO): δ ppm 12.95(1H, br s), 10.58(1H, br t), 8.31(1H, br s), 8.15(1H, m), 7.76(3H, m), 7.52(2H, m), 7.41(1H, m), 4.15(2H, d, J=6 Hz), 3.69(3H, s). | 19, 31 |
| 10 | 409 | NMR 300(D6-DMSO): δ ppm 12.97(1H, br s), 10.60(1H, br m), 8.28(1H, br s), 8.12(1H, m), 7.70(3H, m), 7.53(2H, m), 4.16(2H, br m), 3.68(3H, s), 1.33(9H, s). | 19, 31 |
| 11 | 305 | 1H NMR(400 MHz, DMSO-d6): δ ppm 12.82(1H, s), 10.80-10.86(1H, m), 8.10(1H, d, J=8.0 Hz), 7.83(1H, t, J=7.8 Hz), 7.65(1H, d, J=8.6 Hz), 7.39(1H, t, J=7.5 Hz), 3.64(3H, s), 1.57(6H, s) | 15, 31 |
| 12 | 319 | 1H NMR(400 MHz, DMSO-d6): δ ppm 8.10(1H, d, J=9.4 Hz), 7.83(1H, d), 7.64(1H, d), 7.40(1H, dd), 0.95(6H, d) | 15, 31 |
| 13 | 325 | 1H NMR(400 MHz, CHLOROFORM-d) δ ppm 10.65(1H, s), 8.13(1H, d, J=8.4 Hz), 7.37(1H, s), 7.26(1H, s), 4.24(2H, d, J=5.7 Hz), 3.80(3H, s), 3.66(3H, s). | 14 |
| 14 | 303 | | 15, 31 |
| 15 | 319 | 1H NMR(400 MHz, DMSO-d6) δ ppm 10.84(1H, d, J=8.2 Hz), 8.10(1H, dd, J=8.0, 1.2 Hz), 7.81-7.86(1H, m), 7.66(1H, d, J=8.6 Hz), 7.40(2H, t, J=7.5 Hz), 4.47(1H, dd, J=8.4, 4.5 Hz), 3.66(3H, s), 0.97(6H, dd, J=6.8, 2.3 Hz) | 15, 31 |
| 16 | 421 | NMR 300(D6-DMSO): δ ppm 12.98(1H, br s), 10.58(1H, br t), 8.40(1H, d, J=3.0 Hz), 8.25(1H, dd, J=3.0, J=9.0 Hz), 8.03(2H, d, J=9.0 Hz), 7.88(2H, d, J=9.0 Hz), 7.80(1H, d, J=9.0 Hz), 4.18(2H, m), 3.72(3H, s). | 19, 31 |
| 17 | 421 | NMR 300(D6-DMSO): δ ppm 10.63(1H, br s), 8.42(1H, s), 8.26(1H, m), 8.12(2H, m), 7.88(2H, d, J=9.0 Hz), 7.80(3H, m), 3.90(2H, br s), 3.73(3H, s). | 19, 31 |
| 18 | 371 | NMR 300(D6-DMSO): δ ppm 13.04(1H, br s), | 19, 31 |

TABLE 1-continued

| | | 10.67(1H, br t), 8.34(1H, s), 8.13(1H, d, J=9.0 Hz), 7.87(1H, d, J=9.0 Hz), 7.76(1H, m), 7.57(1H, m), 7.46(2H, m), 4.26(2H, m), 3.80(3H, s). | |
|---|---|---|---|
| 19 | 371 | NMR 300(D6-DMSO): δ ppm 13.02(1H, br s), 10.62(1H, br t), 8.38(1H, d, J=3 Hz), 8.24(1H, dd, J=3 Hz, J=9.0 Hz), 7.80(1H, d, J=9.0 Hz), 7.71-7.56(3H, m), 7.29(1H, m), 4.20(2H, m), 3.74(3H, s). | 19, 31 |
| 20 | 371 | NMR 300(D6-DMSO): δ ppm 13.07(1H, br s), 10.70(1H, br t), 8.39(1H, d, J=3 Hz), 8.25(1H, dd, J=3 Hz, J=9.0 Hz), 7.96-7.91(2H, m), 7.85(1H, d, J=9.0 Hz), 7.46(2H, m), 4.27(2H, m), 3.81(3H, s). | 19, 31 |
| 21 | 395 | NMR 300(D6-DMSO): δ ppm 12.80(1H, br s), 10.44(1H, br t), 8.14(1H, d, J=3 Hz), 8.00(1H, dd, J=3 Hz, J=9.0 Hz), 7.58(1H, d, J=9.0 Hz), 7.42(2H, m), 7.29(1H, t, J=9.0 Hz), 7.15(1H, d, J=9.0 Hz), 4.01(2H, m), 3.54(3H, s), 2.86(1H, m), 1.13(6H, d, J=6.0 Hz). | 19, 31 |
| 22 | 383 | NMR 300(D6-DMSO): δ ppm 12.95(1H, br s), 10.59(1H, br t), 8.24(1H, d, J=3 Hz), 8.10(1H, dd, J=3 Hz, J=9.0 Hz), 7.70(3H, m), 7.06(2H, J=9.0 Hz), 4.14(2H, d, J=6 Hz), 3.81(3H, s), 3.68(3H, s). | 19, 31 |
| 23 | 403 | NMR 300(D6-DMSO): δ ppm 12.96(1H, br s), 10.59(1H, br t), 8.46(1H, d, J=3 Hz), 8.34-8.29(2H, m), 8.05(2H, d, J=9.0 Hz), 7.96(2H, m), 7.78(1H, d, J=9.0 Hz), 7.56(2H, m), 4.16(2H, m), 3.81(3H, s). | 19, 31 |
| 24 | 409 | NMR 300(D6-DMSO): δ ppm 10.56(1H, br s), 8.33(1H, s), 8.21(1H, m), 7.99(2H, m), 7.87(1H, m), 7.71(1H, m), 7.39(2H, m), 3.86(2H, br s), 3.66(3H, s). | 19, 31 |
| 25 | 445 | NMR 300(D6-DMSO): δ ppm 12.93(1H, br s), 10.58(1H, br s), 8.27(1H, d, J=6.0 Hz), 8.13(1H, dd, J=3.0 Hz, J=9.0 Hz), 7.81-7.71(3H, | 19, 31 |

TABLE 1-continued

| | | | |
|---|---|---|---|
| | | m), 7.44(2H, m), 7.21-7.08(5H, m), 4.15(2H, m), 3.68(3H, s). | |
| 26 | 387 | NMR 300(D6-DMSO): δ ppm 12.95(1H, br s), 10.57(1H, br m), 8.11(1H, br s), 7.92(1H, m), 7.74(1H, m), 7.62(1H, m), 7.48(3H, m), 4.15(2H, m), 3.70(3H, s). | 19, 31 |
| 27 | 387 | NMR 300(D6-DMSO): δ ppm 12.95(1H, br s), 10.56(1H, br m), 8.30(1H, d, J=3.0 Hz), 8.18(1H, dd, J=3.0 Hz, J=9.0 Hz), 7.83(1H, s), 7.73(2H, m), 7.56-7.46(2H, m), 4.15(2H, m), 3.68(3H, s). | 19, 31 |
| 28 | 392 | NMR 300(D6-DMSO): δ ppm 12.95(1H, br s), 11.21(1H, br s), 10.62(1H, br t), 8.30(1H, d, J=3.0 Hz), 8.16(1H, dd, J=3.0 Hz, J=9.0 Hz), 7.92(1H, s), 7.71(1H, d, J=9.0 Hz), 7.51(2H, m), 7.40(1H, m), 6.53(1H, s), 4.16(2H, m), 3.69(3H, s). | 19, 31 |
| 29 | 311 | 1H NMR(400 MHz, DMSO-d6) δ ppm 10.42-10.53(1H, m), 8.09(1H, d, J=8.6 Hz), 7.73-7.76(1H, m), 7.41-7.46(1H, m), 4.13(2H, d, J=5.5 Hz), 3.60-3.66(3H, m) | 31 |
| 30 | 370 | 1H NMR(400 MHz, DMSO-d6) δ ppm 10.43-10.57(1H, m), 8.01(1H, d, J=8.4 Hz), 7.85-7.89(1H, m), 7.54-7.58(1H, m), 4.24(2H, d, J=5.9 Hz), 3.69(3H, s), 3.63(3H, s) | 14 |
| 31 | 367 | 1H NMR(400 MHz, DMSO-d6) δ ppm 10.57-10.62(1H, m), 8.17(1H, d, J=8.4 Hz), 7.88(2H, d, J=7.4 Hz), 7.79-7.82(1H, m), 7.71(1H, d, J=8.6 Hz), 7.53-7.59(2H, m), 7.46-7.51(1H, m), 4.25(2H, d, J=5.9 Hz), 3.74-3.78(3H, m), 3.69-3.72(3H, m) | 21 |
| 32 | 355 | 1H NMR(400 MHz, DMSO-d6) δ ppm 10.39-10.51(1H, m), 7.99(1H, d, J=8.6 Hz), 7.82-7.88(1H, m), 7.55(1H, d, J=8.6 Hz), 4.14(2H, d, J=5.5 Hz), 3.59-3.67(3H, m) | 31 |
| 33 | 353 | 1H NMR(400 MHz, DMSO-d6) δ ppm 10.57(1H, t, J=5.5 Hz), 8.17(1H, d, J=8.2 Hz), 7.88(2H, d, J=7.4 Hz), 7.79-7.83(1H, | 31 |

TABLE 1-continued

| | | | |
|---|---|---|---|
| | | m), 7.70(1H, dd, J=8.4, 1.2 Hz), 7.53-7.59(2H, m), 7.46-7.51(1H, m), 4.15(2H, d, J=5.7 Hz), 3.74-3.78(3H, m) | |
| 34 | 383 | NMR 300(D6-DMSO): δ ppm 12.94(1H, br s), 10.59(1H, br s), 8.16(1H, s), 7.94(1H, d, J=9.0 Hz), 7.67(1H, d, J=9.0 Hz), 7.40(2H, m), 7.16(1H, m), 7.07(1H, m), 4.14(2H, m), 3.80(3H, m), 3.68(3H, s). | 19, 31 |
| 35 | 387 | NMR 300(D6-DMSO): δ ppm 12.94(1H, br s), 10.59(1H, br s), 8.16(1H, s), 7.94(1H, d, J=9.0 Hz), 7.67(1H, d, J=9.0 Hz), 7.40(2H, m), 7.16(1H, m), 7.07 (1H, m), 4.14(2H, m), 3.68(3H, s). | 19, 31 |
| 36 | 381 | NMR 300(D6-DMSO): δ ppm 12.96(1H, br s), 10.56(1H, br s), 10.14(1H, s), 8.39(1H, s), 8.30(1H, s), 8.23(1H, m), 8.13(1H, m), 7.93(1H, m), 7.76(2H, m), 4.15(2H, m), 3.69(3H, s). | 19, 31 |
| 37 | 383 | NMR 300(D6-DMSO): δ ppm 10.63(1H, br s), 10.14(1H, s), 8.42(1H, s), 7.76(1H, d, J=9.0 Hz), 7.40-7.19(4H, m), 6.90(1H, d, J=9.0 Hz), 3.83(3H, s), 3.52(2H, br s), 3.50(3H, s). | 19, 31 |
| 38 | 307 | 1H NMR(400 MHz, DMSO-d6): δ ppm 10.84(1H, d, J=8.2 Hz), 8.10(1H, dd, J=8.0, 1.2 Hz), 7.81-7.86(1H, m), 7.66(1H, d, J=8.6 Hz), 7.40(2H, t, J=7.5 Hz), 4.47(1H, dd, J=8.4, 4.5 Hz), 3.92-3.76(2H, m), 3.66(3H, s). | 15, 31 |
| 39 | 387 | 1H NMR(400 MHz, DMSO-d6) δ ppm 10.50-10.61(1H, m), 8.17(1H, d, J=8.4 Hz), 7.96-8.02(1H, m), 7.81-7.89(2H, m), 7.69-7.75(1H, m), 7.50-7.63(2H, m), 4.15(2H, d, J=5.5 Hz), 3.78(3H, s) | 21, 31 |
| 40 | 387 | 1H NMR(400 MHz, DMSO-d6) δ ppm 10.51-10.60(1H, m), 8.13-8.21(1H, m), 7.88-7.96(2H, m), 7.78-7.84(1H, m), 7.66-7.73(1H, m), 7.57-7.65(2H, m), 4.15(2H, d, J=4.5 Hz), 3.70-3.81(3H, m) | 21, 31 |
| 41 | 276 | 1H NMR(300 MHz, DMSO-d6) δ ppm 10.58(1H, | 8, 11; 15 (with |

TABLE 1-continued

| | | | |
|---|---|---|---|
| | | t, J=4.9 Hz), 8.10(1H, d, J=8.0 Hz), 7.82(1H, t, J=7.09 Hz), 7.63(1H, d, J=8.3 Hz), 7.57(1H, s), 7.38(1H, t, J=7.5 Hz), 7.21(1H, s), 4.02(2H, d, J=5.1 Hz), 3.64(3H, s) | glycinamide) |
| 42 | 359 | 1H NMR(400 MHz, DMSO-d6) δ ppm 10.45-10.56(1H, m), 8.28(1H, d, J=8.2 Hz), 7.86-7.93(1H, m), 7.69(1H, d, J=8.2 Hz), 4.20-4.31(2H, m), 3.67-3.72(6H, m) | 14 |
| 43 | 373 | 1H NMR(400 MHz, DMSO-d6) δ ppm 10.61-10.70(1H, m), 8.28(1H, d, J=8.4 Hz), 7.89-7.93(1H, m), 7.69(1H, d, J=8.4 Hz), 4.59-4.71(1H, m), 3.67-3.73(6H, m), 1.48(3H, d, J=7.2 Hz) | 14 with S-ala |
| 44 | 359 | 1H NMR(400 MHz, DMSO-d6) δ ppm 10.67(1H, d, J=6.8 Hz), 8.29(1H, d, J=8.2 Hz), 7.88-7.95(1H, m), 7.70(1H, d, J=8.4 Hz), 4.45-4.65(1H, m), 3.64-3.75(3H, m), 1.47(3H, d, J=7.0 Hz) | 31 |
| 45 | 417 | 1H NMR(300 MHz, DMSO-d6) δ ppm 13.12(1H, s), 10.67(1H, d, J=7.0 Hz), 8.29(1H, s), 8.07(1H, dd, J=8.9, 2.0 Hz), 7.45(1H, d, J=9.1 Hz), 4.45-4.60(1H, m), 3.59(3H, s), 1.45(3H, d, J=7.2 Hz) | 14, 31 |
| 46 | 291 | 1H NMR(300 MHz, DMSO-d6) δ ppm 10.58(1H, t, J=5.48 Hz), 8.12(1H, dd, J=8.1, 1.4 Hz), 7.81(1H, t, J=7.2, 1.5 Hz), 7.68(1H, d, J=8.6 Hz), 7.38(1H, t, J=7.4 Hz), 4.32(2H, q, J=7.0 Hz), 4.14(2H, d, J=5.6 Hz), 1.23(3H, t, J=7.0 Hz) | 4 with Etl, 7, 17, 31 |
| 47 | 383 | 1H NMR(400 MHz, DMSO-d6) δ ppm 10.47-10.64(1H, m), 8.10-8.18(1H, m), 7.81-7.90(2H, m), 7.71-7.78(1H, m), 7.63-7.71(1H, m), 7.07-7.16(2H, m), 4.09-4.18(2H, m), 3.85(3H, s), 3.75(3H, s) | 21, 31 |
| 48 | 345 | 1H NMR(400 MHz, DMSO-d6) δ ppm 12.88-13.02(1H, m), 10.44-10.54(1H, m), 8.30(1H, d, J=8.2 Hz), 7.88-7.93(1H, m), 7.69(1H, d, J=8.4 Hz), 4.15(2H, d, J=5.7 Hz), 3.67-3.74(3H, m) | 31 |

TABLE 1-continued

| | | | |
|---|---|---|---|
| 49 | 305 | 1H NMR(400 MHz, DMSO-d6) δ ppm 10.54-10.63(1H, m), 7.97(1H, d, J=8.2 Hz), 7.43-7.49(1H, m), 7.21(1H, d, J=8.2 Hz), 4.23(2H, d, J=5.9 Hz), 3.67-3.73(3H, m), 3.60-3.65(3H, m) | 14 |
| 50 | 319 | 1H NMR(400 MHz, DMSO-d6) δ ppm 10.64-10.78(1H, m), 7.93(1H, d, J=8.2 Hz), 7.37-7.46(1H, m), 7.18(1H, d, J=8.0 Hz), 4.55-4.68(1H, m), 3.68-3.75(3H, m), 3.56-3.62(3H, m), 2.45-2.51(3H, m), 1.46(3H, d, J=7.0 Hz) | 14 with S-ala-OMe |
| 51 | 305 | 1H NMR(400 MHz, DMSO-d6) δ ppm 10.72(1H, d, J=7.0 Hz), 7.99(1H, d, J=8.2 Hz), 7.43-7.51(1H, m), 7.18-7.26(1H, m), 4.42-4.59(1H, m), 3.58-3.67(3H, m), 1.44(3H, d, J=7.0 Hz) | 31 |
| 52 | 291 | 1H NMR(400 MHz, DMSO-d6) δ ppm 10.46-10.63(1H, m), 7.90-8.06(1H, m), 7.40-7.52(1H, m), 7.17-7.29(1H, m), 4.02(2H, d, J=5.1 Hz), 3.60-3.66(3H, m) | 31 |
| 53 | 429 | NMR 300(D6-DMSO): δ ppm 10.55(1H, br m), 7.85(1H, s), 7.49(3H, m), 7.45(3H, m), 7.24(3H, m), 7.15(2H, m), 3.88(2H, m), 3.58(3H, s)ppm. | 19, 31 |
| 54 | 370 | 1H NMR(400 MHz, DMSO-d6) δ ppm 10.63(1H, d, J=6.7 Hz), 7.98(1H, d, J=8.4 Hz), 7.82-7.89(1H, m), 7.51-7.59(1H, m), 4.45-4.59(1H, m), 3.56-3.68(3H, m), 1.45(3H, d, J=7.2 Hz) | 31 |
| 55 | 384 | 1H NMR(400 MHz, DMSO-d6) δ ppm 10.62(1H, d, J=7.0 Hz), 7.96-8.03(1H, m), 7.83-7.91(1H, m), 7.50-7.60(1H, m), 4.55-4.70(1H, m), 3.67-3.73(3H, m), 3.59-3.65(3H, m), 1.47(3H, d, J=7.2 Hz) | 14 with S-ala |
| 56 | 367 | 1H NMR(300 MHz, DMSO-d6) δ ppm 13.10(1H, s), 10.75(1H, d, J=7.2 Hz), 8.29(1H, s), 8.15(1H, dd, J=9.0, 1.8 Hz), 7.69-7.82(3H, m), 7.52(2H, t, J=7.5 Hz), 7.41(1H, t, J=7.3 Hz), 4.43-4.64(1H, m), 3.68(3H, s), 1.47(3H, d, J=7.0 Hz) | 14(with L-alanine); 19, 31 |

TABLE 1-continued

| | | | |
|---|---|---|---|
| 57 | 354 | 1H NMR(300 MHz, DMSO-d6) δ ppm 10.55(1H, s), 9.17(1H, s), 8.75(1H, d, J=5.8 Hz), 8.49-8.61(1H, m), 8.44(1H, s), 8.27(1H, d, J=8.6 Hz), 7.81(2H, d, J=8.5 Hz), 4.16(2H, d, J=4.5 Hz), 3.70(3H, s) | 19, 31 |
| 58 | 403 | NMR 300(D6-DMSO): δ ppm 10.55(1H, br m), 8.73(1H, s), 8.44(1H, s), 8.13(1H, d, J=9.0 Hz), 7.72(1H, d, J=9.0 Hz), 3.82(2H, m), 3.67(3H, s), 2.54(3H, s) ppm. | 20, 31 |
| 59 | 335 | 1H NMR(400 MHz, DMSO-d6): δ ppm 10.77(1H, d, J=7.0 Hz), 7.71(1H, d, J=7.8 Hz), 7.46(1H, d, J=7.6 Hz), 7.33(1H, t, J=8.0 Hz), 4.59-4.66(1H, m, J=7.0, 7.0, 7.0 Hz), 3.92(3H, s), 3.81(3H, s), 1.46(3H, d, J=7.2 Hz) | 16 |
| 60 | 321 | 1H NMR(400 MHz, DMSO-d6): δ ppm 10.61(1H, t, J=5.7 Hz), 7.70(1H, d, J=7.8 Hz), 7.45(1H, d, J=8.0 Hz), 7.32(1H, t, J=8.0 Hz), 4.23(2H, d, J=5.7 Hz), 3.92(3H, s), 3.81(3H, s), 3.69(3H, s) | 16 |
| 61 | 436 | 1H NMR(300 MHz, DMSO-d6) δ ppm 10.54-10.61(1H, m), 8.33(1H, s), 8.16(1H, d, J=10.7 Hz), 7.74(1H, d, J=9.8 Hz), 7.36-7.59(3H, m), 4.16(2H, d, J=5.0 Hz), 3.69(3H, s), 3.35-3.52(4H, m), 1.71(6H, d, J=52.8 Hz) | 19, 31 |
| 62 | 422 | 1H NMR(300 MHz, DMSO-d6) δ ppm 10.59(1H, t, J=5.9 Hz), 8.26(1H, s), 8.11(1H, d, J=10.5 Hz), 7.71(1H, d, J=8.5 Hz), 7.29(1H, t, J=8.0 Hz), 6.95(1H, d, J=6.1 Hz), 6.82(1H, s), 6.61(1H, d, J=9.8 Hz), 4.16(2H, d, J=4.7 Hz), 3.69(3H, s), 3.33(4H, t, J=6.4 Hz), 1.99(4H, t, J=5.9 Hz) | 19, 31 |
| 63 | 431 | NMR 300(D6-DMSO): δ ppm 10.52(1H, br m), 8.30(1H, d, J=3.0 Hz), 8.08(1H, dd, J=3.0 Hz, J=9.0 Hz), 7.45(1H, d, J=9.0 Hz), 4.22-4.12(4H, m), 3.61(3H, s), 1.22(3H, t, J=6.0 Hz)ppm. | 14 |
| 64 | 321 | 1H NMR(400 MHz, DMSO-d6): δ ppm 10.76(1H, d, J=6.8 Hz), | 31 |

TABLE 1-continued

| | | | |
|---|---|---|---|
| | | 7.70(1H, d, J=8.0 Hz), 7.45(1H, d, J=8.0 Hz), 7.32(1H, t, J=8.0 Hz), 4.48-4.56(1H, m), 3.91(3H, s), 3.81(3H, s), 1.45(3H, d, J=7.0 Hz) | |
| 65 | 323 | 1H NMR(400 MHz, DMSO-d6): δ ppm 10.77(1H, d, J=6.8 Hz), 7.75-7.84(1H, m), 7.46(1H, d, J=8.6 Hz), 7.16(1H, dd, J=11.6, 8.1 Hz), 4.57-4.67(1H, m), 3.71(3H, s), 3.63(3H, s), 1.46(3H, d, J=7.2 Hz) | 16 |
| 66 | 309 | 1H NMR(400 MHz, DMSO-d6): δ ppm 10.62(1H, t, J=5.7 Hz), 7.74-7.84(1H, m), 7.45(1H, d, J=8.6 Hz), 7.11-7.20(1H, m), 4.23(2H, d, J=5.9 Hz), 3.69(3H, s), 3.63(3H, s) | 16 |
| 67 | 307 | 1H NMR(400 MHz, DMSO-d6): δ ppm 10.58(1H, t, J=5.6 Hz), 7.70(1H, d, J=8.0 Hz), 7.44(1H, d, J=7.8 Hz), 7.32(1H, t, J=8.0 Hz), 4.13(2H, d, J=5.5 Hz), 3.91(3H, s), 3.81(3H, s) | |
| 68 | 309 | 1H NMR(400 MHz, DMSO-d6): δ ppm 10.56 10.66(1H, m), 7.80(1H, dd, J=8.5, 2.2 Hz), 7.69-7.75(2H, m), 4.24(2H, d), 3.78-3.82(3H, m), 3.68-3.71(3H, m) | 16 |
| 69 | 309 | 1H NMR(400 MHz, DMSO-d6): δ ppm 10.76(1H, d, J=6.8 Hz), 7.74-7.84(1H, m), 7.45(1H, d, J=8.6 Hz), 7.15(1H, dd, J=11.8, 8.1 Hz), 4.45-4.56(1H, m), 3.62(3H, s), 1.45(3H, d, J=7.2 Hz) | 31 |
| 70 | 323 | 1H NMR(400 MHz, DMSO-d6): δ ppm 10.68 10.79(1H, m), 7.76(1H, d), 7.67-7.73(1H, m), 4.57-4.69(1H, m), 3.71(3H, s), 3.62(3H, s), 1.46(3H, d, J=7.2 Hz) | 16 |
| 71 | 295 | 1H NMR(400 MHz, DMSO-d6): δ ppm 12.94(1H, br. s.), 10.58-10.61(1H, m), 7.73-7.85(1H, m), 7.46(1H, d, J=8.8 Hz), 7.11-7.21(1H, m), 4.13(2H, d, J=5.5 Hz), 3.62-3.65(3H, s) | 31 |
| 72 | 359 | 1H NMR(400 MHz, DMSO-d6): δ ppm 10.67 10.78(1H, m), 8.00-8.06(1H, m), 7.92-7.99(1H, m), 7.82-7.87(1H, m), 4.25(2H, d, J=5.3 Hz), 3.71(3H, s), 3.70(3H, s) | 16 |

TABLE 1-continued

| | | | | | |
|---|---|---|---|---|---|
| | 73 | 373 | 1H NMR(400 MHz, DMSO-d6): δ ppm 10.91 11.01(1H, m), 7.73-8.00(2H, m), 7.34-7.40(1H, m), 4.55-4.67(1H, m), 3.70(3H, s), 3.66(3H, s), 1.45(3H, d, J=7.0 Hz) | | 16 |
| | 74 | 309 | 1H NMR(400 MHz, DMSO-d6): δ ppm 10.75(1H, d, J=6.8 Hz), 7.79(1H, d, J=8.8 Hz), 7.67-7.75(2H, m), 4.46-4.59(1H, m), 3.64(3H, s), 1.46(3H, d, J=7.2 Hz) | | 31 |
| | 75 | 309 | 1H NMR(400 MHz, DMSO-d6): δ ppm 10.49(1H, t, J=5.7 Hz), 8.15(1H, dd, J=8.8, 6.5 Hz), 7.54(1H, dd, J=11.6, 2.2 Hz), 7.21-7.30(1H, m), 4.22(2H, d, J=5.9 Hz), 3.69(3H, s), 3.61(3H, s) | | 16 |

TABLE 1

| Cmpd | Structure | Name | Calc'd M.W. | (M + H)+ | 1HNMR | Method(s) |
|---|---|---|---|---|---|---|
| 76 | 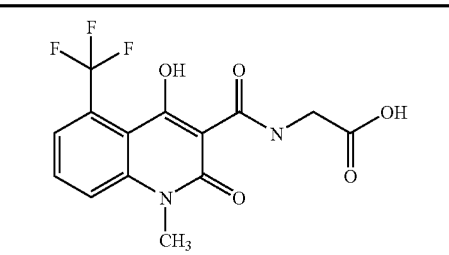 | 2-(4-hydroxy-1-methyl-2-oxo-5-(trifluoromethyl)-1,2-dihydro-quinolin-3-carboxamido)-acetic acid | 344.24 | 345 | 1H NMR(400 MHz, DMSO-d6): δ ppm 10.70(1H, t, J=5.1 Hz), 7.99-8.04(1H, m), 7.95(1H, t, J=8.0 Hz), 7.84(1H, d, J=7.4 Hz), 4.15(2H, d, J=5.7 Hz), 3.70(3H, s) | 31 |
| 77 | 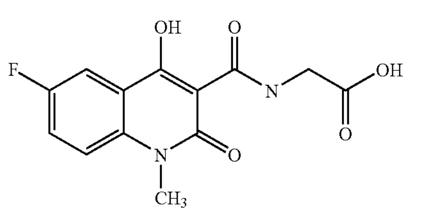 | 2-(6-fluoro-4-hydroxy-1-methyl-2-oxo-1,2-dihydro-quinolin-3-carboxamido)-acetic acid | 294.24 | 295 | 1H NMR(400 MHz, DMSO-d6): δ ppm 10.57(1H, t, J=5.4 Hz), 7.80(1H, dd, J=8.6, 2.5 Hz), 7.67-7.75 (2H, m), 4.14(2H, d, J=5.5 Hz), 3.65(3H, s) | 31 |
| 78 | 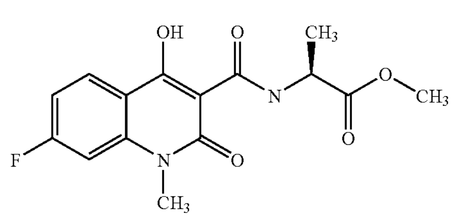 | (S)-methyl 2-(7-fluoro-4-hydroxy-1-methyl-2-oxo-1,2-dihydro-quinolin-3-carboxamido)-propanoate | 322.29 | 323 | 1H NMR(400 MHz, DMSO-d6): δ ppm 8.16(1H, dd, J=8.8, 6.7 Hz), 7.54(1H, dd, J=11.5, 2.0 Hz), 7.22-7.30(1H, m), 4.57-4.68(1H, m), 3.70(3H, s), 3.61(3H, s), 1.38(3H, d, J=7.0 Hz) | 16 |

TABLE 1-continued

| Cmpd | Structure | Name | Calc'd M.W. | (M + H)+ | 1HNMR | Method(s) |
|---|---|---|---|---|---|---|
| 79 | 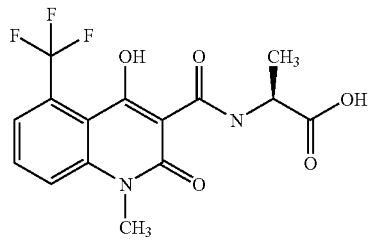 | (S)-2-(4-hydroxy-1-methyl-2-oxo-5-(trifluoromethyl)-1,2-dihydro-quinoline-3-carboxamido)-propanoic acid | 358.27 | 359 | 1H NMR(400 MHz, DMSO-d6): δ ppm 10.89(1H, d, J=7.0 Hz), 8.01-8.06(1H, m), 7.96(1H, t, J=8.1 Hz), 7.85(1H, d, J=7.6 Hz), 4.48-4.60(1H, m), 3.71(2H, s), 3.17(3H, s), 1.47(3H, d, J=7.0 Hz) | 31 |
| 80 | 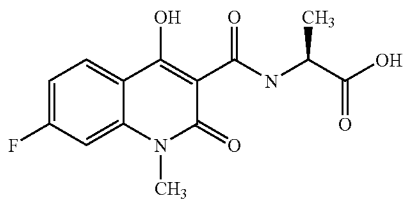 | (S)-2-(7-fluoro-4-hydroxy-1-methyl-2-oxo-1,2-dihydro-quinoline-3-carboxamido)-propanoic acid | 308.26 | 309 | 1H NMR(400 MHz, DMSO-d6): δ ppm 13.10(1H, br. s.), 10.63(1H, d, J=6.8 Hz), 8.15(1H, dd, J=8.7, 6.6 Hz), 7.54(1H, dd, J=11.5, 2.2 Hz), 7.25(1H, td, J=8.7, 2.1 Hz), 4.49-4.56(1H, m, J=7.2, 7.2, 7.2 Hz), 3.31(3H, s), 1.45(3H, d, J=7.2 Hz) | 31 |
| 81 | 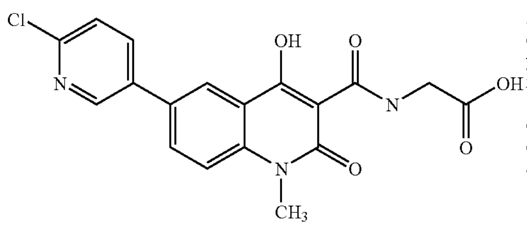 | 2-(6-(6-chloropyridin-3-yl)-4-hydroxy-1-methyl-2-oxo-1,2-dihydro-quinoline-3-carboxamido)-acetic acid | 387.77 | 388 | 1H NMR(300 MHz, DMSO-d6) δ ppm 10.55(1H, t, J=5.26 Hz), 8.84(1H, s), 8.37(1H, s), 8.28(1H, dd, J=8.3 Hz), 8.21(1H, d, J=8.9 Hz), 7.77(1H, d, J=8.8 Hz), 7.63(1H, d, J=8.3 Hz), 4.15(2H, d, J=5.4 Hz), 3.69(3H, s). | 19, 31 |
| 82 | 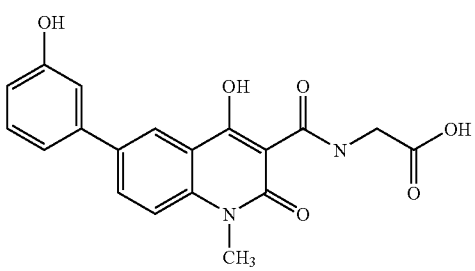 | 2-(4-hydroxy-6-(3-hydroxy-phenyl)-1-methyl-2-oxo-1,2-dihydroquinoline-3-carboxamido)-acetic acid | 368.34 | 369 | 1H NMR(300 MHz, DMSO-d6) δ ppm 10.57(1H, t, J=5.5 Hz), 9.60(1H, s), 8.24(1H, d, J=2.0 Hz), 8.08(1H, dd, J=8.8, 2.1 Hz), 7.71(1H, d, J=8.9 Hz), 7.30(1H, t, J=7.9 Hz), 7.06-7.22 (2H, m), 6.80(1H, d, J=8.0 Hz), 4.14(2H, d, J=5.6 Hz), 3.68(3H, s). | 19, 31 |
| 83 | 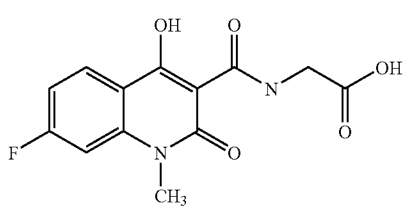 | 2-(7-fluoro-4-hydroxy-1-methyl-2-oxo-1,2-dihydro-quinoline-3-carboxamido)-acetic acid | 294.24 | 295 | 1H NMR(400 MHz, DMSO-d6): δ ppm 12.92(1H, br. s.), 10.46(1H, t, J=5.5 Hz), 8.15(1H, dd, J=8.7, 6.4 Hz), 7.53(1H, dd, J=11.4, 2.1 Hz), 7.22-7.28(1H, m), 4.13(2H, d, J=5.7 Hz), 3.61(3H, s) | 31 |
| 84 | 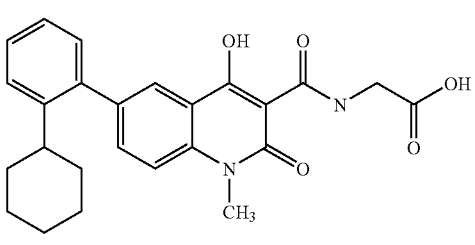 | 2-(6-(2-cyclohexyl-phenyl)-4-hydroxy-1-methyl-2-oxo-1,2-dihydro-quinoline-3-carboxamido)-acetic acid | 434.48 | 435 | | 20, 31 |

TABLE 1-continued

| Cmpd | Structure | Name | Calc'd M.W. | (M + H)+ | 1HNMR | Method(s) |
|---|---|---|---|---|---|---|
| 85 | 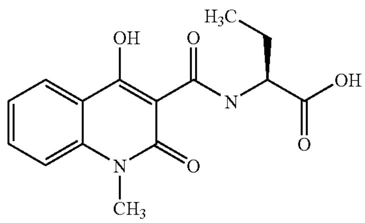 | (S)-2-(4-hydroxy-1-methyl-2-oxo-1,2-dihydro-quinoline-3-carboxamido)-butanoic acid | 304.3 | 305 | 1H NMR(400 MHz, DMSO-d6): δ ppm 8.23(1H, d, J=8.0 Hz), 7.96(1H, t, J=7.8 Hz), 7.77(1H, d, J=8.6 Hz), 7.52(1H, t, J=7.5 Hz), 4.64(1H, q, J=6.5 Hz), 3.77(3H, s), 1.88-2.10 (2H, m), 1.06(3H, t, J=7.3 Hz) | 15, 31 |
| 86 | 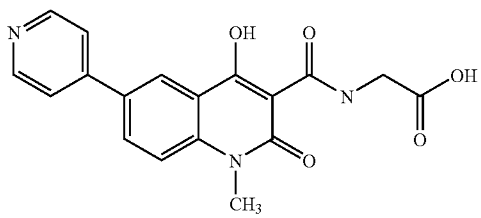 | 2-(4-hydroxy-1-methyl-2-oxo-6-(pyridin-4-yl)-1,2-dihydro-quinoline-3-carboxamido)-acetic acid | 353.33 | 354 | NMR 300 (D6-DMSO): δ ppm 10.49(1H, br t), 8.89(2H, d, J=3.0 Hz), 8.62(1H, s), 8.45-8.39(3H, m), 7.85(1H, d, J=9.0 Hz), 4.16(2H, m), 3.71(3H, s). | 15, 31 |
| 87 | 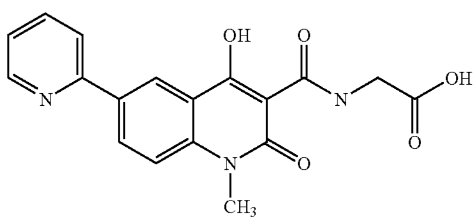 | 2-(4-hydroxy-1-methyl-2-oxo-6-(pyridin-2-yl)-1,2-dihydro-quinoline-3-carboxamido)-acetic acid | 353.33 | 354 | NMR 300: (D6-DMSO) δ ppm 10.53(1H, br t), 8.82(1H, d, J=3.0 Hz), 8.73(1H, d, J=9.0 Hz), 8.53(1H, dd, J=3.0 Hz, J=9.0 Hz), 8.15(1H, d, J=9.0 Hz), 7.99(1H, m), 7.77(1H, d, J=9.0 Hz), 7.46(1H, m), 4.16(2H, m), 3.70(3H, s). | 15, 31 |
| 88 | 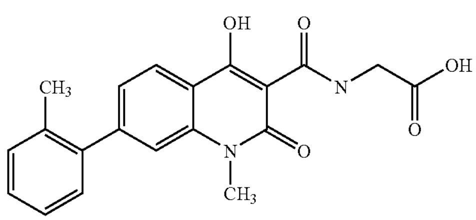 | 2-(4-hydroxy-1-methyl-2-oxo-7-o-tolyl-1,2-dihydro-quinoline-3-carboxamido)-acetic acid | 366.12 | 367 | NMR 400 (D6-DMSO): δ ppm 12.93(1H, br. s), 10.58(1H, br. t, J=5.8 Hz), 8.15 (1H, d, J=8.2 Hz), 7.54(1H, s), 7.37-7.34(5H, m), 4.15 (2H, d, J=5.7 Hz), 3.68(3H, s), 2.30(3H, s). | 21, 32 |
| 89 | 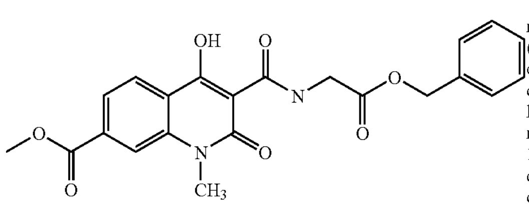 | methyl 3-((2-(benzyloxy)-2-oxoethyl)-carbamoyl)-4-hydroxy-1-methyl-2-oxo-1,2-dihydro-quinoline-7-carboxylate | 424.4 | [M − Hρ 423 | 1H NMR(300 MHz, CHLOROFORM-d) δ ppm 10.75(1H, t, J=5.4 Hz), 8.27(1H, d, J=8.5 Hz), 8.07(1H, d, J=1.1 Hz), 7.92(1H, dd, J=8.4, 1.4 Hz), 7.31-7.41(5H, m), 5.24(2H, s), 4.28(2H, d, J=5.5 Hz), 4.00(3H, s), 3.75(3H, s). | 13 |
| 90 | 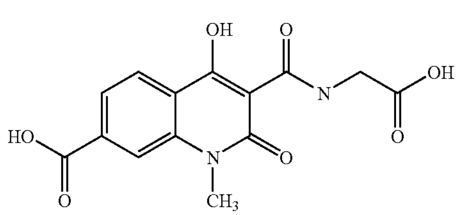 | 3-((carboxy-methyl)car-bamoyl)-4-hydroxy-1-methyl-2-oxo-1,2-dihydro-quinoline-7-carboxylic acid | 320.25 | 321 | NMR 400 (D6-DMF): δ ppm 10.7(1H, br. t, J=5.3 Hz), 8.24(1H, d, J=8.3 Hz), 8.15(1H, s), 7.94 (1H, d, J=8.3 Hz), 4.31(2H, d, J=5.5 Hz), 3.77(3H, s). | 35 |

TABLE 1-continued

| Cmpd | Structure | Name | Calc'd M.W. | (M + H)+ | 1HNMR | Method(s) |
|---|---|---|---|---|---|---|
| 91 | 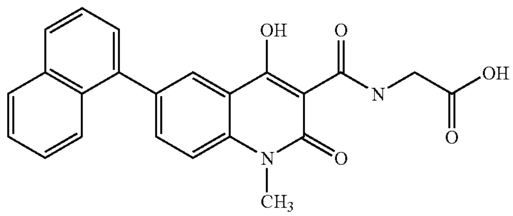 | 2-(4-hydroxy-1-methyl-6-(naphthalen-1-yl)-2-oxo-1,2-dihydro-quinoline-3-carboxamido)-acetic acid | 402.4 | 403 | 1H NMR(300 MHz, DMSO-d6) δ ppm 10.68(1H, s), 8.26(1H, s), 8.01(1H, d, J=7.6 Hz), 7.94(1H, d, J=8.3 Hz), 7.89(1H, d, J=8.5 Hz), 7.37-7.65(6H, m), 3.52-3.58(5H, m). | 19, 31 |
| 92 | 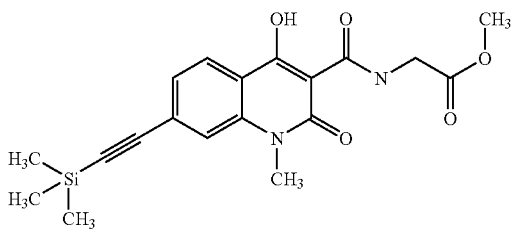 | methyl 2-(4-hydroxy-1-methyl-2-oxo-7-(2-(trimethyl-silyl)ethynyl)-1,2-dihydro-quinoline-3-carboxamido)-acetate | 386.47 | 387 | 1H NMR(400 MHz, DMSO-d6) δ ppm 10.24-10.34(1H, m), 7.81(1H, d, J=14.7 Hz), 7.38-7.45(1H, m), 7.15(1H, d, J=8.0 Hz), 3.99(2H, d, J=3.3 Hz), 3.45(3H, s), 3.41(3H, s), 0.10(9H, s) | 26 |
| 93 | 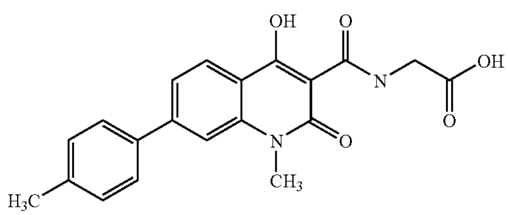 | 2-(4-hydroxy-1-methyl-2-oxo-7-p-tolyl-1,2-dihydro-quinoline-3-carboxamido)-acetic acid | 366.67 | 367 | 1H NMR(400 MHz, DMSO-d6) δ ppm 12.81-13.00(1H, m), 10.51-10.66(1H, m), 8.10-8.22(1H, m), 7.73-7.85(3H, m), 7.65-7.72(1H, m), 7.30-7.41(2H, m), 4.06-4.24(2H, m), 3.70-3.82(3H, m), 2.32-2.44(3H, m) | 31 |
| 94 | 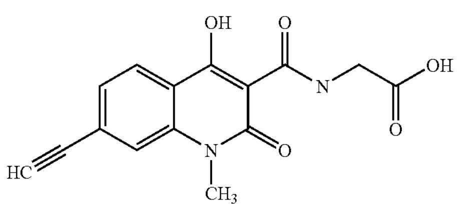 | 2-(7-ethynyl-4-hydroxy-1-methyl-2-oxo-1,2-dihydro-quinoline-3-carboxamido)-acetic acid | 300.27 | 301 | 1H NMR(400 MHz, DMSO-d6) δ ppm 12.61-12.78(1H, m), 10.16-10.33(1H, m), 7.74-7.88(1H, m), 7.41-7.53(1H, m), 7.11-7.26(1H, m), 4.35(1H, s), 3.83-3.94(2H, m), 3.11(3H, s) | 31 |
| 95 | 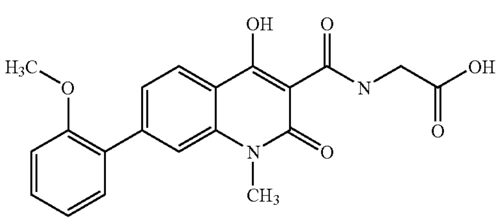 | 2-(4-hydroxy-7-(2-methoxy-phenyl)-1-methyl-2-oxo-1,2-dihydro-quinoline-3-carboxamido)-acetic acid | 382.12 | 383 | NMR 400 (D6-DMSO): δ ppm 12.92(1H, br. s), 10.58(1H, br. m), 8.10(1H, d, J=8.4 Hz), 7.65(1H, s), 7.53-7.47(3H, m), 7.20(1H, d, J=8.2 Hz), 7.10(1H, t, J=7.4 Hz), 4.14(2H, d, J=5.5 Hz), 3.81(3H, s), 3.68(3H, s). | 21, 32 |
| 96 | 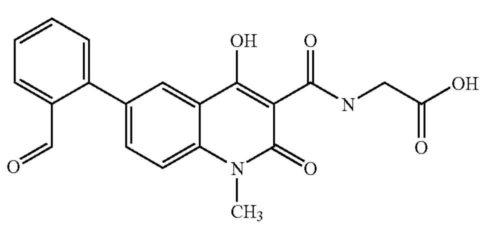 | 2-(6-(2-formylphenyl)-4-hydroxy-1-methyl-2-oxo-1,2-dihydro-quinoline-3-carboxamido)-acetic acid | 380.5 | 381 | 1H NMR(300 MHz, DMSO-d6) δ ppm 10.42(1H, t, J=4.1 Hz), 9.92(1H, s), 8.12(1H, d, J=2.2 Hz), 7.91(1H, d, J=7.6 Hz), 7.73-7.79(1H, m), 7.51-7.61(3H, m), 7.37(1H, d, J=8.9 Hz), 3.51(3H, s), 3.48(2H, d, J=4.1 Hz) | 19 |

TABLE 1-continued

| Cmpd | Structure | Name | Calc'd M.W. | (M + H)+ | 1HNMR | Method(s) |
|---|---|---|---|---|---|---|
| 97 | 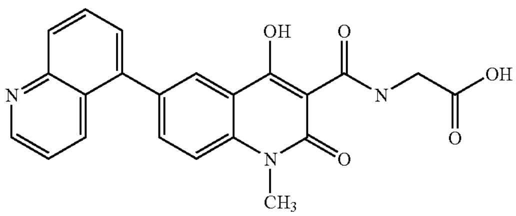 | 2-(4-hydroxy-1-methyl-2-oxo-6-(quinolin-5-yl)-1,2-dihydro-quinoline-3-carboxamido)-acetic acid | 403.39 | 404 | 1H NMR(300 MHz, DMSO-d6) δ ppm 10.58(1H, t, J=5.8 Hz), 8.97(1H, dd, J=4.1, 1.5 Hz), 8.22(1H, d, J=8.9 Hz), 8.09-8.17(2H, m), 7.95-8.00(1H, m), 7.79-7.92(2H, m), 7.66(1H, d, J=6.3 Hz), 7.56(1H, dd, J=8.6, 4.2 Hz), 4.16(2H, d, J=5.7 Hz), 3.74(3H, s) | 19 |
| 98 | 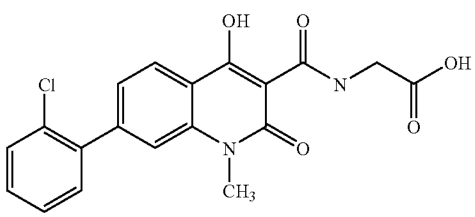 | 2-(7-(2-chlorophenyl)-4-hydroxy-1-methyl-2-oxo-1,2-dihydro-quinoline-3-carboxamido)-acetic acid | 386.07 | 387 | NMR 400 (D6-DMSO): δ ppm 12.93(1H, br. s), 10.56(1H, br. t, J=5.4 Hz), 8.17 (1H, d, J=8.2 Hz), 7.65-7.49(6H, m), 4.15(2H, d, J=5.4 Hz), 3.68(3H, s). | 21, 32 |
| 99 | 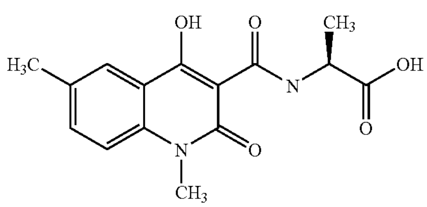 | (S)-2-(4-hydroxy-1,6-dimethyl-2-oxo-1,2-dihydro-quinoline-3-carboxamido)-propanoic acid | 304.11 | 305 | 1H NMR(400 MHz, DMSO-d6): δ ppm 10.78(1H, d, J=6.7 Hz), 7.89(1H, s), 7.66 (1H, d), 7.55(1H, d, J=8.6 Hz), 4.48-4.57(1H, m), 3.62(3H, s), 3.17(3H, s), 1.45(3H, d, J=7.0 Hz) | 31 |
| 100 | 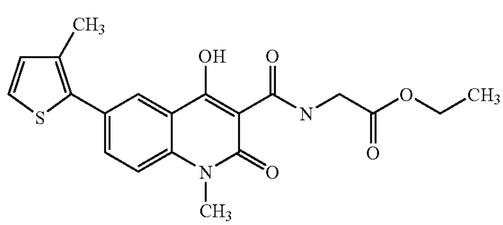 | ethyl 2-(4-hydroxy-1-methyl-6-(3-methyl-thiophen-2-yl)-2-oxo-1,2-di-hydroquinoline-3-carboxamido)-acetate | 400.45 | 401 | 1H NMR(300 MHz, CDCl3) δ ppm 10.75(1H, t, J=5.3 Hz), 8.27(1H, d, J=2.1 Hz), 7.78(1H, dd, J=8.8, 2.2 Hz), 7.39(1H, d, J=8.9 Hz), 7.24(1H, d, J=5.1 Hz), 6.95(1H, d, J=5.3 Hz), 4.28(2H, q, J=7.0 Hz), 4.22(2H, d, J=5.5 Hz), 3.71(3H, s), 2.35(3H, s), 1.31(3H, t, J=7.2 Hz) | 19 |
| 101 | 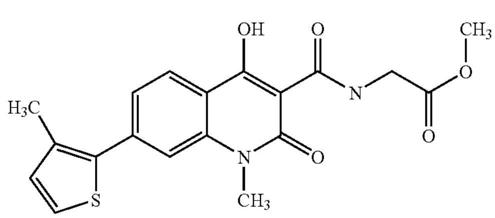 | methyl 2-(4-hydroxy-1-methyl-7-(3-methylthiophen-2-yl)-2-oxo-1,2-dihydro-quinoline-3-carboxamido)-acetate | 386.09 | 387 | NMR 400 (CDCl3): δ ppm 10.54(1H, br. s), 8.23(1H, d, J=8.6 Hz), 7.43-7.41(2H, m), 7.32(1H, d, J=4.8 Hz), 6.99(1H, d, J=4.9 Hz), 4.25(2H, d, J=5.5 Hz), 3.81(3H, s), 3.72(3H, s), 2.42(3H, s). | 21 |

TABLE 1-continued

| Cmpd | Structure | Name | Calc'd M.W. | (M + H)+ | 1HNMR | Method(s) |
|---|---|---|---|---|---|---|
| 102 | 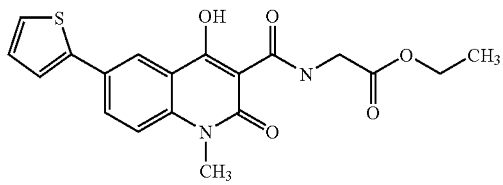 | ethyl 2-(4-hydroxy-1-methyl-2-oxo-6-(thiophen-2-yl)-1,2-dihydro-quinoline-3-carboxamido)-acetate | 386.42 | 387 | 1H NMR(300 MHz, CHLOROFORM-d) δ ppm 10.75(1H, t, J=5.1 Hz), 8.39(1H, d, J=2.3 Hz), 7.91(1H, dd, J=8.7, 2.3 Hz), 7.36-7.42(2H, m), 7.32(1H, dd, J=5.2, 1.0 Hz), 7.11(1H, d, J=5.1, 3.8 Hz), 4.28(2H, q, J=7.2 Hz), 4.23(2H, d, J=5.5 Hz), 3.70(3H, s), 1.32(3H, t, J=7.2 Hz) | 19 |
| 103 | 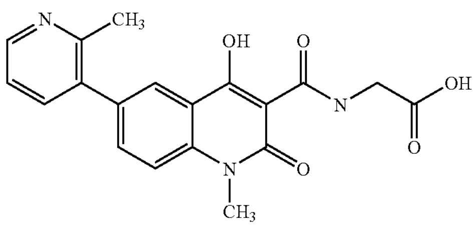 | 2-(4-hydroxy-1-methyl-6-(2-methylpyridin-3-yl)-2-oxo-1,2-dihydro-quinoline-3-carboxamido)-acetic acid | 367.35 | 368 | 1H NMR(300 MHz, DMSO-d6) δ ppm 10.51-10.63(1H, m), 8.62(1H, d, J=4.4 Hz), 8.09(1H, s), 7.88-8.03(2H, m), 7.77(1H, d, J=8.9 Hz), 7.48-7.61(1H, m), 4.15(2H, d, J=5.1 Hz), 3.70(3H, s), 2.54(3H, s) | 20, 31 |
| 104 | 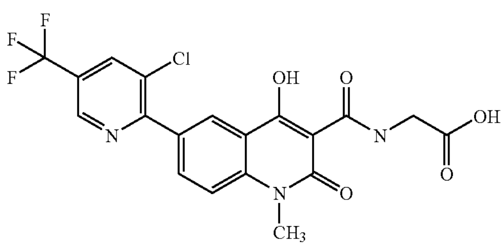 | 2-(6-(3-chloro-5-(trifluoromethyl)-pyridin-2-yl)-4-hydroxy-1-methyl-2-oxo-1,2-dihydro-quinoline-3-carboxamido)-acetic acid | 455.77 | 456 | 1H NMR(300 MHz, DMSO-d6) δ ppm 12.95(1H, s), 10.38-10.64(1H, m), 9.09(1H, s), 8.63(1H, d, J=1.3 Hz), 8.54(1H, d, J=2.0 Hz), 8.24(1H, dd, J=8.8, 2.1 Hz), 7.80(1H, d, J=9.1 Hz), 4.16(2H, d, J=5.4 Hz), 3.70(3H, s) | 20, 31 |
| 105 | 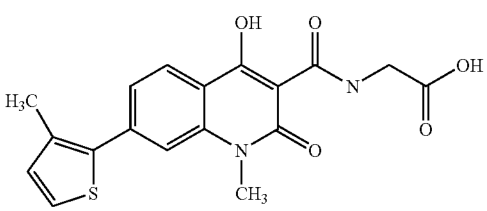 | 2-(4-hydroxy-1-methyl-7-(3-methylthiophen-2-yl)-2-oxo-1,2-dihydro-quinoline-3-carboxamido)-acetic acid | 372.4 | 373 | NMR 400 (D6-DMSO): δ ppm 12.93(1H, br. s), 10.54(1H, br. t, J=5.3 Hz), 8.15 (1H, d, J=8.2 Hz), 7.62(1H, d, J=5.2 Hz), 7.60(1H, s), 7.49(1H, br. d, J=8.2 Hz), 7.10(1H, d, J=5.1 Hz), 4.13(2H, d, J=5.3 Hz), 3.69(3H, s), 2.42(3H, s). | 32 |
| 106 | 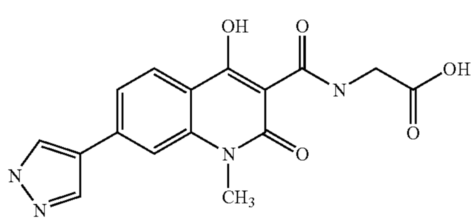 | 2-(4-hydroxy-1-methyl-2-oxo-7-(1H-pyrazol-4-yl)-1,2-dihydro-quinoline-3-carboxamido)-acetic acid | 342.31 | 343 | NMR 400 (D6-DMSO): δ ppm 13.04(2H, br. s), 10.55(1H, br. t, J=5.5 Hz), 8.36(2H, br. s), 8.03(1H, d, J=8.4 Hz), 7.77(1H, s), 7.66(1H, d, J=8.4 Hz), 4.14(2H, d, J=5.5 Hz), 3.71(3H, s). | 21, 32 |

TABLE 1-continued

| Cmpd | Structure | Name | Calc'd M.W. | (M + H)+ | 1HNMR | Method(s) |
|---|---|---|---|---|---|---|
| 107 | 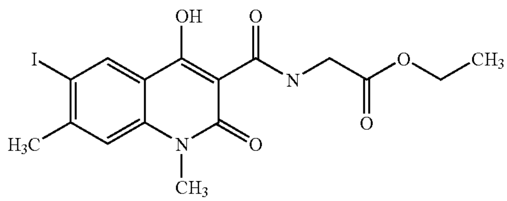 | ethyl 2-(4-hydroxy-6-iodo-1,7-dimethyl-2-oxo-1,2-dihydroquinoline-3-carboxamido)-acetate | 444.22 | 445 | 1H NMR(300 MHz, CHLOROFORM-d) δ ppm 10.68(1H, s), 8.58 (1H, s), 7.22-7.27(1H, m), 4.26(2H, q, J=7.2 Hz), 4.21(2H, d, J=5.5 Hz), 3.65(3H, s), 2.59(3H, s), 1.31(3H, t, J=7.2 Hz) | 15 |
| 108 | 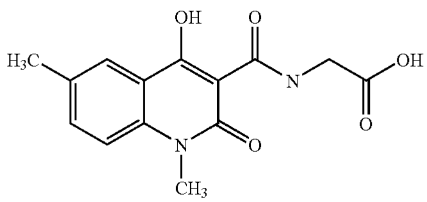 | 2-(4-hydroxy-1,6-dimethyl-2-oxo-1,2-dihydroquinoline-3-carboxamido)-acetic acid | 290.09 | 291 | 1H NMR(400 MHz, DMSO-d6): δ ppm 7.86-7.91(1H, m), 7.61-7.68(1H, m), 7.50-7.56(1H, m), 4.11(2H, d, J=5.9 Hz), 2.41(3H, s) | 31 |
| 109 | 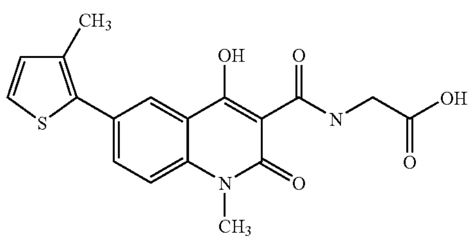 | 2-(4-hydroxy-1-methyl-6-(3-methyl-thiophen-2-yl)-2-oxo-1,2-dihydro-quinoline-3-carboxamido)-acetic acid | 372.4 | 373 | 1H NMR(300 MHz, DMSO-d6) δ ppm 10.56(1H, s), 8.09(1H, s), 7.90(1H, d, J=8.5 Hz), 7.72(1H, d, J=8.7 Hz), 7.52(1H, d, J=4.9 Hz), 7.05(1H, d, J=4.9 Hz), 4.15(2H, d, J=5.1 Hz), 3.67(3H, s), 2.33(3H, s) | 31 with LiOH |
| 110 | 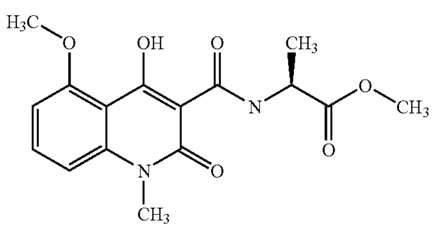 | (S)-methyl 2-(4-hydroxy-5-methoxy-1-methyl-2-oxo-1,2-dihydro-quinoline-3-carboxamido)-propanoate | 334.12 | 335 | 1H NMR(400 MHz, DMSO-d6): δ ppm 10.87(1H, d, J=6.8 Hz), 7.71(1H, t, J=8.4 Hz), 7.15(1H, d, J=8.6 Hz), 6.93(1H, d, J=8.0 Hz), 4.53-4.63(1H, m), 3.88(3H, s), 1.43(3H, d, J=7.2 Hz). | 16 |
| 111 | 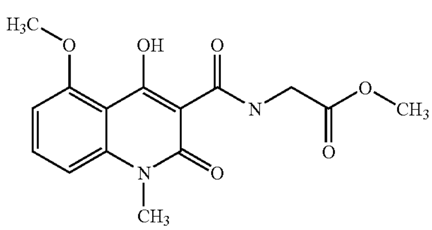 | methyl 2-(4-hydroxy-5-methoxy-1-methyl-2-oxo-1,2-dihydro-quinoline-3-carboxamido)-acetate | 320.1 | 321 | 1H NMR(400 MHz, DMSO-d6): δ ppm 10.73(1H, t, J=5.7 Hz), 7.71(1H, t, J=8.5 Hz), 7.15(1H, d, J=8.8 Hz), 6.93(1H, d, J=8.2 Hz), 4.19(2H, d, J=5.9 Hz), 3.88(3H, s), 3.55(3H, s) | 16 |
| 112 | 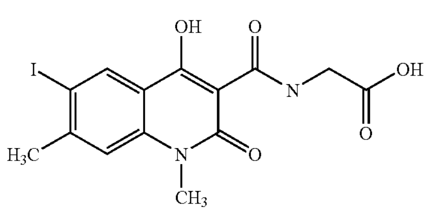 | 2-(4-hydroxy-6-iodo-1,7-dimethyl-2-oxo-1,2-dihydro-quinoline-3-carboxamido)-acetic acid | 416.17 | 417 | 1H NMR(400 MHz, DMSO-d6) δ ppm 10.50(1H, t, J=4.0 Hz), 8.40(1H, s), 7.61 (1H, s), 4.12(2H, d, J=4.0 Hz), 3.62(3H, s), 2.56(3H, s) | 31 |
| 113 | 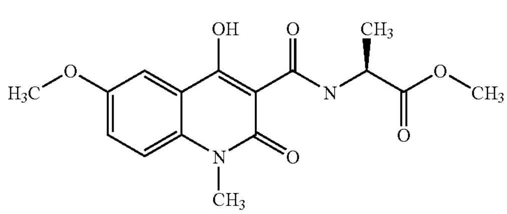 | (S)-methyl 2-(4-hydroxy-6-methoxy-1-methyl-2-oxo-1,2-dihydro-quinoline-3-carboxamido)-propanoate | 334.12 | 335 | 1H NMR(400 MHz, DMSO-d6): δ ppm 7.53-7.61(2H, m), 7.45-7.49(1H, m), 4.53-4.64(1H, m), 3.84(3H, s), 1.45(3H, d, J=7.0 Hz) | 16 |

TABLE 1-continued

| Cmpd | Structure | Name | Calc'd M.W. | (M + H)+ | 1HNMR | Method(s) |
|---|---|---|---|---|---|---|
| 114 | 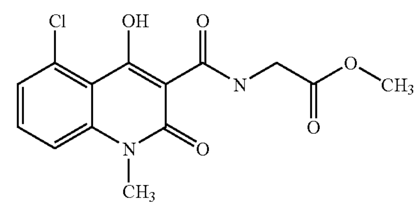 | methyl 2-(5-chloro-4-hydroxy-1-methyl-2-oxo-1,2-dihydro-quinoline-3-carboxamido)-acetate | 324.05 | 325 | 1H NMR(400 MHz, DMSO-d6): δ ppm 10.72(1H, t, J=4.7 Hz), 7.73(1H, t, J=8.1 Hz), 7.62(1H, d, J=9.0 Hz), 7.43(1H, d, J=7.8 Hz), 4.24(2H, d, J=5.7 Hz), 3.70(3H, s), 3.65(3H, s) | 16 |
| 115 | 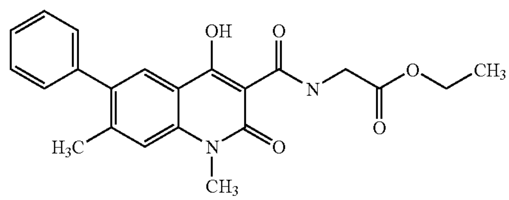 | ethyl 2-(4-hydroxy-1,7-dimethyl-2-oxo-6-phenyl-1,2-dihydro-quinoline-3-carboxamido)-acetate | 394.42 | 395 | 1H NMR(400 MHz, CHLOROFORM-d) δ ppm 10.78(1H, s), 8.05 (1H, s), 7.33-7.46 (6H, m), 4.26(2H, q, J=7.2 Hz), 4.22(2H, d, J=5.5 Hz), 3.72 (3H, s), 2.44(3H, s), 1.31(3H, t, J=7.1 Hz) | 19 |
| 116 | 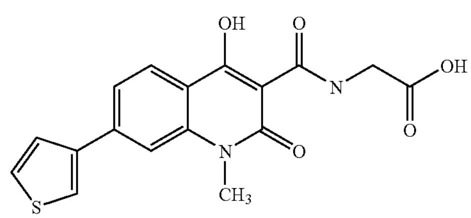 | 2-(4-hydroxy-1-methyl-2-oxo-7-(thiophen-3-yl)-1,2-dihydro-quinoline-3-carboxamido)-acetic acid | 358.37 | 359 | 1H NMR(400 MHz, DMSO-d6) δ ppm 12.82-12.99(1H, m), 10.48-10.61(1H, m), 8.20-8.33(1H, m), 8.03-8.16(1H, m), 7.69-7.90(4H, m), 4.06-4.23(2H, m), 3.75(3H, s) | 31 |
| 117 | 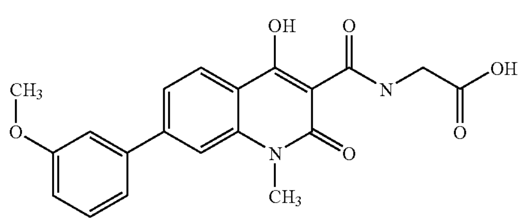 | 2-(4-hydroxy-7-(3-methoxy-phenyl)-1-methyl-2-oxo-1,2-dihydro-quinoline-3-carboxamido)-acetic acid | 382.37 | 383 | 1H NMR(400 MHz, MeOH) δ ppm 8.23(1H, d, J=8.0 Hz), 7.68-7.72(1H, m), 7.57-7.64(1H, m), 7.38-7.45(1H, m), 7.31-7.36(1H, m), 7.27-7.30(1H, m), 6.97-7.05(1H, m), 4.12-4.21(2H, m), 3.89(3H, s), 3.76(3H, s) | 31 |
| 118 | 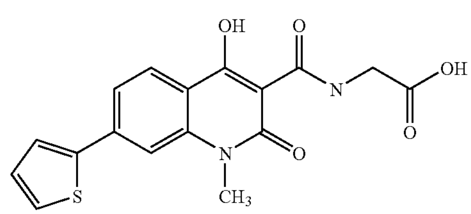 | 2-(4-hydroxy-1-methyl-2-oxo-7-(thiophen-2-yl)-1,2-dihydro-quinoline-3-carboxamido)-acetic acid | 358.37 | 359 | 1H NMR(400 MHz, DMSO-d6) δ ppm 12.87-13.02(1H, m), 10.47-10.59(1H, m), 8.05-8.14(1H, m), 7.84-7.91(1H, m), 7.72-7.80(2H, m), 7.63-7.69(1H, m), 7.21-7.28(1H, m), 4.14(2H, d, J=5.1 Hz), 3.70(3H, s) | 31 |
| 119 | 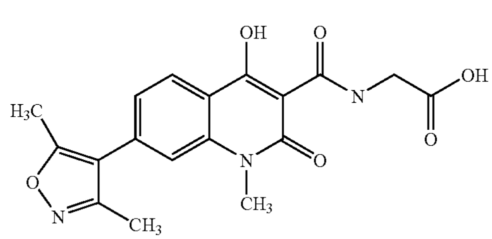 | 2-(7-(3,5-dimethyl-isoxazol-4-yl)-4-hydroxy-1-methyl-2-oxo-1,2-dihydro-quinoline-3-carboxamido)-acetic acid | 371.11 | 372 | NMR 400 (D6-DMSO): δ ppm 12.93(1H, s), 10.55 (1H, br. t, J=5.0 Hz), 8.17(1H, d, J=8.4 Hz), 7.58(1H, s), 7.43(1H, d, J=8.4 Hz), 4.15(2H, d, J=5.2 Hz), 3.68(3H, s), 2.32(3H, s). | 21, 32 |

TABLE 1-continued

| Cmpd | Structure | Name | Calc'd M.W. | (M + H)+ | 1HNMR | Method(s) |
|---|---|---|---|---|---|---|
| 120 | 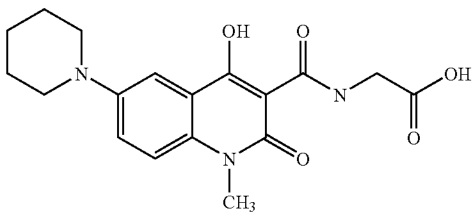 | 2-(4-hydroxy-1-methyl-2-oxo-6-(piperidin-1-yl)-1,2-dihydro-quinoline-3-carboxamido)-acetic acid | 359.38 | 360 | 1H NMR(400 MHz, DMSO-d6) δ ppm 10.67(1H, br. s.), 7.61-7.71(2H, m), 7.46-7.60(4H, m), 4.13(2H, d, J=5.5 Hz), 3.24(4H, br. s.), 1.69(6H, br. s.) | 22 |
| 121 | 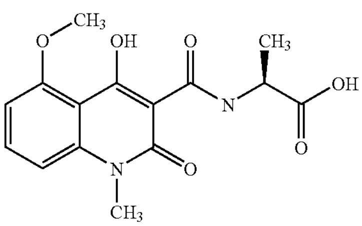 | (S)-2-(4-hydroxy-5-methoxy-1-methyl-2-oxo-1,2-dihydro-quinoline-3-carboxamido)-propanoic acid | 320.1 | 321 | 1H NMR(400 MHz, DMSO-d6) δ ppm 10.88(1H, d, J=6.8 Hz), 7.71(1H, t, J=8.4 Hz), 7.16(1H, d, J=8.6 Hz), 6.94(1H, d, J=8.2 Hz), 4.46-4.55(1H, m), 3.90(3H, s), 3.17(3H, s), 1.44(3H, d, J=7.2 Hz) | 31 |
| 122 | 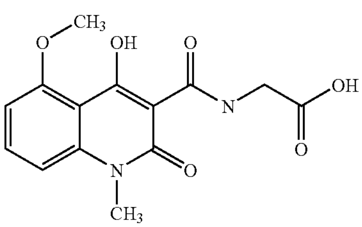 | 2-(4-hydroxy-5-methoxy-1-methyl-2-oxo-1,2-dihydro-quinoline-3-carboxamido)-acetic acid | 306.09 | 307 | 1H NMR(400 MHz, DMSO-d6): δ ppm 12.88(1H, s), 10.71(1H, s), 7.71(1H, t, J=8.0 Hz), 7.16(1H, d, J=8.8 Hz), 6.94(1H, d, J=8.2 Hz), 4.11(3H, d, J=5.5 Hz), 3.90(3H, s), 3.61(3H, s) | 31 |
| 123 | 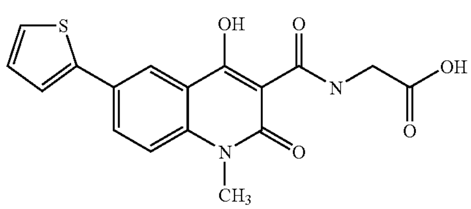 | 2-(4-hydroxy-1-methyl-2-oxo-6-(thiophen-2-yl)-1,2-dihydro-quinoline-3-carboxamido)-acetic acid | 358.37 | 359 | NMR 1H NMR (300 MHz, DMSO-d6) δ ppm 10.57(1H, s), 8.23(1H, s), 8.11(1H, d, J=3.0 Hz), 7.60(3H, m), 7.15-7.21(1H, m), 4.15(2H, d, J=6.0 Hz), 3.66(3H, s) | 31 with LiOH |
| 124 | 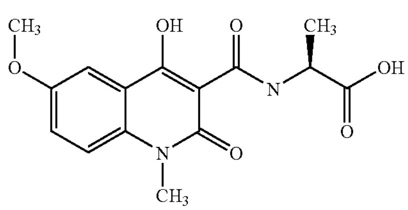 | (S)-2-(4-hydroxy-6-methoxy-1-methyl-2-oxo-1,2-dihydro-quinoline-3-carboxamido)-propanoic acid | 320.1 | 321 | 1H NMR(400 MHz, DMSO-d6): δ ppm 10.84(1H, d, J=6.7 Hz), 7.61(1H, d, J=9.0 Hz), 7.42-7.51(2H, m), 4.47-4.58(1H, m), 3.86(3H, s), 3.63(3H, s), 1.45(3H, d, J=7.2 Hz) | 31 |
| 125 | 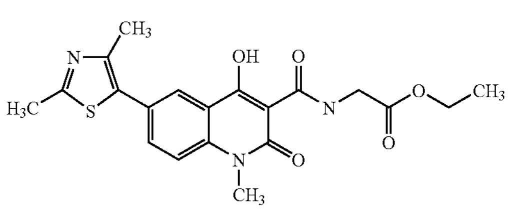 | ethyl 2-(6-(2,4-dimethylthiazol-5-yl)-4-hydroxy-1-methyl-2-oxo-1,2-dihydro-quinoline-3-carboxamido)-acetate | 415.46 | 416 | 1H NMR(300 MHz, DMSO-d6) δ ppm 10.56(1H, s), 8.05(1H, s), 7.83(2H, dd, J=10.5, 8.3 Hz), 7.43(1H, br. s.), 4.08-4.29(4H, m), 3.67(3H, s), 2.64(3H, s), 2.41(3H, s), 1.25(3H, t, J=6.4 Hz) | 30 |

TABLE 1-continued

| Cmpd | Structure | Name | Calc'd M.W. | (M + H)+ | 1HNMR | Method(s) |
|---|---|---|---|---|---|---|
| 126 | 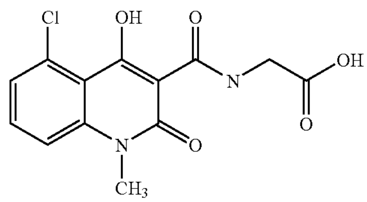 | 2-(5-chloro-4-hydroxy-1-methyl-2-oxo-1,2-dihydro-quinoline-3-carboxamido)-acetic acid | 310.04 | 311 | 1H NMR(400 MHz, DMSO-d6): δ ppm 10.70(1H, t, J=5.7 Hz), 7.72(1H, t, J=8.2 Hz), 7.62(1H, d, J=8.6 Hz), 7.42(1H, d, J=8.8 Hz), 4.14(2H, d, J=5.7 Hz), 3.64(3H, s) | 31 |
| 127 | 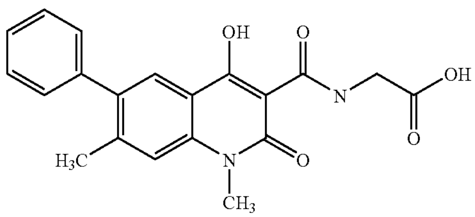 | 2-(4-hydroxy-1,7-dimethyl-2-oxo-6-phenyl-1,2-dihydro-quinoline-3-carboxamido)-acetic acid | 366.37 | 367 | 1H NMR(400 MHz, DMSO-d6) δ ppm 10.56(1H, t, J=5.5 Hz), 7.84(1H, s), 7.58 (1H, s), 7.38-7.50 (5H, m), 4.12(2H, d, J=5.5 Hz), 3.68 (3H, s), 2.42(3H, s) | 31 |
| 128 | 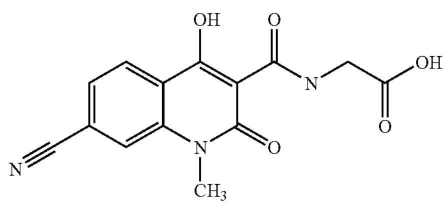 | 2-(7-cyano-4-hydroxy-1-methyl-2-oxo-1,2-dihydro-quinoline-3-carboxamido)-acetic acid | 301.25 | 302 | 1H NMR(400 MHz, DMSO-d6) δ ppm 12.87-13.05(1H, m), 10.40-10.52(1H, m), 8.19-8.26(2H, m), 7.73-7.79(1H, m), 4.15(2H, d, J=5.3 Hz), 3.67(3H, s) | 27 |
| 129 | 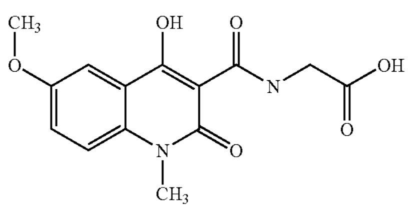 | 2-(4-hydroxy-6-methoxy-1-methyl-2-oxo-1,2-dihydro-quinoline-3-carboxamido)-acetic acid | 306.09 | 307 | 1H NMR(400 MHz, DMSO-d6): δ ppm 10.67(1H, t, J=5.4 Hz), 7.61(1H, d, J=9.2 Hz), 7.50(1H, d, J=2.5 Hz), 7.43-7.48(1H, m), 4.14(2H, d, J=5.5 Hz), 3.86(3H, s), 3.64(3H, s) | 31 |
| 130 | 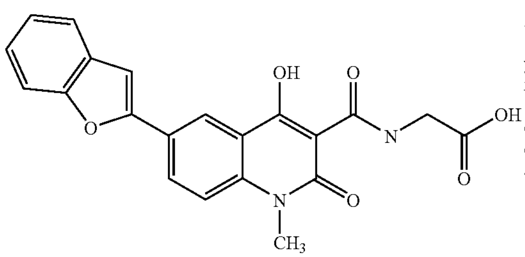 | 2-(6-(benzofuran-2-yl)-4-hydroxy-1-methyl-2-oxo-1,2-dihydro-quinoline-3-carboxamido)-acetic acid | 392.36 | 393 | 1H NMR(300 MHz, DMSO-d6) δ ppm 10.53(1H, s), 8.53(1H, s), 8.34(1H, d, J=6.3 Hz), 7.50-7.86(4H, m), 7.18-7.42(2H, m), 3.98-4.18(2H, m), 3.69(3H, s) | 19 |
| 131 | 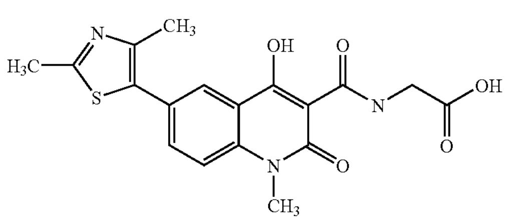 | 2-(6-(2,4-dimethylthiazol-5-yl)-4-hydroxy-1-methyl-2-oxo-1,2-dihydro-quinoline-3-carboxamido)-acetic acid | 387.41 | 388 | 1H NMR(300 MHz, DMSO-d6) δ ppm 10.54(1H, s), 8.06(1H, s), 7.88(1H, d, J=9.2 Hz), 7.74(1H, d, J=8.0 Hz), 4.15(3H, s), 3.06-3.25(2H, m), 2.65(3H, s), 2.36-2.43(3H, m) | 31 |
| 132 | 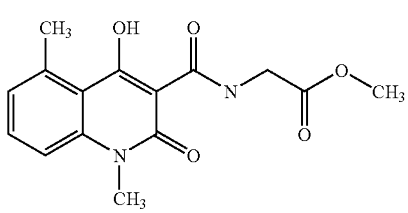 | methyl 2-(4-hydroxy-1,5-dimethyl-2-oxo-1,2-dihydro-quinoline-3-carboxamido)-acetate | 304.11 | 305 | 1H NMR(400 MHz, DMSO-d6): δ ppm 10.77(1H, t, J=5.7 Hz), 7.65(1H, t, J=8.0 Hz), 7.48(1H, d, J=8.8 Hz), 7.16(1H, d, J=7.2 Hz), 4.23(2H, d, J=5.7 Hz), 3.69(3H, s), 3.63(3H, s), 2.79(3H, s) | 16 |

TABLE 1-continued

| Cmpd | Structure | Name | Calc'd M.W. | (M + H)+ | 1HNMR | Method(s) |
|---|---|---|---|---|---|---|
| 133 | 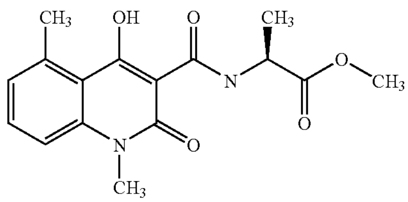 | (S)-methyl 2-(4-hydroxy-1,5-dimethyl-2-oxo-1,2-dihydro-quinoline-3-carboxamido)-propanoate | 318.12 | 319 | 1H NMR(400 MHz, DMSO-d6): δ ppm 10.94(1H, d, J=7.0 Hz), 8.03-8.12(1H, m), 7.66(1H, t, J=7.4 Hz), 7.49(1H, d, J=8.8 Hz), 7.17(1H, d, J=7.4 Hz), 4.59-4.66(1H, m, J=7.3, 7.3, 7.3 Hz), 3.67-3.73(3H, m), 3.60-3.65(3H, m), 2.76-2.81(3H, m), 1.46(1H, d, J=7.2 Hz) | 16 |
| 134 | 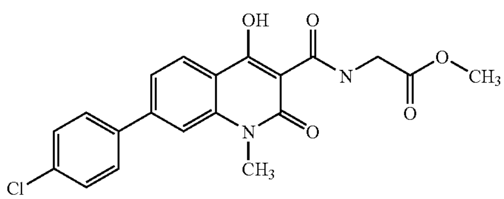 | methyl 2-(7-(4-chlorophenyl)-4-hydroxy-1-methyl-2-oxo-1,2-dihydro-quinoline-3-carboxamido)-acetate | 400.81 | 401 | | 21 |
| 135 | 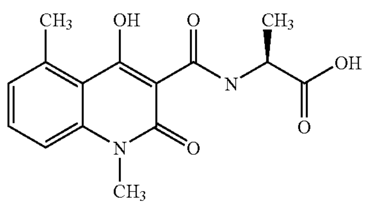 | (S)-2-(4-hydroxy-1,5-dimethyl-2-oxo-1,2-dihydro-quinoline-3-carboxamido)-propanoic acid | 304.11 | 305 | 1H NMR(400 MHz, DMSO-d6): δ ppm 10.91(1H, d, J=7.0 Hz), 7.64(1H, t, J=16.0 Hz), 7.47(1H, d, J=8.6 Hz), 7.15(1H, d, J=7.4 Hz), 4.46-4.55(1H, m), 3.62(3H, s), 2.78(3H, s), 1.45(3H, d, J=7.2 Hz) | 31 |
| 136 | 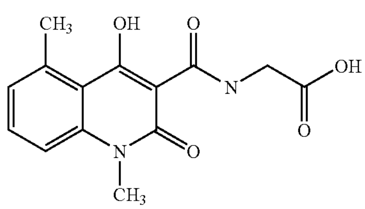 | 2-(4-hydroxy-1,5-dimethyl-2-oxo-1,2-di-hydroquinoline-3-carboxamido)-acetic acid | 290.28 | 291 | 1H NMR(400 MHz, DMSO-d6): δ ppm 7.65(1H, t, J=8.6 Hz), 7.47(1H, d, J=8.4 Hz), 7.16(1H, d, J=7.4 Hz), 4.13(2H, d, J=5.5 Hz), 3.63(3H, s), 1.91(3H, s) | 31 |
| 137 | 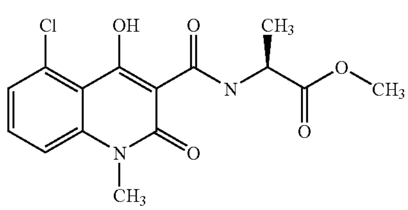 | (S)-methyl-2-(5-chloro-4-hydroxy-1-methyl-2-oxo-1,2-dihydro-quinoline-3-carboxamido)-propanoate | 338.07 | 339 | 1H NMR(400 MHz, DMSO-d6): δ ppm 10.87(1H, d, J=6.7 Hz), 7.72(1H, t, J=8.1 Hz), 7.60-7.64(1H, m), 7.43(1H, d, J=7.6 Hz), 4.57-4.68(1H, m, J=7.0, 7.0, 7.0 Hz), 3.70(3H, s), 3.63(3H, s), 1.46(3H, d, J=7.2 Hz) | 16 |
| 138 | 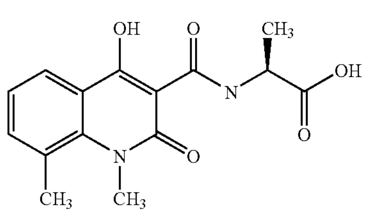 | (S)-2-(4-hydroxy-1,8-dimethyl-2-oxo-1,2-dihydro-quinoline-3-carboxamido)-propanoic acid | 304.11 | 305 | 1H NMR(400 MHz, DMSO-d6): δ ppm 10.68(1H, d, J=7.0 Hz), 7.97(1H, d, J=8.4 Hz), 7.61(1H, d, J=7.2 Hz), 7.28(1H, t, J=7.6 Hz), 4.47-4.56(1H, m), 3.72(3H, s), 2.69(3H, s), 1.45(3H, d, J=7.2 Hz) | 31 |

TABLE 1-continued

| Cmpd | Structure | Name | Calc'd M.W. | (M + H)+ | 1HNMR | Method(s) |
|---|---|---|---|---|---|---|
| 139 | 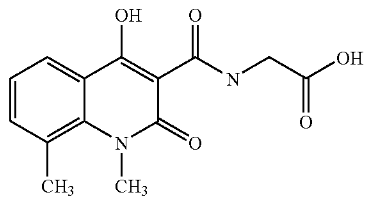 | 2-(4-hydroxy-1,8-dimethyl-2-oxo-1,2-dihydroquinoline-3-carboxamido)-acetic acid | 290.09 | 291 | 1H NMR(400 MHz, DMSO-d6): δ ppm 10.52(1H, t, J=5.6 Hz), 7.97(1H, d, J=7.6 Hz), 7.61(1H, d, J=7.8 Hz), 7.28(1H, t, J=7.7 Hz), 4.13(2H, d, J=5.7 Hz), 3.72(3H, s), 2.70(3H, s) | 31 |
| 140 | 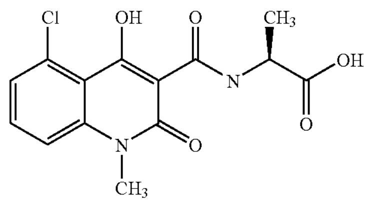 | (S)-2-(5-chloro-4-hydroxy-1-methyl-2-oxo-1,2-dihydro-quinoline-3-carboxamido)-propanoic acid | 324.05 | 325 | 1H NMR(400 MHz, DMSO-d6): δ ppm 10.88(1H, d, J=6.8 Hz), 7.72(1H, t, J=8.2 Hz), 7.62(1H, d), 7.42(1H, d, J=7.6 Hz), 4.49-4.57(1H, m), 3.64(3H, s), 1.46(3H, d, J=7.0 Hz) | 31 |
| 141 | 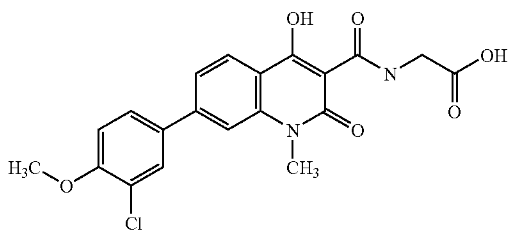 | 2-(7-(3-chloro-4-methoxy-phenyl)-4-hydroxy-1-methyl-2-oxo-1,2-dihydro-quinoline-3-carboxamido)-acetic acid | 416.81 | 417 | 1H NMR(400 MHz, DMSO-d6) δ ppm 12.93(1H, s), 10.48-10.61(1H, m), 8.11(1H, d, J=8.2 Hz), 8.00(1H, s), 7.84(1H, d, J=8.2 Hz), 7.75(1H, s), 7.67 (1H, d, J=8.2 Hz), 7.29(1H, d, J=8.6 Hz), 4.14(2H, d, J=4.9 Hz), 3.94(3H, s), 3.74(3H, s) | 21, 31 |
| 142 | 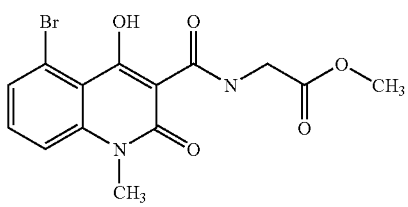 | methyl 2-(5-bromo-4-hydroxy-1-methyl-2-oxo-1,2-dihydro-quinoline-3-carboxamido)-acetate | 368 | 369/371 | 1H NMR(400 MHz, DMSO-d6): δ ppm 8.16(1H, d, J=2.3 Hz), 7.97(2H, m), 7.62 (1H, d, J=9 Hz,), 4.24(2H, d, J=5.7 Hz), 3.63(3H, s), 2.54(3H, s) | 16 |
| 143 | 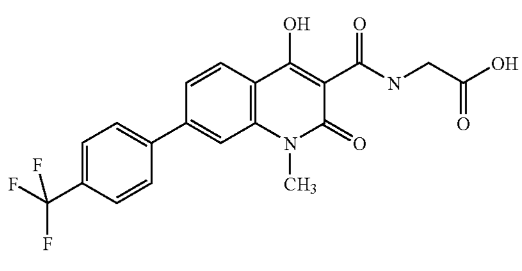 | 2-(4-hydroxy-1-methyl-2-oxo-7-(4-(trifluoro-methyl)phenyl)-1,2-dihydro-quinoline-3-carboxamido)-acetic acid | 420.34 | 421 | 1H NMR(400 MHz, DMSO-d6) δ ppm 10.22-10.77(1H, m), 8.20(1H, d, J=8.6 Hz), 8.10(2H, d, J=7.6 Hz), 7.83-7.94(3H, m), 7.74(1H, d, J=8.6 Hz), 4.15(2H, d, J=5.7 Hz), 3.76(3H, s) | 21, 31 |
| 144 | 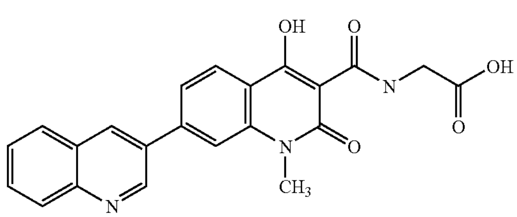 | 2-(4-hydroxy-1-(methyl-2-oxo-7-(quinolin-3-yl)-1,2-dihydro-quinoline-3-carboxamido)-acetic acid | 403.39 | 404 | 1H NMR(400 MHz, DMSO-d6) δ ppm 10.62(1H, br s), 9.58(1H, br s), 9.09(1H, br s), 8.08-8.39(4H, br m), 7.98(2H, br s), 7.82(1H, br s), 4.22(2H, br s), 3.86(3H, br s) | 21, 31 |

TABLE 1-continued

| Cmpd | Structure | Name | Calc'd M.W. | (M + H)+ | 1HNMR | Method(s) |
|---|---|---|---|---|---|---|
| 145 | 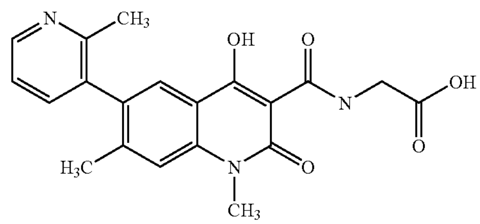 | 2-(4-hydroxy-1,7-dimethyl-6-(2-methyl-pyridin-3-yl)-2-oxo-1,2-dihydro-quinoline-3-carboxamido)-acetic acid | 381.38 | 382 | 1H NMR(400 MHz, DMSO-d6) δ ppm 10.42(1H, br s), 8.40(1H, d, J=4.0 Hz), 7.64(1H, s), 7.53(1H, s), 7.45(1H, d, J=8.0 Hz), 7.20(1H, dd, J=8.0, 4.0 Hz), 3.98(2H, br s), 3.56(3H, s), 2.09(3H, s), 2.07(3H, s) | 19 |
| 146 | 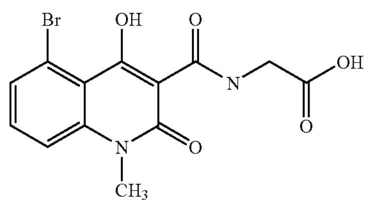 | 2-(5-bromo-4-hydroxy-1-methyl-2-oxo-1,2-dihydro-quinoline-3-carboxamido)-acetic acid | 353.99 | 355 | 1H NMR(400 MHz, DMSO-d6) δ ppm 10.50(1H, s), 8.14(1H, s), 7.95(1H, dd, J=9.0, 2.0 Hz), 7.60(1H, d, J=9.2 Hz), 4.14(2H, d, J=5.5 Hz), 3.62(3H, s). | 15, 31 |
| 147 | 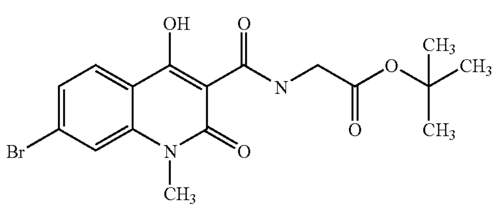 | tert-butyl 2-(7-bromo-4-hydroxy-1-methyl-2-oxo-1,2-dihydro-quinoline-3-carboxamido)-acetate | 410.1 | 355.0, 357.0 (M − $^t$Butyl + H)$^+$ | NMR 400 (CDCl$_3$): δ ppm 10.64(1H, br. s), 8.06(1H, d, J=8.41 Hz) 7.54(1H, d, J=1.37 Hz) 7.42(1H, dd, J=8.61, 1.37 Hz) 4.12(2H, d, J=5.3 Hz) 3.66(3H, s), 1.51(9H, s) ppm. | 15 |
| 148 | 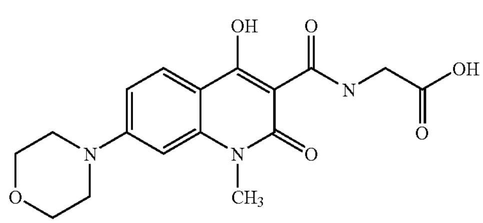 | 2-(4-hydroxy-1-methyl-7-morpholino-2-oxo-1,2-di-hydroquinoline-3-carboxamido)-aceatic acid | 361.35 | 362 | 1H NMR(400 MHz, DMSO-d6) δ ppm 10.47(1H, br. s.), 7.88(1H, d, J=9.0 Hz), 7.05(1H, d, J=8.6 Hz), 6.74(1H, br. s.), 4.08(2H, d, J=4.5 Hz), 3.76(4H, br. s.), 3.56-3.61(3H, m), 3.42(4H, br. s.) | 24 |
| 149 | 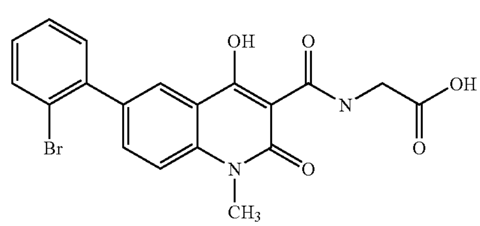 | 2-(6-(2-bromophenyl)-4-hydroxy-1-methyl-2-oxo-1,2-dihydro-quinoline-3-carboxamido)-acetic acid | 431.24 | 433 | 1H NMR(300 MHz, DMSO-d6) δ ppm 12.95(1H, s), 10.57(1H, t, J=5.5 Hz), 8.07(1H, d, J=2.0 Hz), 7.88(1H, dd, J=8.8, 2.0 Hz), 7.79(1H, d, J=7.7 Hz), 7.73(1H, d, J=8.8 Hz), 7.47-7.55(2H, m), 7.33-7.41(1H, m), 4.15(2H, d, J=5.6 Hz), 3.69(3H, s) | 19, 31 |
| 150 | 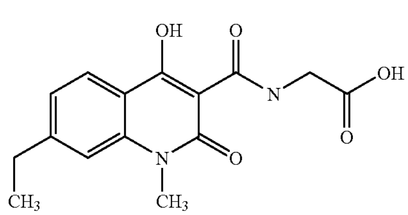 | 2-(7-ethyl-4-hydroxy-1-methyl-2-oxo-1,2-dihydro-quinoline-3-carboxamido)-acetic acid | 304.3 | 305 | 1H NMR(400 MHz, DMSO-d6) δ ppm 10.50-10.60(1H, m), 7.96-8.06(1H, m), 7.44-7.49(1H, m), 7.23-7.30(1H, m), 4.12(2H, d, J=5.3 Hz), 3.65(3H, s), 2.80(2H, q, J=7.6, 7.2 Hz), 1.27(3H, t, J=7.4 Hz) | 28 |

TABLE 1-continued

| Cmpd | Structure | Name | Calc'd M.W. | (M + H)+ | 1HNMR | Method(s) |
|---|---|---|---|---|---|---|
| 151 | 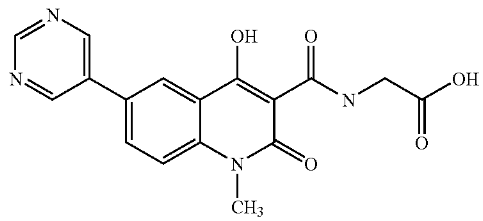 | 2-(4-hydroxy-1-methyl-2-oxo-6-(pyrimidin-5-yl)-1,2-dihydroquinoline-3-carboxamido)-acetic acid | 354.31 | 355 | 1H NMR(300 MHz, DMSO-d6) δ ppm 12.81(1H, s), 10.40(1H, t, J=5.3 Hz), 9.04-9.17(3H, m), 8.30(1H, s), 8.13(1H, d, J=8.3 Hz), 7.66(1H, d, J=8.6 Hz), 4.02(2H, d, J=5.4 Hz), 3.56(3H, s) | 20, 31 |
| 152 | 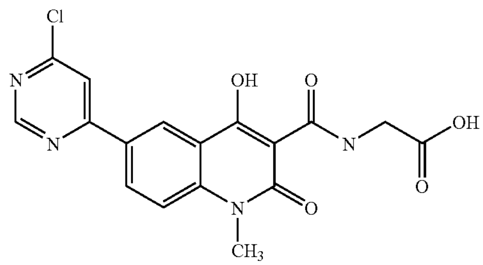 | 2-(6-(6-chloropyrimidin-4-yl)-4-hydroxy-1-methyl-2-oxo-1,2-dihydro-quinoline-3-carboxamido)-acetic acid | 388.76 | 389 | 1H NMR(300 MHz, DMSO-d6) δ ppm 10.24-10.42(1H, m), 8.99(1H, s), 8.84(1H, s), 8.51(1H, d, J=8.5 Hz), 8.34(1H, s), 7.65(1H, d, J=8.9 Hz), 4.02(2H, d, J=5.4 Hz), 3.56(3H, s) | 20, 31 |
| 153 | 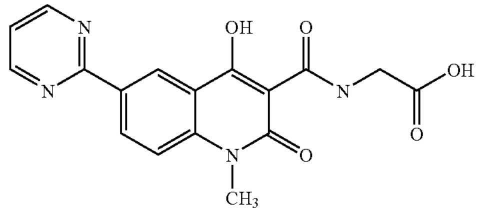 | 2-(4-hydroxy-1-methyl-2-oxo-6-(pyrimidin-2-yl)-1,2-dihydroquinoline-3-carboxamido)-acetic acid | 354.32 | 355 | 1H NMR(300 MHz, DMSO-d6) δ ppm 9.14(1H, s), 8.94(2H, d, J=4.4 Hz), 8.76(1H, d, J=8.8 Hz), 7.79(1H, d, J=9.5 Hz), 7.48(1H, t, J=4.3 Hz), 4.15(2H, d, J=4.4 Hz), 3.69(3H, s) | 20, 31 |
| 154 | 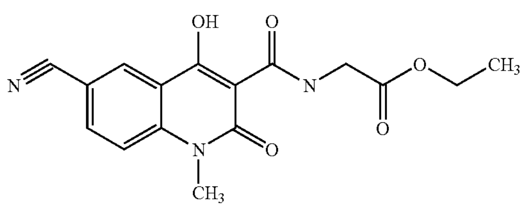 | ethyl 2-(6-cyano-4-hydroxy-1-methyl-2-oxo-1,2-dihydroquinoline-3-carboxamido)-acetate | 329.31 | 330 | 1H NMR(400 MHz, DMSO-d6) δ ppm 10.41(1H, s), 8.47(1H, s), 8.19(1H, d, J=8.4 Hz), 7.79(1H, d, J=8.8 Hz), 4.22(2H, d, J=4.9 Hz), 4.16(2H, q, J=6.9 Hz), 3.65(3H, s), 1.22(3H, t, J=7.0 Hz) | 29 |
| 155 | 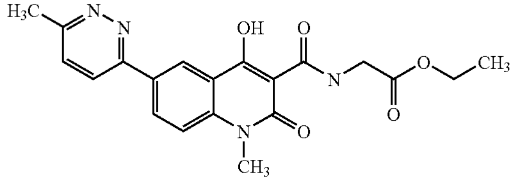 | ethyl 2-(4-hydroxy-1-methyl-6-(6-methylpyridazin-3-yl)-2-oxo-1,2-dihydroquinoline-3-carboxamido)-acetate | 396.4 | 397 | 1H NMR(400 MHz, DMSO-d6) δ ppm 10.51-10.61(1H, m), 8.84(1H, s), 8.57(1H, d, J=9.2 Hz), 8.27(1H, d, J=8.4 Hz), 7.81(1H, d, J=8.6 Hz), 7.68(1H, d, J=9.0 Hz), 4.23(2H, d, J=4.3 Hz), 4.16(2H, q, J=7.4, 6.8 Hz), 3.71(3H, s), 2.68(3H, s), 1.23(3H, t, J=6.9 Hz) | 30 |
| 156 | 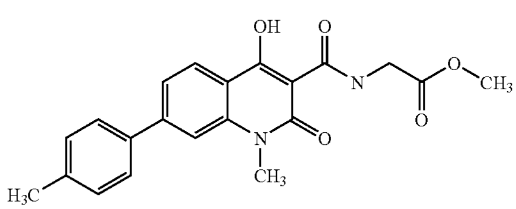 | methyl 2-(4-hydroxy-1-methyl-2-oxo-7-p-tolyl-1,2-dihydroquinoline-3-carboxamido)-acetate | 380.39 | 381 | 1H NMR(400 MHz, DMF) δ ppm 10.91-11.00(1H, m), 8.36-8.42(1H, m), 8.05-8.09(1H, m), 7.98-8.04(2H, m), 7.89-7.94(1H, m), 7.53-7.61(2H, m), 4.54(2H, d, J=5.5 Hz), 4.04(3H, s), 3.95(3H, s), 2.61(3H, s) | 21, 31 |

TABLE 1-continued

| Cmpd | Structure | Name | Calc'd M.W. | (M + H)+ | 1HNMR | Method(s) |
|---|---|---|---|---|---|---|
| 157 | 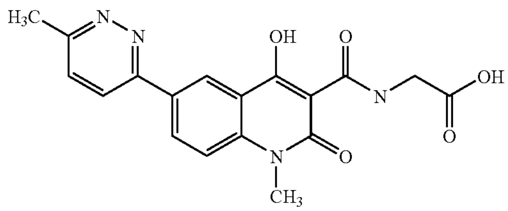 | 2-(4-hydroxy-1-methyl-6-(6-methylpyridazin-3-yl)-2-oxo-1,2-dihydroquinoline-3-carboxamido)-acetic acid | 368.34 | 369 | 1H NMR(400 MHz, DMSO-d6) δ ppm 10.52(1H, s), 8.83 (1H, s), 8.56(1H, d, J=8.8 Hz), 8.40(1H, d, J=8.6 Hz), 7.83(2H, d, J=8.6 Hz), 4.15(2H, d, J=4.1 Hz), 3.70(3H, s), 2.71(3H, s) | 31 |
| 158 | 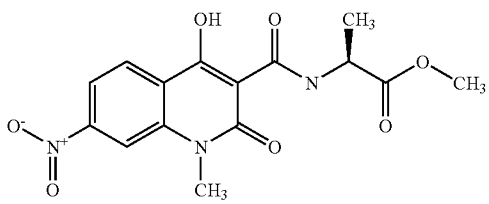 | (S)-methyl 2-(4-hydroxy-1-methyl-7-nitro-2-oxo-1,2-dihydroquinoline-3-carboxamido)-propanoate | 349.09 | 350 | 1H NMR(400 MHz, DMSO-d6): δ ppm 8.29-8.35(2H, m), 8.13(1H, dd, J=8.9, 1.9 Hz), 4.59-4.68 (1H, m), 3.77(3H, s), 3.70(3H, s), 1.47(3H, d, J=7.2 Hz) | 16 |
| 159 | 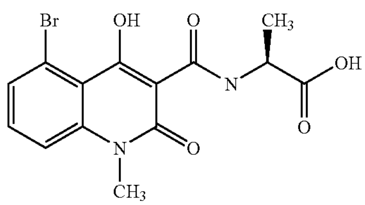 | (S)-2-(5-bromo-4-hydroxy-1-methyl-2-oxo-1,2-dihydroquinoline-3-carboxamido)-propanoic acid | 369.17 | 369 | 1H NMR(400 MHz, DMSO-d6): δ ppm 10.65(1H, d, J=7.2 Hz), 8.12-8.16(1H, m), 7.94(1H, d, J=11.0 Hz), 7.59(1H, d, J=9.0 Hz), 4.46-4.55(1H, m), 1.44(3H, d, J=7.0 Hz) | 31 |
| 160 | 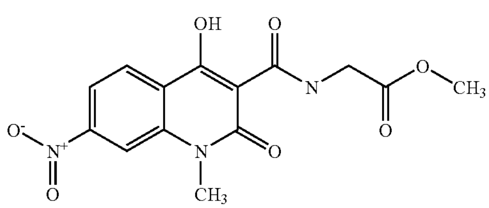 | methyl 2-(4-hydroxy-1-methyl-7-nitro-2-oxo-1,2-dihydroquinoline-3-carboxamido)-acetate | 335.08 | 336 | 1H NMR(400 MHz, DMSO-d6): δ ppm 10.50(1H, s), 8.32-8.34(1H, m), 8.30(1H, s), 8.12(1H, dd, J=8.8, 2.0 Hz), 4.25(2H, d, J=5.7 Hz), 3.72(3H, s), 2.54(3H, s) | 16 |
| 161 | 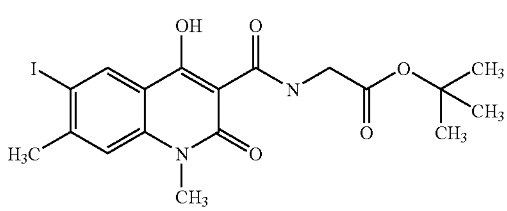 | tert-butyl 2-(4-hydroxy-6-iodo-1,7-dimethyl-2-oxo-1,2-dihydroquinoline-3-carboxamido)-acetate | 472.27 | 417 (M − tBu) | 1H NMR(400 MHz, CHLOROFORM-d) δ ppm 10.67(1H, s), 8.56(1H, s), 7.20-7.27(1H, m, J=18.2 Hz), 4.12(2H, d, J=5.3 Hz), 3.64(3H, s), 2.58(3H, s), 1.50(9H, s) | 15 |
| 162 | 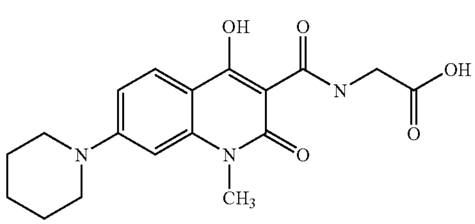 | 2-(4-hydroxy-1-methyl-2-oxo-7-(piperidin-1-yl)-1,2-dihydroquinoline-3-carboxamido)-acetic acid | 359.38 | 360 | 1H NMR(400 MHz, DMSO-d6) δ ppm 10.48(1H, t, J=5.5 Hz), 7.84(1H, d, J=9.2 Hz), 7.01(1H, dd, J=9.2, 2.0 Hz), 6.68(1H, d, J=1.4 Hz), 4.10(2H, d, J=5.7 Hz), 3.58(3H, s), 3.49(4H, br. s.), 1.63(6H, br. s.) | 25 |

TABLE 1-continued

| Cmpd | Structure | Name | Calc'd M.W. | (M + H)+ | 1HNMR | Method(s) |
|---|---|---|---|---|---|---|
| 163 | 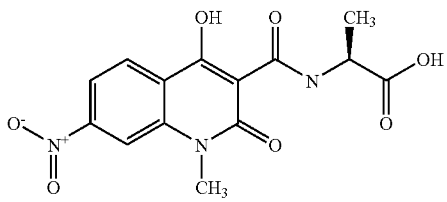 | (S)-2-(4-hydroxy-1-methyl-7-nitro-2-oxo-1,2-dihydroquinoline-3-carboxamido)-propanoic acid | 335.08 | 336 | 1H NMR(400 MHz, DMSO-d6): δ ppm 13.17(1H, br. s.), 10.62(1H, d, J=6.7 Hz), 8.34(1H, s), 8.32(1H, d, J=9.0 Hz), 8.13(1H, dd, J=8.7, 1.1 Hz), 4.50-4.59(1H, m), 3.72(3H, s), 1.47(3H, d, J=7.2 Hz) | 31 |
| 164 | 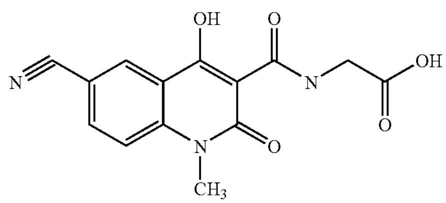 | 2-(6-cyano-4-hydroxy-1-methyl-2-oxo-1,2-dihydro-quinoline-3-carboxamido)-acetic acid | 301.25 | 302 | 1H NMR(300 MHz, DMSO-d6) δ ppm 12.94(1H, br. s.), 10.40(1H, s), 8.47(1H, s), 8.17(1H, d, J=8.5 Hz), 7.81(1H, d, J=8.9 Hz), 4.14(2H, d, J=4.3 Hz), 3.65(3H, s) | 31 |
| 165 | 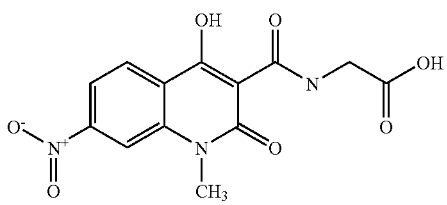 | 2-(4-hydroxy-1-methyl-7-nitro-2-oxo-1,2-dihydroquinoline-3-carboxamido)-acetic acid | 321.06 | 322 | 1H NMR(400 MHz, DMSO-d6): δ ppm 10.44(1H, br. s.), 8.24-8.37(2H, m), 8.12(1H, d, J=8.4 Hz), 4.15(2H, d, J=5.3 Hz), 3.71(3H, s) | 31 |
| 166 | 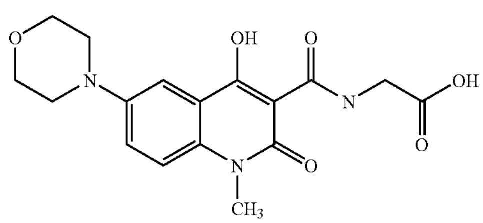 | 2-(4-hydroxy-1-methyl-6-morpholino-2-oxo-1,2-dihydroquinoline-3-carboxamido)-acetic acid | 361.35 | 362 | 1H NMR(400 MHz, DMSO-d6) δ ppm 10.69(1H, t, J=5.3 Hz), 7.59(1H, dd, J=2.5 Hz), 7.55(1H, d, J=9.2 Hz), 7.42(1H, d, J=2.3 Hz), 4.13(2H, d, J=5.5 Hz), 3.78(4H, t, J=4.3 Hz), 3.62(3H, s), 3.13-3.19(4H, m) | 23 |
| 167 | 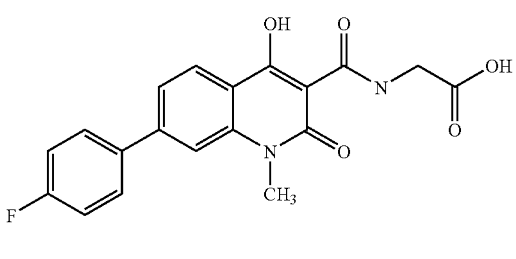 | 2-(7-(4-fluorophenyl)-4-hydroxy-1-methyl-2-oxo-1,2-dihydro-quinoline-3-carboxamido)-acetic acid | 370.33 | 371 | 1H NMR(400 MHz, DMSO-d6) δ ppm 10.48-10.64(1H, m), 8.16(1H, d, J=8.4 Hz), 7.88-7.99(2H, m), 7.79(1H, s), 7.68(1H, d, J=8.2 Hz), 7.30-7.44(2H, m), 4.15(2H, d, J=5.3 Hz), 3.75(3H, s) | 21, 31 |
| 168 | 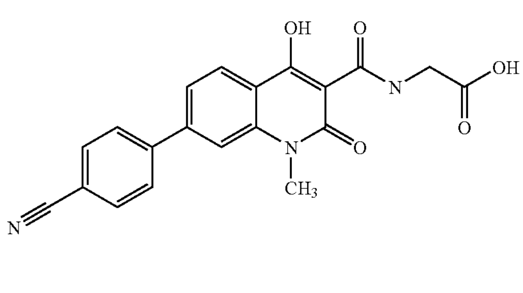 | 2-(7-(4-cyanophenyl)-4-hydroxy-1-methyl-2-oxo-1,2-dihydro-quinoline-3-carboxamido)-acetic acid | 377.35 | 378 | 1H NMR(400 MHz, DMSO-d6) δ ppm 10.59(1H, br s), 8.00-8.27(5H, br m), 7.90(1H, br s), 7.78(1H, br s), 4.19(2H, br s), 3.79(3H, br s) | 21, 31 |

TABLE 1-continued

| Cmpd | Structure | Name | Calc'd M.W. | (M + H)+ | 1HNMR | Method(s) |
|---|---|---|---|---|---|---|
| 169 | 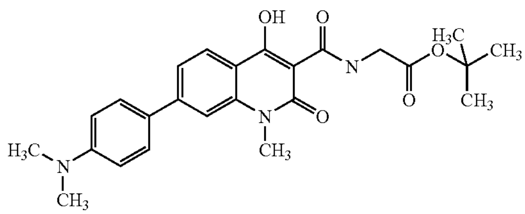 | tert-butyl 2-(7-(4-(dimethylamino)phenyl)-4-hydroxy-1-methyl-2-oxo-1,2-dihydroquinoline-3-carboxamido)-acetate | 451.52 | 452 | 1H NMR(400 MHz, CHLOROFORM-d) δ ppm 10.72-10.81(1H, m), 8.19(1H, d, J=8.4 Hz), 7.60(2H, d, J=8.6 Hz), 7.50(1H, d, J=8.6 Hz), 7.47(1H, s), 6.82(2H, d, J=8.4 Hz), 4.14(2H, d, J=5.1 Hz), 3.75(3H, s), 3.04(6H, s), 1.51(9H, s) | 21 |
| 170 | 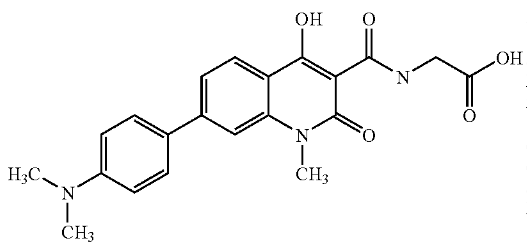 | 2-(7-(4-(dimethylamino)phenyl)-4-hydroxy-1-methyl-2-oxo-1,2-dihydroquinoline-3-carboxamido)-acetic acid hydrochloride | 395.41 | 396 | 1H NMR(400 MHz, DMSO-d6) δ ppm 10.54-10.66(1H, br s), 8.12(1H, br d, J=9.4 Hz), 7.81(2H, br d, J=8.2 Hz), 7.71-7.77(1H, br s), 7.68(1H, br d, J=6.5 Hz), 6.89(2H, br d, J=6.8 Hz), 4.19(2H, br d, J=6.3 Hz), 3.78(3H, br s), 3.04(6H, br s) | 21, 33 |
| 171 | 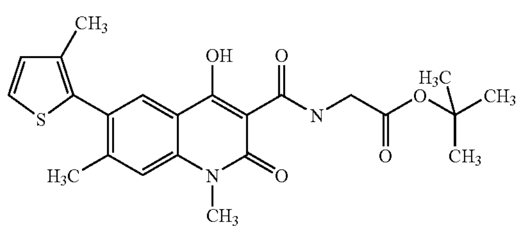 | tert-butyl 2-(4 hydroxy-1,7-dimethyl-6-(3-methylthiophen-2-yl)-2-oxo-1,2-dihydroquinoline-3-carboxamido)-acetate | 442.53 | 443 | 1H NMR(400 MHz, DMSO-d6) δ ppm 10.53(1H, br s), 7.85(1H, s), 7.64(1H, s), 7.55(1H, d, J=8.0 Hz), 7.05(1H, d, J=8.0 Hz), 4.11(2H, d, J=4.0 Hz), 3.67(3H, s), 2.33(3H, s), 2.01(3H, s), 1.45(9H, s) | 19 |
| 172 | 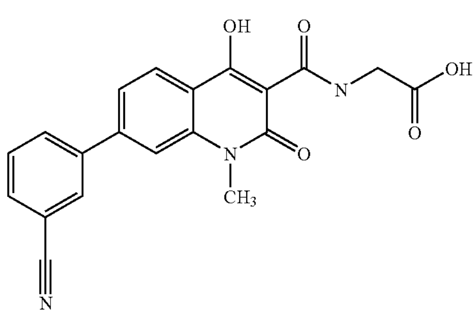 | 2-(7-(3-cyanophenyl)-4-hydroxy-1-methyl-2-oxo-1,2-dihydroquinoline-3-carboxamido)-acetic acid | 377.35 | 376 (MH) | 1H NMR(400 MHz, DMSO-d6) δ ppm 10.36-10.50(1H, br s), 8.32(1H, br s), 7.98-8.18(2H, br m), 7.74-7.88(2H, br m), 7.58-7.71(2H, br d), 4.04(2H, br s), 3.66(3H, br s) | 21, 34 |
| 173 | 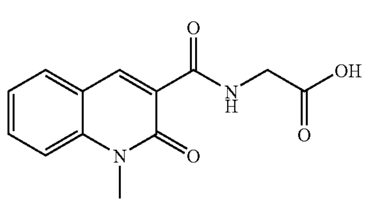 | 2-(1-methyl-2-oxo-1,2-dihydroquinoline-3-carboxamido)-acetic acid | 260.24 | 261 | 1H NMR(400 MHz, DMSO-d6) δ ppm: 12.26-13.26(1H, br s), 9.75-10.27(1H, br s), 8.68-9.09(1H, br s), 7.95-8.22(1H, br s), 7.49-7.91(2H, br m), 7.11-7.46(1H, br s), 3.98-4.26(2H, br s), 3.57-3.88(3H, br s) | 36 |

TABLE 1-continued

| Cmpd | Structure | Name | Calc'd M.W. | (M + H)+ | 1HNMR | Method(s) |
|---|---|---|---|---|---|---|
| 174 | 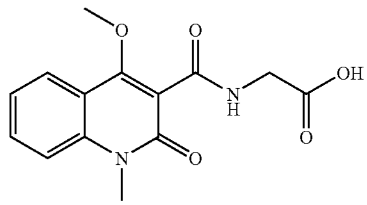 | 2-(4-methoxy-2-oxo-1,2-di-hydroquinoline-3-carboxamido)-acetic acid | 290.28 | 291 | 1H NMR(300 MHz, DMSO-d6) δ ppm 12.61(1H, s), 8.77(1H, t, J=5.8 Hz), 7.95(1H, dd, J=8.0, 1.3 Hz), 7.64-7.72 (1H, m), 7.54(1H, d, J=8.2 Hz), 7.27-7.34(1H, m), 4.14(3H, s), 3.94(2H, d, J=5.8 Hz), 3.58(3H, s) | 37 |
| 175 | 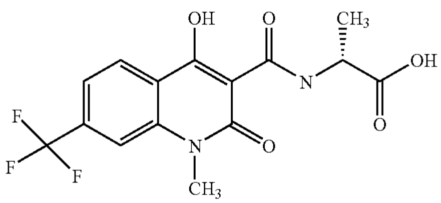 | (S)-2-(4-hydroxy-1-methyl-2-oxo-7-(trifluoro-methyl)-1,2-dihydro-quinoline-3-carboxamido)-propanoic acid | 358.08 | 359 | 1H NMR(400 MHz, CHLOROFORM-d): 10.71(1H, d, J=6.7 Hz), 8.35(1H, d, J=8.4 Hz), 7.61(1H, s), 7.55(1H, d, J=8.4 Hz), 4.73-4.82(1H, m, J=7.0, 7.0, 7.0 Hz), 3.74(3H, s), 1.63(3H, d, J=7.2 Hz) | 15, 31 |

What is claimed is:

1. A compound of Formula I:

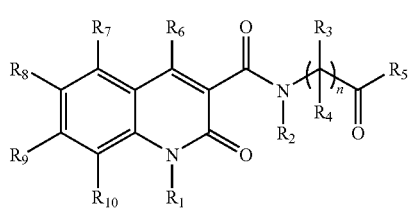

or a pharmaceutically acceptable salt thereof, wherein:

n is 1;

$R_1$ is chosen from H, lower alkyl and substituted lower alkyl;

$R_2$ is H;

$R_3$ and $R_4$ are each H;

$R_5$ is chosen from OH, SH, $NH_2$, lower alkyl, substituted lower alkyl, lower alkoxy, substituted lower alkoxy and sulfanyl;

$R_6$ is OH; and each of $R_7$, $R_8$, $R_9$ and $R_{10}$ is independently chosen from H, alkyl, substituted alkyl, alkenyl, substituted alkenyl, alkynyl, substituted alkynyl, alkoxy, substituted alkoxy, $NR_3,R_4$, C(O)OH, $OR_{13}$, $SR_{13}$, $SO_2R_{13}$, CN, $NO_2$, halo, aryl, substituted aryl, heteroaryl, substituted heteroaryl, heteroarylalkyl, substituted heteroarylalkyl, heterocycloalkyl, substituted heterocycloalkyl, alkylsilyl, substituted alkylsilyl, alkynylsilyl, substituted alkynylsilyl, alkoxy, substituted alkoxy, alkoxycarbonyl, substituted alkoxycarbonyl, and —X—$R_{12}$, wherein:

$R_3'$ and $R_4'$ are independently chosen from H, lower alkyl, substituted lower alkyl, lower haloalkyl, substituted lower haloalkyl;

X is chosen from —N($R_{11}$)—Y and —Y—N($R_{11}$)—;

Y is chosen from C(O), $SO_2$, alkylene, substituted alkylene, alkenylene, substituted alkenylene, alkynylene, and substituted alkynylene;

$R_{11}$ is chosen from H, lower alkyl, and substituted lower alkyl;

$R_{12}$ is chosen from H, heterocycloalkyl, substituted heterocycloalkyl, aryl, substituted aryl, heteroaryl and substituted heteroaryl; and $R_{13}$ is chosen from H, alkyl, substituted alkyl, alkenyl, substituted alkenyl, alkynyl and substituted alkynyl;

wherein optionally at least one of adjacent pairs $R_7$ and $R_8$, $R_8$ and $R_9$, and $R_9$ and $R_{10}$, join together to form a 4 to 7 membered ring or a substituted 4 to 7 membered ring.

2. The compound according to claim 1, wherein at least one of $R_7$, $R_8$, $R_9$ and $R_{10}$ is independently chosen from halo and a moiety substituted with at least one halo.

3. The compound according to claim 1, wherein at least one of $R_7$, $R_8$, $R_9$ and $R_{10}$ is independently chosen from alkoxy or substituted alkoxy.

4. The compound according to claim 1, wherein at least one of $R_7$, $R_8$, $R_9$ and $R_{10}$ is independently chosen from aryl, substituted aryl, heteroaryl, substituted heteroaryl, heterocycloalkyl, and substituted heterocycloalkyl.

5. The compound according to claim 1, wherein each of $R_7$, $R_8$, $R_9$ and $R_{10}$ is independently chosen from H, alkyl, substituted alkyl, alkenyl, substituted alkenyl, alkynyl, and substituted alkynyl.

6. The compound according to claim 1, wherein the compound is selected from:

Methyl 2-(4-hydroxy-1-methyl-2-oxo-1,2-dihydroquinoline-3-carboxamido)acetate;

2-(4-Hydroxy-1-methyl-2-oxo-1,2-dihydroquinoline-3-carboxamido)acetic acid;

2-(6-Bromo-4-hydroxy-1-methyl-2-oxo-1,2-dihydroquinoline-3-carboxamido)acetic acid;

2-(6-Chloro-4-hydroxy-1-methyl-2-oxo-1,2-dihydroquinoline-3-carboxamido)acetic acid;

Methyl 2-(4-hydroxy-6-iodo-1-methyl-2-oxo-1,2-dihydroquinoline-3-carboxamido)acetate;

2-(4-Hydroxy-6-iodo-1-methyl-2-oxo-1,2-dihydroquinoline-3-carboxamido)acetic acid;

2-(4-Hydroxy-1-methyl-2-oxo-6-phenyl-1,2-dihydroquinoline-3-carboxamido)acetic acid;

2-(6-(4-Tertbutylphenyl)-4-hydroxy-1-methyl-2-oxo-1,2-dihydroquinoline-3-carboxamido)acetic acid;

Methyl 2-(7-chloro-4-hydroxy-1-methyl-2-oxo-1,2-dihydroquinoline-3-carboxamido)acetate;

2-(4-Hydroxy-1-methyl-2-oxo-6-(4-(trifluoromethyl)phenyl)-1,2-dihydroquinoline-3-carboxamido)acetic acid;

2-(4-Hydroxy-1-methyl-2-oxo-6-(3-(trifluoromethyl)phenyl)-1,2-dihydroquinoline-3-carboxamido)acetic acid;

2-(6-(2-Fluorophenyl)-4-hydroxy-1-methyl-2-oxo-1,2-dihydroquinoline-3-carboxamido)acetic acid;

2-(6-(3-Fluorophenyl)-4-hydroxy-1-methyl-2-oxo-1,2-dihydroquinoline-3-carboxamido)acetic acid;

2-(6-(4-Fluorophenyl)-4-hydroxy-1-methyl-2-oxo-1,2-dihydroquinoline-3-carboxamido)acetic acid;

2-(4-Hydroxy-6-(3-isopropylphenyl)-1-methyl-2-oxo-1,2-dihydroquinoline-3-carboxamido)acetic acid;

2-(4-Hydroxy-6-(4-methoxyphenyl)-1-methyl-2-oxo-1,2-dihydroquinoline-3-carboxamido)acetic acid;

2-(4-Hydroxy-1-methyl-6-(naphthalen-2-yl)-2-oxo-1,2-dihydroquinoline-3-carboxamido)acetic acid;

2-(6-(Benzo[b]thiophen-2-yl)-4-hydroxy-1-methyl-2-oxo-1,2-dihydroquinoline-3-carboxamido)acetic acid;

2-(4-Hydroxy-1-methyl-2-oxo-6-(4-phenoxyphenyl)-1,2-dihydroquinoline-3-carboxamido)acetic acid;

2-(6-(2-Chlorophenyl)-4-hydroxy-1-methyl-2-oxo-1,2-dihydroquinoline-3-carboxamido)acetic acid;

2-(6-(3-Chlorophenyl)-4-hydroxy-1-methyl-2-oxo-1,2-dihydroquinoline-3-carboxamido)acetic acid;

2-(4-Hydroxy-6-(1H-indol-5-yl)-1-methyl-2-oxo-1,2-dihydroquinoline-3-carboxamido)acetic acid;

2-(7-Chloro-4-hydroxy-1-methyl-2-oxo-1,2-dihydroquinoline-3-carboxamido)acetic acid;

Methyl 2-(7-bromo-4-hydroxy-1-methyl-2-oxo-1,2-dihydroquinoline-3-carboxamido)acetate;

Methyl 2-(4-hydroxy-1-methyl-2-oxo-7-phenyl-1,2-dihydroquinoline-3-carboxamido)acetate;

2-(7-Bromo-4-hydroxy-1-methyl-2-oxo-1,2-dihydroquinoline-3-carboxamido)acetic acid;

2-(4-Hydroxy-1-methyl-2-oxo-7-phenyl-1,2-dihydroquinoline-3-carboxamido)acetic acid;

2-(4-Hydroxy-6-(2-methoxyphenyl)-1-methyl-2-oxo-1,2-dihydroquinoline-3-carboxamido)acetic acid;

2-(6-(4-Chlorophenyl)-4-hydroxy-1-methyl-2-oxo-1,2-dihydroquinoline-3-carboxamido)acetic acid;

2-(6-(3-Formylphenyl)-4-hydroxy-1-methyl-2-oxo-1,2-dihydroquinoline-3-carboxamido)acetic acid;

2-(4-Hydroxy-6-(3-methoxyphenyl)-1-methyl-2-oxo-1,2-dihydroquinoline-3-carboxamido)acetic acid;

2-(7-(3-Chlorophenyl)-4-hydroxy-1-methyl-2-oxo-1,2-dihydroquinoline-3-carboxamido)acetic acid;

2-(7-(4-Chlorophenyl)-4-hydroxy-1-methyl-2-oxo-1,2-dihydroquinoline-3-carboxamido)acetic acid;

N-(2-Amino-2-oxoethyl)-4-hydroxy-1-methyl-2-oxo-1,2-dihydroquinoline-3-carboxamide;

Methyl 2-(4-hydroxy-1-methyl-2-oxo-7-(trifluoromethyl)-1,2-dihydroquinoline-3-carboxamido)acetate;

2-(1-Ethyl-4-hydroxy-2-oxo-1,2-dihydroquinoline-3-carboxamido)acetic acid;

2-(4-Hydroxy-7-(4-methoxyphenyl)-1-methyl-2-oxo-1,2-dihydroquinoline-3-carboxamido)acetic acid;

2-(4-Hydroxy-1-methyl-2-oxo-7-(trifluoromethyl)-1,2-dihydroquinoline-3-carboxamido)acetic acid;

Methyl 2-(4-hydroxy-1,7-dimethyl-2-oxo-1,2-dihydroquinoline-3-carboxamido)acetate;

2-(4-Hydroxy-1,7-dimethyl-2-oxo-1,2-dihydroquinoline-3-carboxamido)acetic acid;

2-(4-Hydroxy-1-methyl-2-oxo-6-(2-phenyl)-phenyl-1,2-dihydroquinoline-3-carboxamido)acetic acid;

2-(4-Hydroxy-1-methyl-2-oxo-6-(pyridin-3-yl)-1,2-dihydroquinoline-3-carboxamido)acetic acid;

2-(6-(2-Chloro-5-methylpyrimidin-4-yl)-4-hydroxy-1-methyl-2-oxo-1,2-dihydroquinoline-3-carboxamido)acetic acid;

Methyl 2-(4-hydroxy-8-methoxy-1-methyl-2-oxo-1,2-dihydroquinoline-3-carboxamido)acetate;

2-(4-Hydroxy-1-methyl-2-oxo-6-(3-piperidin-1-yl)phenyl)-1,2-dihydroquinoline-3-carboxamido)acetic acid;

2-(4-Hydroxy-1-methyl-2-oxo-6-(3-(pyrrolidin-1-yl)phenyl)-1,2-dihydroquinoline-3-carboxamido)acetic acid;

Ethyl 2-(4-hydroxy-6-iodo-1-methyl-2-oxo-1,2-dihydroquinoline-3-carboxamido)acetate;

Methyl 2-(5-fluoro-4-hydroxy-1-methyl-2-oxo-1,2-dihydroquinoline-3-carboxamido)acetate;

2-(4-Hydroxy-8-methoxy-1-methyl-2-oxo-1,2-dihydroquinoline-3-carboxamido)acetic acid;

Methyl 2-(6-fluoro-4-hydroxy-1-methyl-2-oxo-1,2-dihydroquinoline-3-carboxamido)acetate;

2-(5-Fluoro-4-hydroxy-1-methyl-2-oxo-1,2-dihydroquinoline-3-carboxamido)acetic acid;

Methyl 2-(4-hydroxy-1-methyl-2-oxo-5-(trifluoromethyl)-1,2-dihydroquinoline-3-carboxamido)acetate;

Methyl 2-(7-fluoro-4-hydroxy-1-methyl-2-oxo-1,2-dihydroquinoline-3-carboxamido)acetate;
2-(4-Hydroxy-1-methyl-2-oxo-5(trifluoromethyl)-1,2-dihydroquinolin-3-carboxamido)acetic acid;
2-(6-Fluoro-4-hydroxy-1-methyl-2-oxo-1,2-dihydroquinolin-3-carboxamido)acetic acid;
2-(6-(6-Chloropyridin-3-yl)-4-hydroxy-1-methyl-2-oxo-1,2-dihydroquinoline-3-carboxamido)acetic acid;
2-(4-Hydroxy-6-(3-hydroxyphenyl)-1-methyl-2-oxo-1,2-dihydroquinoline-3-carboxamido)acetic acid;
2-(7-Fluoro-4-hydroxy-1-methyl-2-oxo-1,2-dihydroquinoline-3-carboxamido)acetic acid;
2-(6-(2-Cyclohexylphenyl)-4-hydroxy-1-methyl-2-oxo-1,2-dihydroquinoline-3-carboxamido)acetic acid;
2-(4-Hydroxy-1-methyl-2-oxo-6-(pyridin-4-yl)-1,2-dihydroquinoline-3-carboxamido)acetic acid;
2-(4-Hydroxy-1-methyl-2-oxo-6-(pyridin-2-yl)-1,2-dihydroquinoline-3-carboxamido)acetic acid;
2-(4-Hydroxy-1-methyl-2-oxo-7-o-tolyl-1,2-dihydroquinoline-3-carboxamido)acetic acid;
Methyl 3-((2-(benzyloxy)-2-oxoethyl)carbamoyl)-4-hydroxy-1-methyl-2-oxo-1,2-dihydroquinoline-7-carboxylate;
3-((Carboxymethyl)carbamoyl)-4-hydroxy-1-methyl-2-oxo-1,2-dihydroquinoline-7-carboxylic acid;
2-(4-Hydroxy-1-methyl-6-(naphthalen-1-yl)-2-oxo-1,2-dihydroquinoline-3-carboxamido)acetic acid;
Methyl 2-(4-hydroxy-1-methyl-2-oxo-7-(2-(trimethylsilyl)ethynyl)-1,2-dihydroquinoline-3-carboxamido)acetate;
2-(4-Hydroxy-1-methyl-2-oxo-7-p-tolyl-1,2-dihydroquinoline-3-carboxamido)acetic acid;
2-(7-Ethynyl-4-hydroxy-1-methyl-2-oxo-1,2-dihydroquinoline-3-carboxamido)acetic acid;
2-(4-Hydroxy-7-(2-methoxyphenyl)-1-methyl-2-oxo-1,2-dihydroquinoline-3-carboxamido)acetic acid;
2-(6-(2-Formylphenyl)-4-hydroxy-1-methyl-2-oxo-1,2-dihydroquinoline-3-carboxamido)acetic acid;
2-(4-Hydroxy-1-methyl-2-oxo-6-(quinolin-5-yl)-1,2-dihydroquinoline-3-carboxamido)acetic acid;
2-(7-(2-Chlorophenyl)-4-hydroxy-1-methyl-2-oxo-1,2-dihydroquinoline-3-carboxamido)acetic acid;
Ethyl 2-(4-hydroxy-1-methyl-6-(3-methylthiophen-2-yl)-2-oxo-1,2-dihydroquinoline-3-carboxamido)acetate;
Methyl 2-(4-hydroxy-1-methyl-7-(3-methylthiophen-2-yl)-2-oxo-1,2-dihydroquinoline-3-carboxamido)acetate;
Ethyl 2-(4-hydroxy-1-methyl-2-oxo-6-(thiophen-2-yl)-1,2-dihydroquinoline-3-carboxamido)acetate;
2-(4-Hydroxy-1-methyl-6-(2-methylpyridin-3-yl)-2-oxo-1,2-dihydroquinoline-3-carboxamido)acetic acid;
2-(6-(3-Chloro-5-(trifluoromethyl)pyridin-2-yl)-4-hydroxy-1-methyl-2-oxo-1,2-dihydroquinoline-3-carboxamido)acetic acid;
2-(4-Hydroxy-1-methyl-7-(3-methylthiophen-2-yl)-2-oxo-1,2-dihydroquinoline-3-carboxamido)acetic acid;
2-(4-Hydroxy-1-methyl-2-oxo-7-(1H-pyrazol-4-yl)-1,2-dihydroquinoline-3-carboxamido)acetic acid;
Ethyl 2-(4-hydroxy-6-iodo-1,7-dimethyl-2-oxo-1,2-dihydroquinoline-3-carboxamido)acetate;
2-(4-Hydroxy-1,6-dimethyl-2-oxo-1,2-dihydroquinoline-3-carboxamido)acetic acid;
2-(4-Hydroxy-1-methyl-6-(3-methylthiophen-2-yl)-2-oxo-1,2-dihydroquinoline-3-carboxamido)acetic acid;
Methyl 2-(4-hydroxy-5-methoxy-1-methyl-2-oxo-1,2-dihydroquinoline-3-carboxamido)acetate;
2-(4-Hydroxy-6-iodo-1,7-dimethyl-2-oxo-1,2-dihydroquinoline-3-carboxamido)acetic acid;
Methyl 2-(5-chloro-4-hydroxy-1-methyl-2-oxo-1,2-dihydroquinoline-3-carboxamido)acetate;
Ethyl 2-(4-hydroxy-1,7-dimethyl-2-oxo-6-phenyl-1,2-dihydroquinoline-3-carboxamido)acetate;
2-(4-Hydroxy-1-methyl-2-oxo-7-(thiophen-3-yl)-1,2-dihydroquinoline-3-carboxamido)acetic acid;
2-(4-Hydroxy-7-(3-methoxyphenyl)-1-methyl-2-oxo-1,2-dihydroquinoline-3-carboxamido)acetic acid;
2-(4-Hydroxy-1-methyl-2-oxo-7-(thiophen-2-yl)-1,2-dihydroquinoline-3-carboxamido)acetic acid;
2-(7-(3,5-dimethylisoxazol-4-yl)-4-hydroxy-1-methyl-2-oxo-1,2-dihydroquinoline-3-carboxamido)acetic acid;
2-(4-Hydroxy-1-methyl-2-oxo-6-(piperidin-1-yl)-1,2-dihydroquinoline-3-carboxamido)acetic acid;
2-(4-Hydroxy-5-methoxy-1-methyl-2-oxo-1,2-dihydroquinoline-3-carboxamido)acetic acid;
2-(4-Hydroxy-1-methyl-2-oxo-6-(thiophen-2-yl)-1,2-dihydroquinoline-3-carboxamido)acetic acid;
Ethyl 2-(6-(2,4-dimethylthiazol5-yl)-4-hydroxy-1-methyl-2-oxo-1,2-dihydroquinoline-3-carboxamido)acetate;
2-(5-Chloro-4-hydroxy-1-methyl-2-oxo-1,2-dihydroquinoline-3-carboxamido)acetic acid;
2-(4-Hydroxy-1,7-dimethyl-2-oxo-6-phenyl-1,2-dihydroquinoline-3-carboxamido)acetic acid;
2-(7-Cyano-4-hydroxy-1-methyl-2-oxo-1,2-dihydroquinoline-3-carboxamido)acetic acid;
2-(4-Hydroxy-6-methoxy-1-methyl-2-oxo-1,2-dihydroquinoline-3-carboxamido)acetic acid;
2-(6-(Benzofuran-2-yl)-4-hydroxy-1-methyl-2-oxo-1,2-dihydroquinoline-3-carboxamido)acetic acid;
2-(6-(2,4-Dimethylthiazol-5-yl)-4-hydroxy-1-methyl-2-oxo-1,2-dihydroquinoline-3-carboxamido)acetic acid;
Methyl 2-(4-hydroxy-1,5-dimethyl-2-oxo-1,2-dihydroquinoline-3-carboxamido)acetate;
Methyl 2-(7-(4-chlorophenyl)-4-hydroxy-1-methyl-2-oxo-1,2-dihydroquinoline-3-carboxamido)acetate;
2-(4-Hydroxy-1,5-dimethyl-2-oxo-1,2-dihydroquinoline-3-carboxamido)acetic acid;
2-(4-Hydroxy-1,8-dimethyl-2-oxo-1,2-dihydroquinoline-3-carboxamido)acetic acid;
2-(7-(3-Chloro-4-methoxyphenyl)-4-hydroxy-1-methyl-2-oxo-1,2-dihydroquinoline-3-carboxamido)acetic acid;
Methyl 2-(5-bromo-4-hydroxy-1-methyl-2-oxo-1,2-dihydroquinoline-3-carboxamido)acetate;
2-(4-Hydroxy-1-methyl-2-oxo-7-(4-(trifluoromethyl)phenyl)-1,2-dihydroquinoline-3-carboxamido)acetic acid;
2-(4-Hydroxy-1-(methyl-2-oxo-7-(quinolin-3-yl)-1,2-dihydroquinoline-3-carboxamido)acetic acid;
2-(4-Hydroxy-1,7-dimethyl-6-(2-methylpyridin-3-yl)-2-oxo-1,2-dihydroquinoline-3-carboxamido)acetic acid;
2-(5-Bromo-4-hydroxy-1-methyl-2-oxo-1,2-dihydroquinoline-3-carboxamido)acetic acid;
Tert-butyl 2-(7-bromo-4-hydroxy-1-methyl-2-oxo-1,2-dihydroquinoline-3-carboxamido)acetate;
2-(4-Hydroxy-1-methyl-7-morpholino-2-oxo-1,2-dihydroquinoline-3-carboxamido)acetic acid;
2-(6-(2-Bromophenyl)-4-hydroxy-1-methyl-2-oxo-1,2-dihydroquinoline-3-carboxamido)acetic acid;
2-(7-Ethyl-4-hydroxy-1-methyl-2-oxo-1,2-dihydroquinoline-3-carboxamido)acetic acid;
2-(4-Hydroxy-1-methyl-2-oxo-6-(pyrimidin-5-yl)-1,2-dihydroquinoline-3-carboxamido)acetic acid;

2-(6-(6-Chloropyrimidin-4-yl)-4-hydroxyl-methyl-2-oxo-1,2-dihydroquinoline-3-carboxamido)acetic acid;

2-(4-Hydroxy-1-methyl-2-oxo-6-(pyrimidin-2-yl)-1,2-dihydroquinoline-3-carboxamido)acetic acid;

Ethyl 2-(6-cyano-4-hydroxy-1-methyl-2-oxo-1,2-dihydroquinoline-3-carboxamido)acetate;

Ethyl 2-(4-hydroxy-1-methyl-6-(6-methylpyridazin-3-yl)-2-oxo-1,2-dihydroquinoline-3-carboxamido)acetate;

Methyl 2-(4-hydroxy-1-methyl-2-oxo-7-p-tolyl-1,2-dihydroquinoline-3-carboxamido)acetate;

2-(4-Hydroxy-1-methyl-6-(6-methylpyridazin-3-yl)-2-oxo-1,2-dihydroquinoline-3-carboxamido)acetic acid;

Methyl 2-(4-hydroxy-1-methyl-7-nitro-2-oxo-1,2-dihydroquinoline-3-carboxamido)acetate;

Tert-butyl 2-(4-hydroxy-6-iodo-1,7-dimethyl-2-oxo-1,2-dihydroquinoline-3-carboxamido)acetate;

2-(4-Hydroxy-1-methyl-2-oxo-7-(piperidin-1-yl)-1,2-dihydroquinoline-3-carboxamido)acetic acid;

2-(6-Cyano-4-hydroxy-1-methyl-2-oxo-1,2-dihydroquinoline-3-carboxamido)acetic acid;

2-(4-Hydroxy-1-methyl-7-nitro-2-oxo-1,2-dihydroquinoline-3-carboxamido)acetic acid;

2-(4-Hydroxy-1-methyl-6-morpholino-2-oxo-1,2-dihydroquinoline-3-carboxamido)acetic acid;

2-(7-(4-Fluorophenyl)-4-hydroxy-1-methyl-2-oxo-1,2-dihydroquinoline-3-carboxamido)acetic acid;

2-(7-(4-Cyanophenyl)-4-hydroxy-1-methyl-2-oxo-1,2-dihydroquinoline-3-carboxamido)acetic acid;

Tert-butyl 2-(7-(4-(dimethylamino)phenyl)-4-hydroxy-1-methyl-2-oxo-1,2-dihydroquinoline-3-carboxamido)acetate;

2-(7-(4-(Dimethylamino)phenyl)-4-hydroxy-1-methyl-2-oxo-1,2-dihydroquinoline-3-carboxamido)acetic acid hydrochloride;

Tert-butyl 2-(4-hydroxy-1,7-dimethyl-6-(3-methylthiophen-2-yl)-2-oxo-1,2-dihydroquinoline-3-carboxamido)acetate; or and 2-(7-(3-Cyanophenyl)-4-hydroxy-1-methyl-2-oxo-1,2-dihydroquinoline-3-carboxamido)acetic acid.

\* \* \* \* \*

UNITED STATES PATENT AND TRADEMARK OFFICE
CERTIFICATE OF CORRECTION

| | | |
|---|---|---|
| PATENT NO. | : 7,728,130 B2 | Page 1 of 1 |
| APPLICATION NO. | : 11/635683 | |
| DATED | : June 1, 2010 | |
| INVENTOR(S) | : Allen et al. | |

It is certified that error appears in the above-identified patent and that said Letters Patent is hereby corrected as shown below:

Title Page, Item (75) Inventors: Delete "Jennifer Dao, Robert Kurzeja" and "Violeta Yu".

Signed and Sealed this
Twentieth Day of September, 2011

David J. Kappos
*Director of the United States Patent and Trademark Office*